United States Patent [19]
Landau et al.

[11] Patent Number: 6,057,102
[45] Date of Patent: May 2, 2000

[54] HIV CORECEPTOR MUTANTS

[75] Inventors: Nathaniel R. Landau, New York, N.Y.; Richard A. Koup, Southlake, Tex.; Rong Liu, New York, N.Y.; William Paxton, Amsterdam, Netherlands

[73] Assignee: The Aaron Diamond Aids Research Center, New York, N.Y.

[21] Appl. No.: 08/907,468

[22] Filed: Aug. 8, 1997

Related U.S. Application Data

[60] Provisional application No. 60/025,230, Aug. 8, 1996.

[51] Int. Cl.⁷ .............................. C12Q 1/68; C12Q 1/70
[52] U.S. Cl. ................................ 435/6; 435/5; 435/91.2; 435/91.21; 436/501; 436/504; 536/23.1; 536/23.5
[58] Field of Search .................................. 435/5, 6, 91.2, 435/91.21; 436/501, 504; 536/23.1, 23.5, 23.72, 24.3, 24.31

[56] References Cited

U.S. PATENT DOCUMENTS 5,399,346   3/1995   Anderson et al. .................... 424/93.21

FOREIGN PATENT DOCUMENTS

| | | |
|---|---|---|
| WO 92/00252 | 1/1992 | WIPO . |
| WO 94/24282 | 10/1994 | WIPO . |
| WO 94/28028 | 12/1994 | WIPO . |
| WO 95/28494 | 10/1995 | WIPO . |
| WO 96/23068 | 8/1996 | WIPO . |
| WO 96/41884 | 12/1996 | WIPO . |
| WO 97/45543 | 4/1997 | WIPO . |
| WO 97/21812 | 6/1997 | WIPO . |
| WO 97/22698 | 6/1997 | WIPO . |
| WO 97/32019 | 9/1997 | WIPO . |
| WO 97/44055 | 11/1997 | WIPO . |
| WO 97/44359 | 11/1997 | WIPO . |
| WO 97/44360 | 11/1997 | WIPO . |

OTHER PUBLICATIONS

Feng et al., Science 272: 872–877, May 10, 1996.
Deng et al., Nature 381: 661–666, Jun. 20, 1996.
Dragic et al., Nature 381:667–673, Jun. 20, 1996.
Alkhatib et al., Science 272:1955–1958, Jun. 28, 1996.
Choe et al., Cell 85: 1135–1148, Jun. 28, 1996.
Doranz et al., Cell 85: 1149–1158, Jun. 28, 1996.
Liu et al., Cell 86: 367–377, Aug. 9, 1996.
Alkhatib (1996) Science 272:1955–8.
Baggiolini et al(1995) Int J Immunopharmacol 17:103–8.
Bates et al. (1996) Cell 86:1–3.
Bedinger et al(1988) Nature 334:162–5.
Benton and Davis(1977) Science 196:180.
Cao et al N Engl J Med 332:201–8.
Cech(1988) J Am Med Assoc 260:3030.
Chou (1996) Cell 85:1135–48.
Cocchi et al(1996) Science 720:1811–5.
Combadiere et al., DNA Cell. Biol. 14:673–680 (1995).
Connor et al (1995) Virol 206:936–44.
Deng et al(1996) Nature 381:661–6.
Dimitrov(1996) Nature Medicine 2:640–1.
Doranz (1996) Cell 85:1149–58.
Dragic et al(1996) Nature 381:667–73.
Feng et al(1996) Science 272:872–7.
Field et al(1988) Molec Cell Biol 8:2159–65.
Fodor et al(1991) Science 251:767–73.
Geysen et al(1986) Mole Immunol 23:709–15.
Goodson(1984) in: Medical Applications of Controlled ReleaseLanger and Wise eds., CRC Press: Boca Raton, Florida, Chapter 6, pp. 115–138.
Hanks et al(1995) Science 269:679–82.
He and Landau(1995) J Virol 69:4587–92.
Higuchi(1989) in PCR Technology: Principles and Applications for DNA Amplification, Erlich ed, Stockton Press:61–70.
Horuk, Trends Pharmacol. Sci. 15:159–65 (1994).
Horuk et al(1993) Science 261:1182–4.
Hutchinson et al(1978) J Biol Chem 253:6551.
Kaplitt et al(1991) Molec Cell Neurosci 2:320–30.
Killeen et al. (1993) EMBO J. 12:1547–53.
Landau and Littman (1988) Nature 334:159–62.
Landau and Littman (1992) J Virol 66:5110–3.
Landau et al (1991) J Virol 65:162–9.
Langer and Peppas(1983) J Macromol Sci Rev Macromol Chem 23:61–126.
Langer(1990) Science 249:1527–33.
Lenburg and Landau(1993) J Virol 67:7238–45.
Liu et al. (1996) Cell 86:367–77.
Locke et al(1988) Somat Cell Mol Genet 19:95–101.
Lusso, P. (1997) Nature Med. 3:1074–5.
MacDonald et al., Nature Genet. 1:99–103 (1992).
MacDonald et al(1991) Am J Hum Genet 49:723–34.
Mallinson et al(1995) Br J Haematol 90:823–9.
Marcus–Sekura(1988) Anal Bioche 172:289–95.
Morgenstern and Land(1990) Nucl Acid Res 18:3587–96.
Naylor et al(1996) Cell Genet 72:90–4.
Needles et al(1993)Proc Natl Aca Sci USA 90:10700–4.
Neote et al(1993) Cell 72:415–25.
Ohlmeyer et al(1993) Proc Natl Aca Sci USA 90:10922–6.
Page et al(1990) J Virol 64:5270–6.

(List continued on next page.)

*Primary Examiner*—Robert D. Budens
*Attorney, Agent, or Firm*—Klauber & Jackson

[57] ABSTRACT

Entry of HIV-1 into target cells requires cell surface CD4 as well as additional host cell cofactors. A cofactor required for infection with virus adapted for growth in transformed T cell lines was recently identified and named fusin. Fusin, however, does not promote entry of macrophage-tropic viruses that are believed to be the key pathogenic strains in vivo. It has now been determined that the principal cofactor for entry mediated by the envelope glycoproteins of primary macrophage-tropic strains of HIV-1 is CC-CKR5, a receptor for the β-chemokines RANTES, MIP-1α, and MIP-1β. It has also been found that individuals who are homozygous for a mutation of the CKR-5 receptor are resistent to HIV infection; in vitro infection requires a 1000-fold higher dose of HIV than normal cells. The mutation results in complete suppression of CKR-5 expression.

13 Claims, 18 Drawing Sheets

OTHER PUBLICATIONS

Pantaleo et al., N. Engl. J. Med. 332:209–216 (1995).
Paxton et al(1996) Nat Med 2:412–7.
Paxton et al(1993) J Virol 67:7229–37.
Raport et al., Gene 163:295–9 (1995).
Rowland–Jones et al(1995) Nat Med 1:59–64.
Samson et al(1996) Biochemistry 35:3362–7.
Samulski et al(1987) J Virol 61:3096–101.
Sattentau and Weiss, Cell 52:631–633 (1988).
Schall, Cytokine 3:165–183 (1991).
Scott and Smith(1990) Science 249:386–90.
Spira and Ho(1995) J Virol 69:422–9.
Stratford–Perricauder et al(1992) J Clin Invest 90:626–30.
Wilson et al. (1992) J. Biol. Chem. 267:963–7.
Wu et al(1992) J Biol Chem 267:963–7.

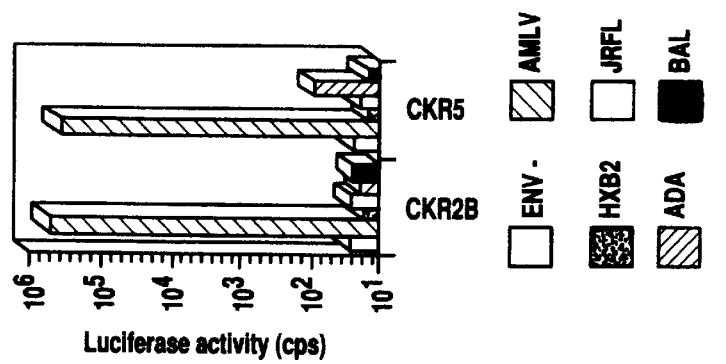
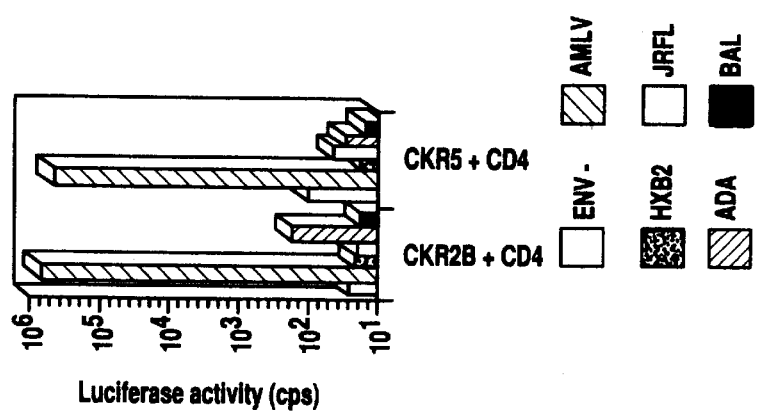
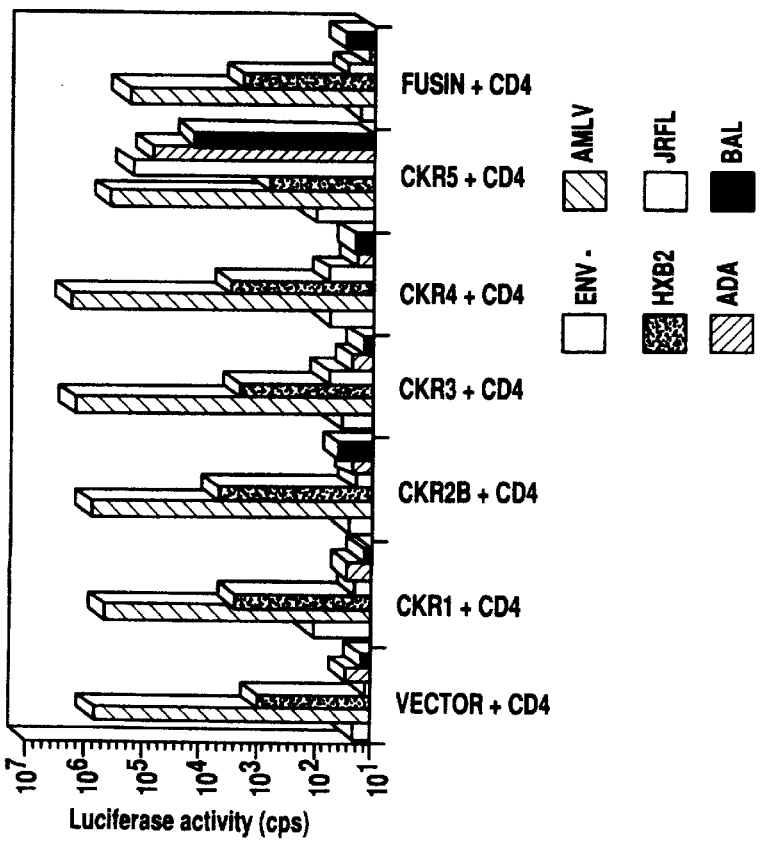

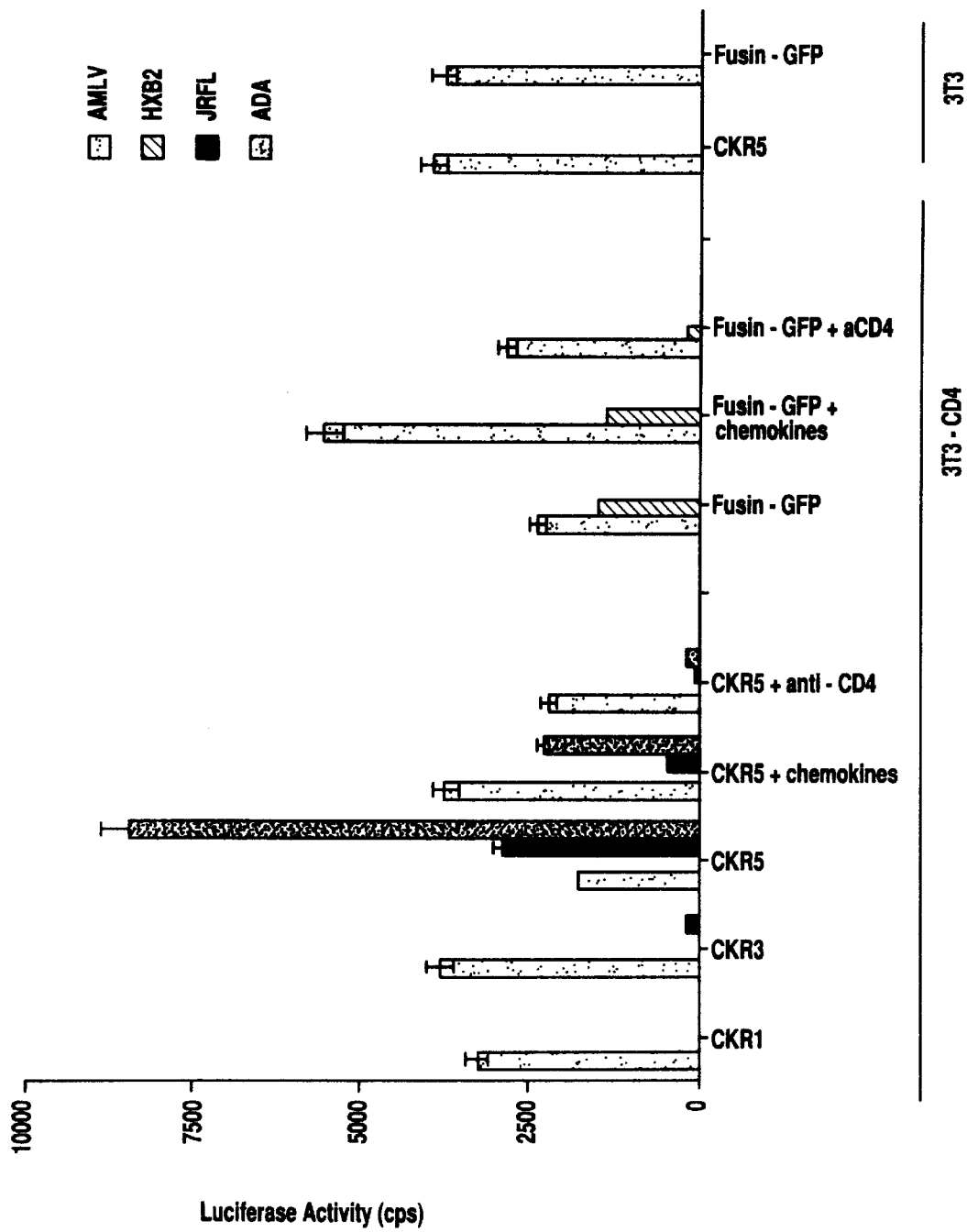

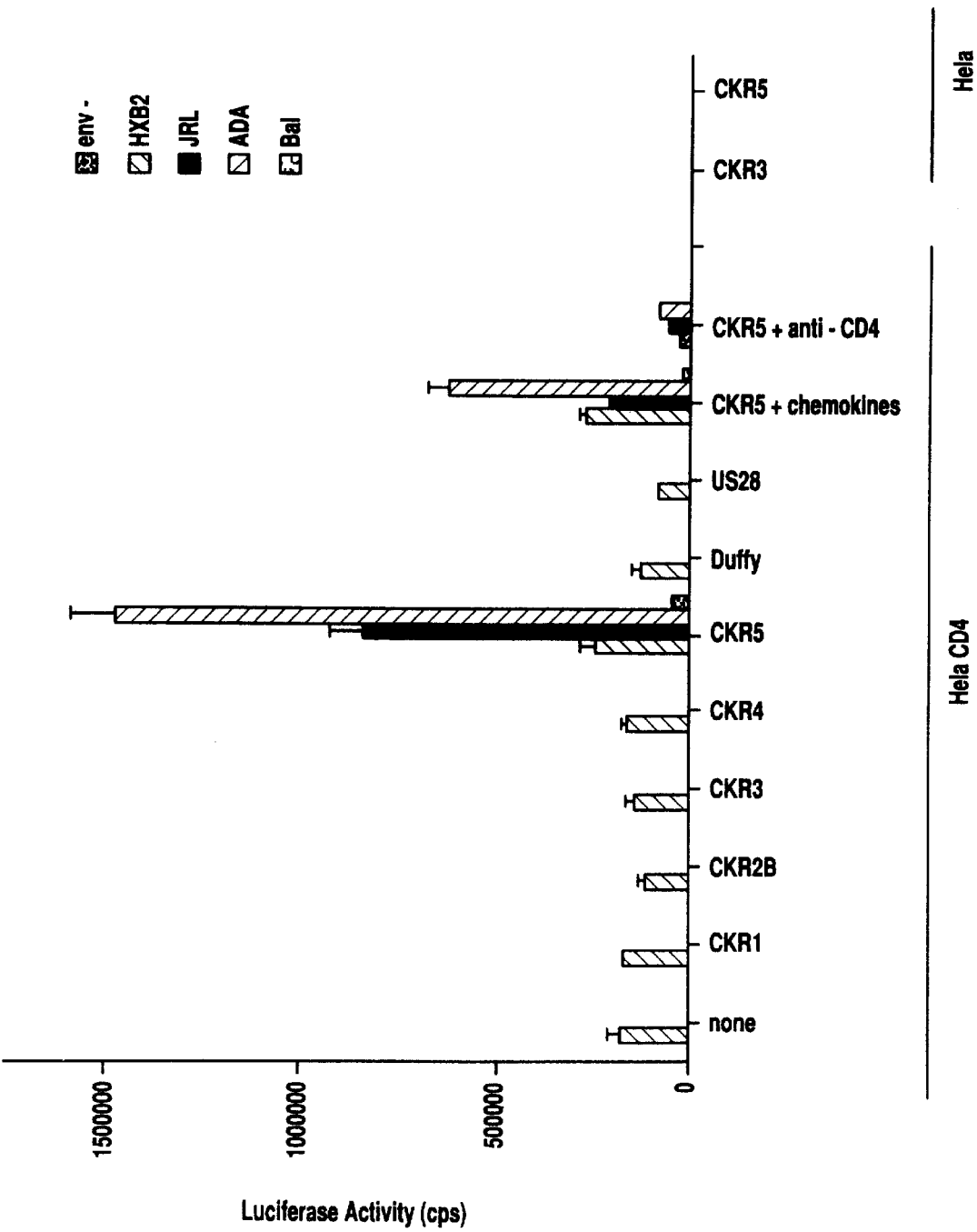

CKR5 - HXB2

CKR5 - JRFL

Fusin - HXB2

Fusin - JRFL

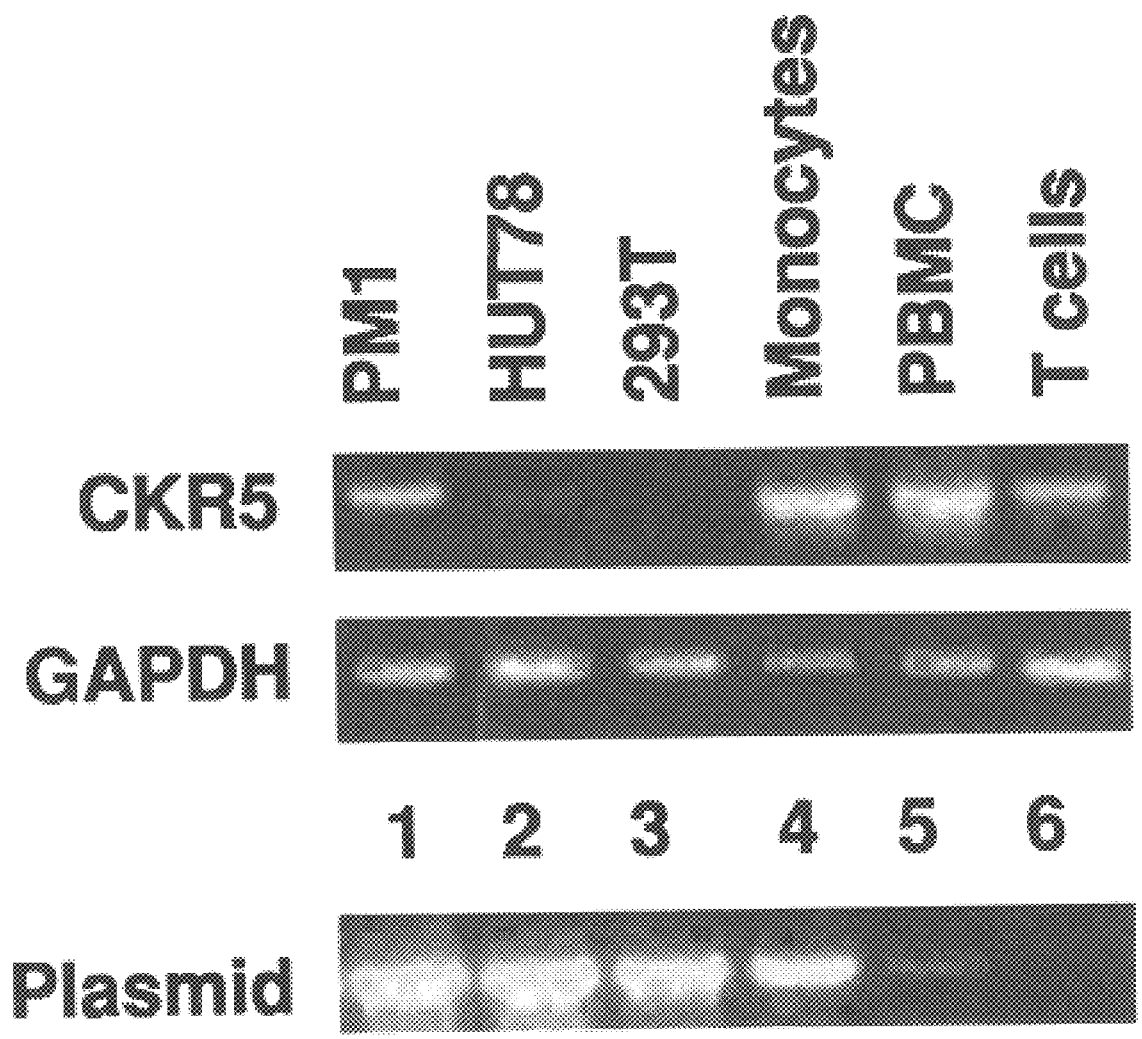

FIG. 7
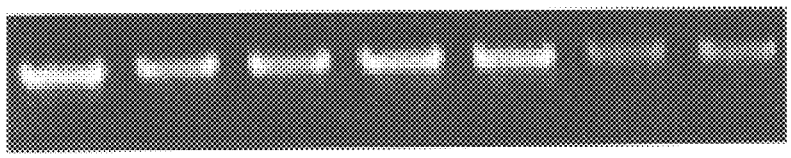
CKR - 5
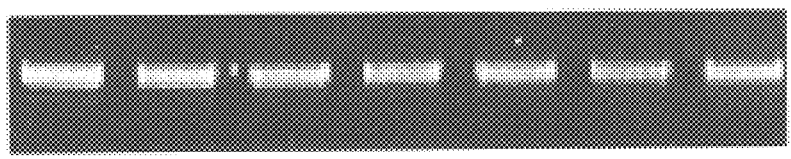
FUSIN
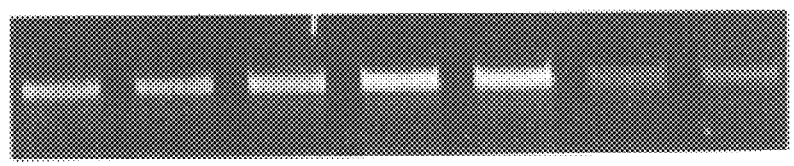
CKR - 1
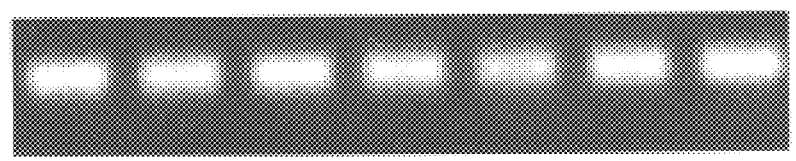
GAPDH
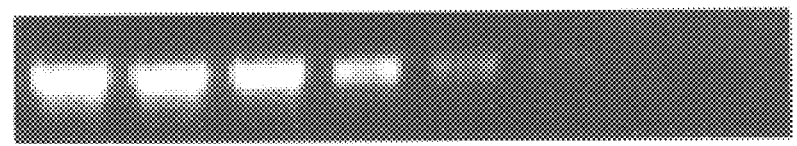
Plasmid

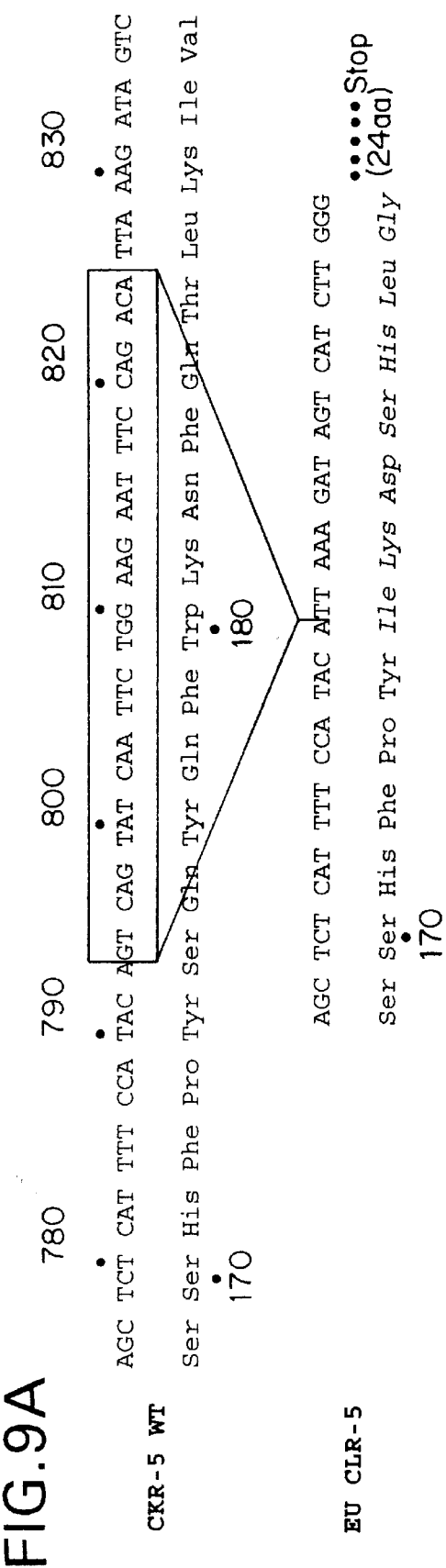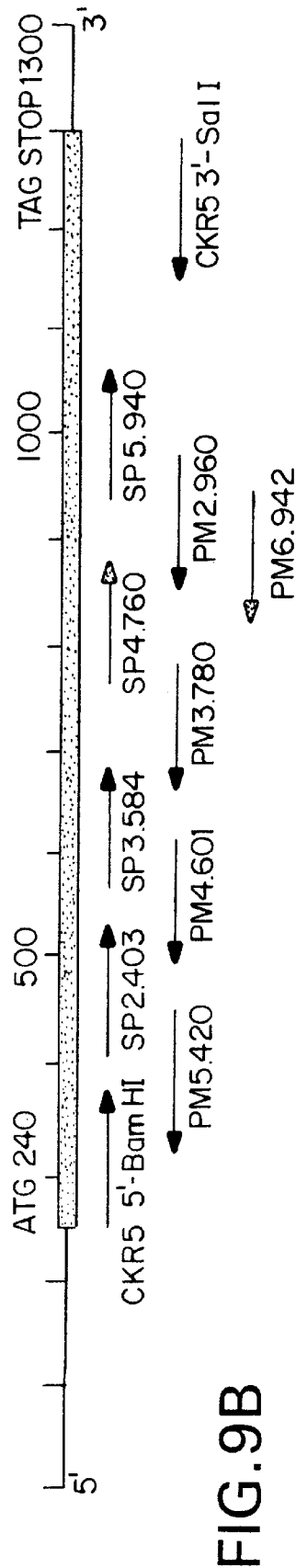

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
        (A) LENGTH: 32 base pairs
        (B) TYPE: nucleic acid
        (C) STRANDEDNESS: double
        (D) TOPOLOGY: linear (ii) MOLECULE TYPE: DNA (iii) HYPOTHETICAL: NO (xi) SEQUENCE DESCRIPTION: SEQ ID NO:1:

GTCAGTATCA ATTCTGGAAG AATTTCCAGA CA                                  32

(2) INFORMATION FOR SEQ ID NO:2:

(i) SEQUENCE CHARACTERISTICS:
        (A) LENGTH: 29 bases
        (B) TYPE: nucleic acid
        (C) STRANDEDNESS: single
        (D) TOPOLOGY: linear (ii) MOLECULE TYPE: DNA (iii) HYPOTHETICAL: NO (xi) SEQUENCE DESCRIPTION: SEQ ID NO:2:

GCGGATCCCA AAGTCCCTTG GAACCAGAG                                      29

(2) INFORMATION FOR SEQ ID NO:3:

(i) SEQUENCE CHARACTERISTICS:
        (A) LENGTH: 29 bases
        (B) TYPE: nucleic acid
        (C) STRANDEDNESS: single
        (D) TOPOLOGY: linear (ii) MOLECULE TYPE: DNA (iii) HYPOTHETICAL: NO (xi) SEQUENCE DESCRIPTION: SEQ ID NO:3:

GGTCTAGACA GGCCACCATT ACATTCCCT                                      29

(2) INFORMATION FOR SEQ ID NO:4:

(i) SEQUENCE CHARACTERISTICS:
        (A) LENGTH: 32 bases
        (B) TYPE: nucleic acid
        (C) STRANDEDNESS: single
        (D) TOPOLOGY: linear (ii) MOLECULE TYPE: DNA (iii) HYPOTHETICAL: NO (xi) SEQUENCE DESCRIPTION: SEQ ID NO:4:

GGCTAAAGCT TGGCCTGAGT GCTCCAGTAG CC                                  32

```
(2) INFORMATION FOR SEQ ID NO:5:

(i) SEQUENCE CHARACTERISTICS:
        (A) LENGTH: 30 bases
        (B) TYPE: nucleic acid
        (C) STRANDEDNESS: single
        (D) TOPOLOGY: linear (ii) MOLECULE TYPE: DNA (iii) HYPOTHETICAL: NO (xi) SEQUENCE DESCRIPTION: SEQ ID NO:5:

CGTCCTCGAG CATCTGTGTT AGCTGGAGTG                                        30

(2) INFORMATION FOR SEQ ID NO:6:

(i) SEQUENCE CHARACTERISTICS:
        (A) LENGTH: 29 bases
        (B) TYPE: nucleic acid
        (C) STRANDEDNESS: single
        (D) TOPOLOGY: linear (ii) MOLECULE TYPE: DNA (iii) HYPOTHETICAL: NO (xi) SEQUENCE DESCRIPTION: SEQ ID NO:6:

CTCGGATCCG GTGGAACAAG ATGGATTAT                                         29

(2) INFORMATION FOR SEQ ID NO:7:

(i) SEQUENCE CHARACTERISTICS:
        (A) LENGTH: 28 bases
        (B) TYPE: nucleic acid
        (C) STRANDEDNESS: single
        (D) TOPOLOGY: linear (ii) MOLECULE TYPE: DNA (iii) HYPOTHETICAL: NO (xi) SEQUENCE DESCRIPTION: SEQ ID NO:7:

CTCGTCGACA TGTGCACAAC TCTGACTG                                          28

(2) INFORMATION FOR SEQ ID NO:8:

(i) SEQUENCE CHARACTERISTICS:
        (A) LENGTH: 21 bases
        (B) TYPE: nucleic acid
        (C) STRANDEDNESS: single
        (D) TOPOLOGY: linear (ii) MOLECULE TYPE: DNA (iii) HYPOTHETICAL: NO (xi) SEQUENCE DESCRIPTION: SEQ ID NO:8:

CTTCATTACA CCTGCAGCTC T                                                 21

(2) INFORMATION FOR SEQ ID NO:9:

(i) SEQUENCE CHARACTERISTICS:
        (A) LENGTH: 22 bases
        (B) TYPE: nucleic acid
        (C) STRANDEDNESS: single
        (D) TOPOLOGY: linear
```

(ii) MOLECULE TYPE: DNA (iii) HYPOTHETICAL: NO (xi) SEQUENCE DESCRIPTION: SEQ ID NO:9:

CACAGCCCTG TGCCTCTTCT TC                                              22

(2) INFORMATION FOR SEQ ID NO:10:

(i) SEQUENCE CHARACTERISTICS:
            (A) LENGTH: 63 base pairs
            (B) TYPE: nucleic acid
            (C) STRANDEDNESS: double
            (D) TOPOLOGY: linear (ii) MOLECULE TYPE: DNA (iii) HYPOTHETICAL: NO (xi) SEQUENCE DESCRIPTION: SEQ ID NO:10:

AGCTCTCATT TTCCATACAG TCAGTATCAA TTCTGGAAGA ATTTCCAGAC ATTAAAGATA     60

GTC                                                                   63

(2) INFORMATION FOR SEQ ID NO:11:

(i) SEQUENCE CHARACTERISTICS:
            (A) LENGTH: 21 amino acids
            (B) TYPE: amino acid
            (C) STRANDEDNESS: single
            (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:11:

Ser Ser His Phe Pro Tyr Ser Gln Tyr Gln Phe Trp Lys Asn Phe Gln
1               5                   10                  15

Thr Leu Lys Ile Val
            20

(2) INFORMATION FOR SEQ ID NO:12:

(i) SEQUENCE CHARACTERISTICS:
            (A) LENGTH: 39 base pairs
            (B) TYPE: nucleic acid
            (C) STRANDEDNESS: double
            (D) TOPOLOGY: linear (ii) MOLECULE TYPE: DNA (iii) HYPOTHETICAL: NO (xi) SEQUENCE DESCRIPTION: SEQ ID NO:12:

AGCTCTCATT TTCCATACAT TAAAGATAGT CATCTTGGG                            39

(2) INFORMATION FOR SEQ ID NO:13:

(i) SEQUENCE CHARACTERISTICS:
            (A) LENGTH: 13 amino acids
            (B) TYPE: amino acid
            (C) STRANDEDNESS: single
            (D) TOPOLOGY: linear -continued

```
    (ii) MOLECULE TYPE: peptide (iii) HYPOTHETICAL: NO (v) FRAGMENT TYPE: internal (xi) SEQUENCE DESCRIPTION: SEQ ID NO:13:

Ser Ser His Phe Pro Tyr Ile Lys Asp Ser His Leu Gly
1               5                  10
```

HIV CORECEPTOR MUTANTS

CROSS REFERENCE TO RELATED APPLICATIONS

The present Application is a non-provisional application claiming the priority of coepending provisional U.S. Ser. No. 60/025,230, filed Aug. 8, 1996. Applicants claim the benefits of this Application under 35 U.S.C. §119(e).

GOVERNMENT SUPPORT

The research leading to the present invention was supported, in part, by grants from the National Institutes of Health, Grant Nos. R01CA72149, R29AI36057, RO1AI35522, RO1AI38573, and NO1AI45218. Accordingly, the United States government may have certain rights in the invention.

FIELD OF THE INVENTION

The present invention relates generally to the infection of target cells by HWV-1, and more particularly to agents identified herein that mediate the entry of macrophage-trophic HIV into such target cells, and to the diagnostic and therapeutic uses to which such agents may be put. The invention further relates to identification of a mutation in an HIV coreceptor that is protective against HIV infection.

BACKGROUND OF THE INVENTION

The human immunodeficiency viruses infect $CD4^+$ macrophages and T helper cells. Although HIV-1 entry requires cell surface expression of CD4, to which the viral envelope glycoproteins bind, several studies have suggested that it is not sufficient for fusion of the viral envelope to the cellular plasma membrane. Early studies have shown that while human cells expressing a transfected CD4 gene were permissive for virus entry, murine cells expressing human CD4 were not. These findings led to the suggestion that there is a species-specific cell surface cofactor required in addition to CD4 for HIV-1 entry. Subsequent studies have shown that strains of HIV-1 that had been adapted for growth in transformed T-cell lines (T-tropic strains) could not infect primary monocytes or macrophages; in contrast, primary viral strains were found to infect monocytes and macrophages, but not transformed T cell lines. This difference in tropism was found to be a consequence of specific sequence differences in the gp120 subunit of the envelope glycoprotein, suggesting that multiple cell type-specific cofactors may be required for entry in addition to CD4.

The vast majority of people are susceptible to infection with HIV-1. However, rare individuals have been described that appear to remain uninfected by HIV-1 despite histories of multiple high-risk sexual exposures to the virus [Clerici et al., J. Infect. Dis. 165: 1012–1019 (1992); Langlade-Demoyen et al., J. Clin. Invest. 93: 1293–1297 (1994); Paxton et al., 1996, supra; Rowland-Jones et al., Nat. Med. 1: 59–64 (1995)]. In some cases this may simply be stochastic, or may be due to an extremely quiescent infection.

HIV-1 can broadly be divided into macrophage- or T-tropic isolates [Fisher et al., Nature 334: 444–447 (1988); Gartner et al., Science 233: 215–219 (1986)]; Koyanagi et al., Science 236: 819–822 (1987)]. Macrophage-tropic nonsyncytium-inducing (NSI) isolates infect primary macrophages but fail to infect transformed T-cell lines, while T-tropic syncytium-inducing (SI) strains have the reciprocal tropism. Both classes of HIV-1 efficiently infect $CD4^+$ T-cells isolated from peripheral blood mononuclear cells (PBMC). Macrophage-tropic NSI viruses appear to be preferentially transmitted by sexual contact and constitute the vast majority of virus present in newly infected individuals [Zhu et al., Science 261: 1179–1181 (1993)]. The T-tropic SI viruses generally appear late in the course of infection during the so called "phenotypic switch" that often precedes the onset of AIDS symptoms [Connor and Ho, J. Virol., 68: 440–4408 (1994); Schuitemaker et al., J. Virol. 66, 1354–60 (1992)].

HIV-1 replication is initiated by attachment of the virus to the cell surface via high affinity binding of the envelope glycoprotein (Env) to CD4 on the cell surface [reviewed by [Sattentau and Weiss, Cell 52: 631–633 (1988)]. Subsequently, the viral envelope fuses to the cell membrane, depositing the viral core in the cytoplasm. The nature of the cofactors required for HIV entry proved elusive until the identification of specific receptor protein. The fusion reaction is mediated by newly-described seven transmembrane domain G protein-coupled molecules termed coreceptors [Alkhatib et al., Science 272: 1955–1958 (1996); Choe et al., Cell 85: 1135–1148 (1996); Deng et al., Nature, 381: 661–666 (1996); Doranz et al., Cell, 85: 1149–1158 (1996); Dragic et al., Nature 381: 667–673 (1996); Feng et al., Science 272: 872–877 (1996)]. The molecular basis of HIV-1 tropism appears to lie in the ability of Envs from macrophage-tropic and T-tropic viruses to interact with different coreceptors. T-tropic viruses tend to use fusin, a previously identified seven transmembrane protein related to the IL-8 receptor [Feng et al., 1996, supra]. Macrophage-tropic viruses primarily use CKR-5 (for C—C chemokine receptor-5), a seven transmembrane domain chemokine receptor [U.S. patent application Ser. No. 08/650,412 and Provisional Ser. No. 60/017,157, both filed May 20, 1996; and Ser. No. 08/666,020, and Provisional Ser. No. 60/020, 043; Alkhatib et al., 1996, supra; Choe et al., 1996, supra; Deng et al., 1996, supra; Doranz et al., 1996, supra; Dragic et al., 1996, supra; Feng et al., 1996, supra]. Use of other chemokine receptors such as CKR-2B and CKR-3 by a minority of viruses has also been reported (Choe et al., 1996, supra; Doranz et al., 1996, supra).

Physiologically, chemokine receptors mediate the chemotaxis of T-cells and phagocytic cells to areas of inflammation [reviewed by Horuk, Trends Pharmacol. Sci. 15: 159–65 (1994)]. Upon ligand binding, the receptors transduce an intracellular signal that results in the rapid mobilization of intracellular calcium. Each of the eight known chemokine receptors is a G protein-coupled seven transmembrane domain protein with a characteristic pattern of ligand binding [reviewed by Schall, Cytokine 3: 165–183 (1991)]. CKR-5, which also serves as a major coreceptor for macrophage-tropic HIV-1, binds the β-chemokines RANTES (regulated on activation, normal T expressed and secreted), MIP-1α (macrophage inflammatory protein) and MIP-10β [Samson et al., 1996, supra]. The ligand for fusin has not yet been identified. High levels of RANTES, MIP-1α or MIP-1β prevent replication of macrophage-tropic, but not T-tropic strains of HIV-1 [Cocchi et al., Science 720: 1811–1815 (1996)]. This inhibition is due to the binding of chemokines to CKR-5, resulting in a block to viral entry and fusion [Deng et al., 1996, supra; Dragic et al., 1996, supra]. The precise mechanism of this interference is unknown.

The nature of the cofactors required for HIV entry proved elusive until the recent identification by Feng et al. [Science 272, 872–877 (1996)] of fusin, a member of the seven transmembrane G-protein coupled receptor family. Fusin was shown to act as a co-receptor for T-tropic strains;

however, it did not support infection of CD4⁺ cells by macrophage-tropic viruses, which more closely resemble those that predominate in infected individuals throughout the course of the disease, particularly in the asymptomatic phase. In addition, these strains appear to be responsible for HIV-1 transmission, both sexually and by transfer of infected blood. Rare individuals who are resistant to sexual transmission of HIV-1 have T-cells that are readily infected by T-tropic virus, but cannot be infected by macrophage-tropic virus, further supporting a role for macrophage-tropic virus in sexual transmission of HIV-1.

Cocchi et al. recently characterized inhibitors of HIV-1 replication present in supernatants of CD8⁺ T cells as the β-chemokines RANTES, MIP-1α and MIP-1β [Cocchi et al., (1996), supra]. Chemokines are chemotactic cytokines that are released by a wide variety of cells to attract macrophages, T cells, eosinophils, basophils and neutrophils to sites of inflammation (reviewed in ref. 14). The chemokines fall into two classes, C-X-C (α) and C—C (β), depending on whether the first two cysteines are separated by a single amino acid or are adjacent. The α-chemokines such as IL-8, NAP-2 and MGSA are chemotactic primarily for neutrophils, while β-chemokines such as RANTES, MIP-1α, MIP-1β, MCP-1, MCP-2, and MCP-3 are chemotactic for macrophages, T-cells, eosinophils and basophils. The chemokines bind specific cell surface receptors belonging to the family of G protein-coupled seven transmembrane domain proteins (reviewed in Ref. 15). Upon binding their cognate ligands, chemokine receptors transduce an intracellular signal through the associated trimeric G protein. This results in a rapid increase in intracellular calcium concentration. There are at least seven human chemokine receptors that bind or respond to β-chemokines with the following characteristic pattern: CC-CKR-1 (MIP-1α, MIP-1β, MCP-3, RANTES), CC-CKR-2A and CC-CKR-2B (MCP-1, MCP-3), CC-CKR-3 (eotaxin, RANTES, MCP-3), CC-CKR4 (MIP-1α, RANTES, MCP-1), CC-CKR-5 (MIP-α, RANTES, MIP-1β), and the Duffy blood group antigen (RANTES, MCP-1).

The cellular factors that account for the inability of macrophage-tropic HIV-1 to enter EU cells have not been elucidated. Importantly, the CD4⁺ T-cells of EU2 and EU3, while resistant to infection by macrophage-tropic virus, are readily infected by T-tropic HIV-1 [Paxton et al., 1996, supra]. Thus, the EU cells do not have a generalized inability to support virus replication. Presumably, they either lack a specific factor that is required for entry of macrophage-tropic HIV-1 or contain an inhibitor of this step of virus replication. T-cell clones derived from the PBMC of one of these individuals (EU2) generally secreted about 10-fold more β-chemokine than similar clones derived from control individuals [Dragic et al., 1996, supra]. Thus, the resistance of these cells to HIV-1 infection could be caused by autocrine or paracrine blocking of CKR-5 coreceptor activity by the high levels of endogenous chemokines. Alternatively, genetic alteration of CKR-5 itself could decrease its ability to mediate viral entry.

Thus, there is a need in the art to understand the molecular mechanisms for resistance to macrophage-tropic HIV infection.

More particularly, there is a need in the art to identify the molecular basis for resistance to CKR-5 coreceptor-mediated HIV infection.

There is a further need in the art to distinguish autocrine or paracrine blocking of CKR-5 coreceptor activity from defective CKR-5.

These and other needs in the art are addressed by the present invention, as described below.

The citation of any reference herein should not be deemed as an admission that such reference is available as prior art to the application.

SUMMARY OF THE INVENTION

In its broadest aspect, the present invention relates to the identification and application of an agent capable of promoting the translocation of macrophage-tropic HIV through the membrane of a target CD4⁺ cell, termed herein a coreceptor. A coreceptor of the invention is a chemokine receptor, which exhibits certain of the following characteristics and activities:

A. It is present in, on, or proximal to the cell membrane of the target $CD4^+$ cell;

B. It acts in tandem with CD4, in connection with the translocation; and

C. It is capable of interacting with associated G-proteins to thereby transduce an intracellular signal. A further characteristic attendant to the activity of the translocation promoting agent of the present invention is an observed increase in the concentration of intracellular calcium. The present agent may also be described as a mediator of the entry of envelope glycoproteins of macrophage-tropic strains of HIV-1 into target cells.

The present coreceptor (translocation promoting agent) appears to act as a co-factor that collaborates with CD4 in facilitating the penetration of the macrophage-tropic virus into the target cell to establish HIV infection. A particular family of receptors known as C—C (or β) chemokine receptors (CKRs) has been identified as defining certain of the activities and characteristics set forth above, and a specific such receptor, CC-CKR5, is exemplified herein.

Other analogous receptors, such as those encoded by some viruses, particularly members of the Herpes virus family (CMV, HHV-6, HHV-8), serve to broaden the host range of HIV in individuals infected with both HIV and these viruses.

This may therefore increase the range of tissues infected or provide a ligand for HIV envelope that may result in deleterious signal transduction in various tissues. Such information could lead to novel approaches to block the synergy between HIV and viral cofactors.

In particular, the present invention is directed to a method for identifying an individual who may be resistant to human immunodeficiency virus-1 (HIV-1) infection. The invention is based, in part, on identification of exposed but uninfected individuals who are homozygous for a mutation in the CKR-5 gene. Accordingly, the method comprises identifying whether an individual is homozygous, heterozygous, or normal for a mutation of a CKR-5 gene resulting in lack of expression of a functional CKR-5 chemokine receptor protein. Heterozygosity for a CKR-5 ± mutation indicates that the individual may be more resistant to HIV infection than normals, and homozygosity for a CKR-5 −/− mutation indicates that the individual may be more resistant than normals or than heterozygous individuals. In a specific embodiment, the individual is identified as heterozygous CKR-5 ±, and the resistance to HIV infection manifests as a reduced decline slope of CD4+ cells. In another specific embodiment, the individual is identified as homozygous CKR-5 −/−, and the resistance to HIV infection manifests as remaining uninfected despite multiple high exposure to HIV.

In the Examples, infra, heterozygous subjects have a decline slope of CD4+ cells of −10 per year, while normals have a decline slope of −90 to −100 per year. Furthermore, as noted above, two homozygous mutant individual were resistant to HIV, as evidence by maintaining uninfected status as determined by sero-testing and sensitive PCR testing for HIV, despite repeated exposure to the virus via sexual contact with one or more infected individuals.

In a specific aspect, the mutation of the CKR-5 gene results in a frameshift that encodes a severely truncated CKR-5 protein that is not detectable at the cell surface or in the cytoplasm. More specifically, the mutation is a 32 base-pair deletion spanning nucleotides 794 to 825 in a region of the CKR-5 gene corresponding to the second extracellular loop.

The mutation may be detected by polymerase chain amplification (PCR) analysis, or by Southern analysis. PCR analysis of mRNA (reverse transcriptase, RT, PCR) requires that the mRNA be obtained from cells expected to express CKR-5, e.g., macrophages, T cells, etc. cDNA, e.g., in a cDNA library, from these cells can also be analyzed. Genomic DNA can be obtained from any source.

A number of specific methodologies exist for detecting the mutation by PCR analysis. These include differentiation of the mutant and normal extracellular loop can be differentiated by specific restriction endonucleases. In a specific embodiment, exemplified infra, the PCR analysis is performed by: amplifying the complete CKR-5 mRNA, cDNA, or genomic DNA using a 5' primer GCGGATC-CCAAAGTCCCTTGGAACCAGAG (SEQ ID NO:2) and a 3' primer GGTCTAGACAGGCCACCATTACATTCCCT (SEQ ID NO:3); and detecting the presence of the 32-base pair deletion. The deletion can be detected by sequencing the amplified region, wherein the sequence of the PCR product amplified from the mutant has a 32-base pair deletion, or by determining the size of the PCR products by electrophoresis, and comparing the size of the PCR product to the size of the PCR product from a wild-type CKR-5 gene, wherein the size of the PCR product from the mutant is about 32 base pairs smaller than the wild-type PCR product. Alternatively, and more preferably, the PCR analysis is performed by amplifying the portion of CKR-5 mRNA, cDNA, or genomic DNA flanking the deletion site using a SP4.760 5' primer CTTCATTACACCTGCAGCTCT (SEQ ID NO:8) and a PM6.942 3' primer CACAGCCCTGTGCCTCTTCTTC (SEQ ID NO:9); and detecting the presence of the 32-base pair deletion. The mutation may be detected by sequencing the amplified region, wherein the sequence of the PCR product amplified from the mutant has a 32-base pair deletion; or by determining the size of the PCR products by electrophoresis, wherein the PCR product from a wild-type CKR-5 gene is about 182 base pairs, and the PCR product from a mutant CKR-5 gene is about 150 base pairs.

Southern analysis can be performed by cleaving genomic DNA with restriction enzyme and separating it by electrophoresis on an agarose gel; transferring the separated DNA to a nitrocellulose filter and hybridizing with a labeled CKR-5 specific probe; and detecting a difference in the size of restriction fragments hybridized by the probe compared to the size from a wild-type individual. Detection of a restriction fragment that is approximately 32 base pairs smaller than wild-type is indicative of the mutation. In a specific embodiment, exemplified infra, the restriction enzymes are EcoRI and BglII, the probe is a BamHI-SalI cleaved CKR-5 cDNA insert labeled with [$\alpha$-$^{32}$P]dCTP, and the wild-type fragment is 283 base pairs and the mutant is 251 base pairs.

In another aspect of the invention, specific oligonucleotide probes can be used to detect the mutation or lack of the mutation in samples of mRNA, cDNA, or genomic DNA. The probes are designed to hybridize only to a nucleic acid (mRNA, cDNA, or genomic DNA, or PCR amplified fragment thereof) that includes or lacks the 32 base pair deleted sequence. Thus, in one embodiment, the invention provides a method for identifying a homozygous CRK-5 −/− individual. In this embodiment, the mutation is detected by detecting hybridization of an oligonucleotide probe corresponding to the 32 base pair deletion with a sample from the individual selected from the group consisting of mRNA (Northern analysis), cDNA, and genomic DNA (Southern analysis), wherein hybridization of the probe to the sample indicates that the individual is not homozygous CKR-5 −/−. Another embodiment is directed to a method for identifying a homozygous CRK-5 −/− or heterozygous CKR-5 ± individual, wherein the mutation is detected by detecting hybridization of a first oligonucleotide probe corresponding to the CKR-5 sequence with the 32 base pair deletion with a sample from the individual selected from the group consisting of mRNA (Northern analysis), cDNA, and genomic DNA (Southern analysis); hybridization of the probe to the sample indicates that the individual is homozygous CKR-5 −/− or heterozygous CKR-5 ±. In a further aspect of this other embodiment, hybridization of a second oligonucleotide probe corresponding to the 32 base pair deletion is detected. In this aspect, hybridization of the first probe but not the second probe indicates that the individual is homozygous CKR-5 −/−; hybridization of the first and second probes indicates that the individual is heterozygous CKR-5 ±; and hybridization of second probe but not the first probe indicates that the individual is wild type.

In addition to the foregoing methods, the invention provides corresponding nucleic acids, e.g., to prepare recombinant cells for testing the role of CKR-5, or other chemokine receptors, in HIV-1 infection in vitro or in a transgenic animal model in vivo. Thus, in one aspect the invention provides an isolated nucleic acid comprising the CKR-5 gene having a 32 base-pair deletion spanning nucleotides 794 to 825 in a region of the CKR-5 gene corresponding to the second extracellular loop. In a further embodiment, the invention provides an expression vector comprising cDNA or genomic DNA corresponding to the mutated form of the CRK-5 gene operably associated with an expression control sequence. The invention further provides a host cell transfected or transformed with the expression vector, wherein the host cell endogenously expresses human CD4, has been modified to express human CD4, or is subsequently modified to express human CD4. In a further aspect, the host cell is in a transgenic animal.

The invention also provides nucleic acids for use in the methods of the invention, such as specific PCR primers or hybridization probes. For example, the full length mutant gene can be used as a hybridization probe. More preferably, the invention provides a labeled oligonucleotide corresponding to the deleted 32 base pair sequence, having a nucleotide sequence GTCAGTATCAATTCTGGAAGAATTTCCA-GACA (SEQ ID NO:1) or a sequence complementary to SEQ ID NO:1. This probe can be used to detect wild type nucleic acids, e.g., in the practice of the method described above. In another embodiment, a labeled oligonucleotide hybridizable under stringent conditions to a nucleic acid having the sequence AGCTCTCATTTTCCATACATTAAA-GATAGTCATCTTGGG (SEQ ID NO:12) or a sequence complementary to SEQ ID NO:12 is provided. This oligonucleotide is useful to detect nucleic acids encoding the mutant form of the protein. Both probes together provide for identification of wild type CKR-5 +/+, heterozygous CKR-5 ±, or homozygous CKR-5 −/−.

More generally, the invention also relates to an isolated nucleic acid, such as DNA, or a truncated or degenerate variant thereof, which encodes an HIV coreceptor, or the active portion thereof, preferably a nucleic acid molecule, in particular a recombinant DNA molecule or cloned gene. In another embodiment, the human and murine DNA sequences of the coreceptor translocation promoting agent of the present invention, or portions thereof, may be prepared as probes to screen for complementary sequences and genomic clones in the same or alternate species. The present invention extends to probes so prepared that may be provided for screening cDNA and genomic libraries for mutations of the coreceptor translocation promoting agent. For example, the probes may be prepared with a variety of known vectors, such as the phage λ vector. The present invention also includes the preparation of plasmids including such vectors, and the use of the DNA sequences to construct vectors expressing antisense RNA or ribozymes which would attack the mRNAs of any or all of the DNA sequences so prepared or constituted. Correspondingly, the preparation of antisense RNA and ribozymes are included herein.

The present invention also includes animal models. In one aspect of the invention a non-human animal model is used in the study of HIV infection and HIV disease in order to develop modes of diagnosis, prevention, treatment and/or cures. In some embodiments, a transgenic animal is produced containing the CD4 enhancer/promoter/silencer as described by Killeen et al., [The EMBO J. 12, 1547–1553 (1993)]. In one such embodiment, a transgenic animal has a translocating promoter regulated by the CD4 enhancer/promoter/silencer. More particularly, the regulation of the translocating promoter may include the CD4 enhancer/promoter/silencer plus a macrophage-specific enhancer. Yet further, the macrophage-specific enhancer can be all or a functional portion of the first intron of the human CD4 gene. In a specific embodiment, related to the disclosure above, a mutant chemokine receptor that does not express a functional protein can be introduced in an animal model to evaluate the ability of HIV isolates to infect cells in vivo.

In a further aspect of the invention, a transgenic non-human animal is produced with the gene for the animal homolog of the translocating promoter replaced by its human counterpart. In this embodiment, the translocating promoter may be selected from CC-CKR-5, fusin, CC-CKR-2B and CC-CKR-3. In a preferred embodiment the translocating promoter is CC-CKR-5.

In a variant embodiment, a transgenic animal is produced with the genes for two such animal homologs of two translocating promoters replaced by their human counterparts. In one such specific embodiment, one of the translocating promoters is CC-CKR-5 and the other is fusin. In other embodiments more than two such animal homologs -are replaced by their human counterparts. In a more preferred embodiment, the transgenic animal also contains human CD4.

In a more generalized application of this aspect of the invention the replacement of the animal homolog gene is performed in the animal germ line, preferably as a "knockin" as generally described in Hanks et al., [Science 269, 679–682 (1995)]. A more focussed construct is be prepared by the replacement of the gene in T-cells and macrophages. In variant preparations, human CD4 may also be present in the animal T-cells and/or macrophages. A particular replacement gene that may be used comprises a nucleic acid that encodes the human coreceptor (translocating promoter) expressed under the control of a gene naturally expressed in macrophages and/or T-Cells, e.g. lysozyme. In a specific embodiment, the human translocating promoter placed between the 5' end and the 3' prime end of the lysozyme gene is CC-CKR-5.

The non-human animal prepared in accordance herewith may be any animal that is amenable to transgenic technology. In a preferred embodiment the non-human animal is selected from the group consisting of a mouse, a rat, a rabbit, a sheep, a goat, a pig and a primate.

In a related aspect, the mutability of retroviruses in general, and specifically HIV-1, is consistent with the identity of the translocating promoter agent changing as the viral infection progresses. Such changes are due to changes in HIV that lead to the emergence and activity of different coreceptors (translocating promoter agents) in different populations (e.g. geographically separated groups of people.) Furthermore, changes in the virus and its choice of coreceptor (translocating promoter agent) can be indicative of different stages of the infection in an infected individual. Information regarding the progression of the infection is extremely valuable to that individual and his health care provider, e.g., such as in the treatment of that individual.

The present invention includes a method of monitoring the progression of the HIV infection by determining shifts in the identity of the coreceptor (translocating promoter agent) as the infection progresses. The method includes the use of the assorted cell lines disclosed herein (and others prepared in the same manner) which express the different β-chemokine receptors along with CD4.

The first step entails quantifying the amounts of the particular translocating promoter agents that are utilized by the virus during the specific stages of the infection, in a relevant population of HIV-1 infected people. A proportional relationship between these quantified amounts may then be correlated with the specific stages of HIV-1 infection. The second step is to quantify the amounts of the particular translocating promoter agents that are utilized by the virus in a biological sample obtained from an infected individual. The third step is to correlate the proportions determined for the individual with those determined for the group and thereby determine the stage of the HIV-1 infection for the individual.

Efficiency of HIV infection for a given amount of each β-chemokine receptor used as a coreceptor (translocating promoter agent) by HIV-1 in a given biological sample can be determined with the assorted cell lines disclosed herein. These cell lines express different β-chemokine receptors along with CD4 and may be detectably labeled so as to allow their relative sensitivity to the virus be determined. Gene does effect can also be evaluated by regulating the level of expression of the β-chemokine receptor. Only the HIV-1 strain that uses the particular β-chemokine as the translocating promoter agent, can successfully infect a test cell with that particular β-chemokine. The efficiency of infection depends, at least in part, on the amount of receptor available. A label inside the cell that is activated by successful infection will allow quantitation of the amount of the particular β-chemokine. Detectable labels may be linked to genetic markers that are only expressed upon HIV-1 infection. Appropriate detectable labels include luciferase and others described herein.

The invention also includes an assay system for screening of potential drugs effective to modulate translocation of macrophage-trophic HIV into target mammalian cells by interrupting or potentiating the coreceptor (translocation promoting agent). In one instance, the test drug could be administered to a cellular sample with the ligand that activates the coreceptor (translocation promoting agent), or an extract containing the activated coreceptor (translocation promoting agent), to determine its effect upon the binding activity of the coreceptor (translocation promoting agent) to any chemical sample (including DNA), or to the test drug, by comparison with a control.

The assay system could more importantly, be adapted to identify drugs or other entities that are capable of binding to the coreceptor (translocation promoting agent) and/or to corresponding factors or proteins, thereby inhibiting or potentiating translocation promoting agent activity. Such assay would be useful in the development of drugs that would be specific against particular cellular activity, or that would potentiate such activity, in time or in level of activity. For example, such drugs might be used to inhibit penetration of HIV into the target cell.

In yet a further embodiment, the invention contemplates the identification and use of antagonists of the activity of a translocation promoting agent. In particular, an agent or molecule that inhibits the HIV-translocating activity of the tranlocation promoting agent. In a specific embodiment, the antagonist can be a peptide having the sequence of a portion of the active domain of the translocation promoting agent, which may competitively inhibit HIV binding to the coreceptor.

The present invention extends to assays to screen for drugs and small molecules that would function as inhibitors of HIV translocation. A particular such assay may be constituted about a transgenic non-human mammal that comprises a DNA construct containing a human CD4 gene and a DNA construct containing human CC-CKR-5 gene, wherein both CD4 protein and CC-CKR-5 protein are expressed by said non-human mammal.

The present invention likewise extends to the development of antibodies to the coreceptor (translocation promoting agent(s)), including naturally raised and recombinantly prepared antibodies. Antibodies can be used for various purposes including to evaluate the relative resistance or permissiveness of $CD4^+$ cells to HIV infection to block HIV translocation, and to identify such proteins that function as macrophage-tropic HIV translocation receptors. For example, the antibodies could be used to screen expression libraries to obtain the gene or genes that encode the translocation promoting agent(s) Such antibodies could include both polyclonal and monoclonal antibodies prepared by known genetic techniques, as well as bi-specific (chimeric) antibodies, and antibodies including other functionalities suiting them for additional diagnostic use conjunctive with their capability of modulating translocation promoting agent activity. Preferably, an antibody of the invention specifically binds to CC-CKR-5.

In a specific embodiment, an antibody to CC-CKR-5 inhibits HIV binding. Such an antibody may be used for passive immunotherapy and protection against host cell invasion by a number of viral isolates. Such an antibody has been shown inhibition of HIV-1 infection with a similar antibody raised against fusin. [see Dimitrov, D. S. Nature Medicine 2: 640–641 (1996)].

In another embodiment, the antibody is specific for a conformational isotope on the translocating promoter agent that becomes accessible upon binding CD4 and/or an envelope protein of HIV-1. In still another embodiment, the antibody reacts with a shared epitope of the translocation promoting agent and HIV or CD4 or both. In preferred embodiments of this aspect of the invention the translocating promoter agent is CC-CKR-5. In yet another embodiment, a chimeric antibody is prepared that specifically binds to the gp120-gp41 molecules of HIV-1 and CC-CKR-5.

In a further embodiment, the present invention relates to therapeutic methods which would be based upon modulating, and preferably inhibiting, the activity of the coreceptor (translocation promoting agent(s)) For example, drugs or other binding partners to the translocation promoting agent or proteins may be administered to inhibit HIV translocation promoting agent activity.

In a specific embodiment, infra, individuals who do not express a functional CRK-5 coreceptor are resistant to HIV infection despite exposure to the virus. Cells that do not express a functional CKR-5 coreceptor are highly resistant to HIV.

Thus, more specifically, the therapeutic method generally referred to herein could include the method to inhibit HIV infectivity, particularly from transmission by sexual contact by the administration of pharmaceutical compositions that may comprise effective inhibitors of activation of the translocation promoting agent, such as antibodies, or other drugs developed for instance by a drug screening assay prepared and used in accordance with a further aspect of the present invention. For example, drugs, antibodies or other binding partners to proteins such as CC-CKR5, may be administered to inhibit translocation promoting agent activity. Particular agents contemplated herein include proteins such as CC-CKR5 modified by the binding of the extracytoplasmic domain to a nonfunctional transmembrane domain, or to a lipid, to serve as a competitive inhibitor.

Further, the invention extends to the soluble form(s) of the coreceptor translocation promoting agent, that may function in similar fashion to antagonists to the agent, to inhibit HIV ingress to the target cell. In a specific embodiment, free soluble CC-CKR-5 cytoplasmic domain can be used to competitively inhibit HIV translocation mediated by CKR-5 coreceptor. All of the aforementioned agents, including small molecules and other cognates, may be formulated for use in the treatment of fluids such as the blood, and in the preparation, for example, of a spermicidal composition or like formulation, to treat the development of macrophage-trophic HIV that is known to be present in infected blood samples, and that is particularly known to be sexually transmitted.

In particular, proteins corresponding to soluble chemokine receptors set forth herein, their antibodies, or antagonists, could be prepared in pharmaceutical formulations for administration in instances wherein inhibitory therapy is appropriate. The application of the therapeutic compositions and methods of the invention will, it is believed, dramatically reduce the incidence of primary HIV infection.

Alternatively, the present invention provides for the suppression of coreceptor, e.g., CKR-5, expression, using antisense or ribozyme technology. Thus, in one aspect the invention provides for gene therapy using a construct than encodes as coreceptor, e.g., CKR-5, antisense or ribozyme in RNA. In another embodiment, synthetic antisense, or ribozyme nucleic acids, preferably modified to facilitate intracellular translocation, and to incorporate nuclease-resistant bonds, can be used. As shown in a specific example, infra, suppression of CKR-5 expression confers greatly increased resistance to macrophage-tropic HIV infection.

Yet another aspect of the invention includes the identification of a ligand for fusin. Supernatents and extracts of various cell lines and populations (e.g. CD8-lineage cells) are used to assay for the inhibition of infection by a fusin-tropic virus.

In a related aspect the identified ligand for fusin is isolated by standard column chromatography and gel electrophoresis, with the use of the assay described above. In one embodiment of this aspect of the invention, a fusin affinity column is used.

Accordingly, it is a principal object of the present invention to provide antagonists including antibodies, to the coreceptor (translocation promoter agent), methods for their preparation, including recombinant means.

It is a further object of the present invention to provide a method for detecting the presence and quantity of the coreceptor (translocation promoter agent), to thereby evaluate susceptibility to macrophage-tropic HIV infection.

It is a further object of the present invention to provide a method and associated assay system for screening substances such as drugs, agents and the like, potentially effective in inhibiting coreceptor-mediated HIV translocation.

It is a still further object of the present invention to provide a method for the treatment to control the amount or activity of the coreceptor (translocation promoter agent) so as to alter the adverse consequences of such presence or activity, e.g., to block HIV translocation.

It is a still further object of the present invention to provide a method for the treatment of mammals to control the amount or activity of the translocation promoter agent or its subunits, so as to treat or avert the adverse consequences of invasive, spontaneous or idiopathic pathological states.

It is a still further object of the present invention to provide pharmaceutical compositions for use in therapeutic methods which comprise or are based upon the coreceptor (translocation promoter agent).

These and other objects and advantages will become apparent to those skilled in the art from a review of the ensuing description which proceeds with reference to the following illustrative drawings.

BRIEF DESCRIPTION OF THE DRAWING FIGURES

FIG. 1 shows that chemokines block infection at the level of viral entry. PM1 cells were infected with luciferase reporter viruses pseudotyped with HIV-1 macrophage-tropic (ADA, JRFL) or T-cell line adapted virus (HXB2) Envs or A-MLV Env in the presence or absence of a mixture of individual β-chemokines or a mixture of chemokines. Luciferase activity was measured four days later as described below. This experiment was repeated four times with similar results.

FIGS. 2A–2C shows that CC-CKR5 mediates entry of macrophage-tropic HIV-1. cDNAs encoding chemokine receptors 1, 2A, 2B, 3, 4 and 5 were amplified from activated PBMC RNA using primers hybridizing to the respective 5' and 3' untranslated regions. Amplified products were cloned into pcDNA-I (InVitrogen) and pBABE-puro expression vectors. Each of the cDNAs was sequenced and determined to correspond to that previously reported. FIG. 2A depicts the results of 293 cells that were transfected with 5 $\mu$g CD4 expression vector pcCD4 and 15 $\mu$g pcDNA-I expression vectors for each of the CC-CKR genes. The next day the cells were plated in 24 well dishes ($2 \times 10^4$ per well) and one day later were infected with 20 ng p24 luciferase reporter viruses in a volume of 300 $\mu$l. Four days later, luciferase activity was measured as described above. FIG. 2B was performed under the same conditions as in FIG. 2A with addition of 20 $\mu$g ml$^{-1}$ Leu3A 30 min before adding virus. FIG. 2C was performed under the same conditions as FIG. 2A, except that pcCD4 was omitted from the transfection and replaced by pcDNA-1 control vector DNA.

FIGS. 3A–3D shows that the stable expression of CKR5 confers susceptibility to HIV entry that can be inhibited by anti-CD4 mAb or chemokines. Candidate receptors were introduced into CD4-positive and CD4-negative cell lines. FIG. 3A depicts the results of the infection of NIH3T3.CD4 cells (murine fibroblast) expressing different chemokine receptors or fusin-GFP. Fusin-GFP is a fusin protein in which Green Fluorescent Protein (GFP) has been attached to the C-terminus of fusin. FIG. 3B depicts the results of the chemokine induction of $Ca^{2+}$ signalling in 3T3.CD4-CKR stable transfectants. Comparison of cytoplasmic $Ca^{2+}$ levels in 3T3 cells expressing recombinant C—C chemokine receptors-1, –3, –5 (CKR-1, CKR-3, CKR-5), and the orphan receptor fusin after challenge with various chemokines as listed. Chemokines were added through an injection port at approximately 20 seconds (the sharp spike in each record) to a final concentration of 100 nM. The rise in intracellular calcium is represented by the rapid increase in relative fluorescence intensity. FIG. 3C depicts the results of the infection of HOS.CD4 cells (human osteosarcoma). FIG. 3D depicts the results of the infection of Hela.CD4 (human carcinoma); US28 is a β-chemokine receptor encoded by human cytomegalovirus.

FIGS. 4A–4D shows that CC-CKR-5 mediates of macrophage-tropic, but not T cell tropic, Env-dependent fusion. 293T cells were transfected with equal amounts of pcDNA1-based Env and pcRev expression vectors, cultured two days, seeded with CKR-5 of fusin cells, and Giemsa stained. FIG. 4A shows the results of cells transfected with CKR-5 and HXB2 ENV; FIG. 4B shows the results of cells transfected with CKR-5 and JRFL Env; FIG. 4C shows the results of cells tranfected with fusin and HXB2 Env; FIG. 4D shows the results of cells transfected with fusin and JRFL-Env.

FIGS. 5A–5D shows that CKR5 supports macrophage-tropic, but not T-cell line adapted virus replication in human and murine cells. FIG. 5A, PM1, FIG. 5B HOS-T4-BABE, and FIG. 5C HOS-T4-CKR5 cells ($5 \times 10^5$) were plated in 6-well dishes and the next day infected with replication competent T-cell line adapted HIV-HSA (dotted line) or macrophage-tropic HIV(BAL)-HSA reporter viruses (50 ng p24) (dashed line) or uninfected control cells (solid line). After five days the cells were stained with FITC-conjugated anti-HSA monoclonal antibody (Pharmingen) and analyzed in a Becton-Dickenson FACScaliber. FIG. 5B shows the results of time course of HIV(BaL)HSA virus replicating on HOS-T4-CKR5 cells. Cells were infected with HIV(BaL) HSA (-"B"-) and analyzed by FACS on indicated days. Control cells were infected with pBABE (-"J"-).

FIG. 6 depicts a gel showing that CC-CKR-5 is expressed in T cells and monocyte/macrophages. A ten-fold dilution series (lanes 1–5) starting at 1 pg of pcCKR5 plasmid DNA was amplified to test linearity of amplification. In lanes 6, no DNA was added. Monocytes were prepared by overnight adherence to plastic. T cells were prepared from the monocyte-depleted preparation by adherence to anti-CD2-coated beads (Dynal).

FIG. 7 shows the expression of CKR-1, CKR-5 and Fusin mRNA in EU Cells. RT-PCR amplification of CKR-5, fusin, CKR-1, glyceraldehyde phosphate dehydrogenase (GAPDH) transcripts from the indicated EU or normal donor T-cell clones. All RNAs were treated with RNAase-free DNase before cDNA synthesis. To confirm the absence of contaminating DNA, control cDNA reactions were prepared in which reverse transcriptase was omitted from each reaction. Amplified products were not observed in these controls (not shown). GAPDH served as control to confirm equal efficiency of amplification of each of the RNAs. Bottom panel shows PCR amplification of serial 10-fold dilutions of pcCKR5 plasmid DNA beginning with 1 ng. $10^0$, (lane 1); $10^{-1}$ (lane 2); $10^{-2}$ (lane 3); $10^{-3}$ (lane 4); $10^{-4}$ (lane 5); $10^{-5}$ (lane 6); $10^{-6}$ (lane 7); $10^{-7}$ (lane 8).

FIGS. 8A–8B shows that EU CKR-5 Does Not Function as an HIV-1 Coreceptor. FIG. 8A shows the results of CKR-5 expression vectors that were tested in a transient assay for the ability to mediate entry of macrophage-tropic virus. 293T cells were cotransfected with pcDNAI/amp expression vectors for CKR-5 cDNAs derived from indicated EU2, EU3, or normal donor cell lines and with CD4 expression vector pcCD4. To test for possible dominant negative activity, wild-type and EU-derived CKR-5 expression vectors were mixed in a 1:1 ratio and used to transfect 293T cells. The cells were infected with the indicated luciferase reporter viruses (10 ng $p24^{gag}$) pseudotyped by macrophage-tropic (JRFL, solid bars; ADA, left slant; BaL, right stipple), T-tropic (HXB2, heavy stiple) or A-MLV Env (right slant). Luciferase activity was measured three days later as described in Experimental Procedures. This experiment has been repeated three times with similar results. Wild-type CKR-5 has been amplified from three different cell lines and showed similar activity to that shown here. BaL Env typically results in significantly lower infectivity than the other two macrophage-tropic Envs. Error bars indicate standard deviation of duplicate independent measurements. FIG. 8B shows the results of HOS.CD4 cells stably expressing fusin cDNAs or containing control pBABE-puro vector alone were infected with luciferase reporter viruses as in FIG. 8A These cells have very low levels of endogenous fusin expression and become very susceptible following transfection (data not shown).

FIGS. 9A–9B shows that EU CKR-5 Contains a 32 bp Internal Deletion. FIG. 9A shows the nucleotide sequences of wild-type CKR-5 derived from normal donor (above) and EU cDNAs below) are shown. The nucleotide sequence from normal donor CKR-5 cDNA was determined for the complete 1,055 bp coding sequence and found to be identical to that reported by Samson et al. [Samson et al., 1996, Biochemistry 35: 3362–3367 (1996)]. The nucleotide sequence of 2 EU CKR-5 cDNAs were identical to wild-type over the complete coding region with the exception of a 32 bp deletion. Nucleotide sequence of the 200 bp region of CKR-5 encompassing the deletion was also determined for cDNAs derived from clones EU2.11, EU2.15, EU2.16, EU2.17 and EU3.1. Each contained the identical deletion with no additional nucleotide changes. Only the region flanking the deletion is shown. The deleted region (nt 794 to 825) is shaded. Amino acids encoded out of frame as a result of the deletion beginning at codon 185 are shown in italics. Nucleotide numbering (above) is from the first nucleotide of the reported CKR-5 sequence [Samson et al., 1996, supra]. Amino acid residue numbers are shown below. FIG. 9B shows the oligonucleotide primers used for nucleotide sequencing of CKR-5 cDNA and detecting the deleted allele by PCR. The coding region is indicated by dark shading. Primers have been designated by the nucleotide position at which they hybridize. Oligonucleotides used in PCR for detecting the deletion are shown as lightly shaded arrows. Oligonucleotides for cloning the full-length cDNA are shown at either end.

FIGS. 10A–10B shows that the EU CKR-5 Deletion is Present in Genomic DNA. FIG. 10A shows the results of CKR-5 amplified by PCR from genomic DNA of indicated EU, EU parent, or normal control PBMC. Primers SP4.760 and PM6.942 (shown in FIG. 3B) that flank the deletion were used to generate wild-type and deleted fragments of 182 bp and 150 bp, respectively. DNA from the other parents was unavailable. Control reactions in which DNA was omitted from the PCR had no amplified product (not shown). Sizes of marker fragments are indicated at left in base pairs. FIG. 10B depicts the results when genomic DNA (10 µg) isolated from PBMC of the indicated donors was digested with EcoRI and BglII and hybridized to a [$^{32}$P]-labeled CKR-5 probe. The position of the wild-type and deleted fragments is indicated by arrows.

FIG. 11 shows that EU2 is Homozygous for Deleted CKR-5. Genomic DNA from normal donor PBMC, from normal donor T-cell clones LW4.39 and LW5.49, and from EU2-derived T-cell clone EU2.11 was cleaved with indicated restriction enzyme. The cleaved DNA was separated by agarose gel electrophoresis and hybridized to a [$^{32}$P]-labeled, CKR-5 cDNA probe. Arrows indicate CKR-5 fragments. The 22 kb band in the EcoRI digests is derived from a fragment containing the 3'-end of CKR-5. The other faint high molecular weight bands are likely to correspond to CKR-2 which is closely related in nucleotide sequence. High stringency washing of similar filters in pilot experiments removed these bands. CKR-5 bands from EU2 are equal in intensity to those of controls, suggesting diploid content. The intensity of a fragment with a haploid content is shown by PvuII digest of LW5.49 who is heterozygous for a PvuII RFLP. Molecular size markers are indicated at left in kb.

FIGS. 12A–12D shows that EU CKR-5 is Not Detectable at the Cell Surface or in the Cytoplasm and does not Transduce Intracellular Signals. FIG. 12A shows the results when 293T cells were cotransfected with equal amounts of CD4 expression vector pcCD4 and indicated wild-type CKR-5 (HA-CKR5), EU CKR-5 (HA-CKR5.EU2.16 and HA-CKR5.EU3.1), or control pcDNAI/amp vector. Two days later, the cells were stained with FITC-conjugated anti-CD4 MAb Leu3a, anti-HA MAb 12CA5 and phycoerythrin-conjugated second antibody. Expression vectors for EU HA-CKR-5 were derived from T-cell clones EU2.16 and EU3.1, as indicated. The number of cells staining positive for both the HA epitope and CD4 is indicated as the percentage of cells falling in the upper right quadrant. Untransfected cells did not stain significantly with either antibody (data not shown). FIG. 12B depicts the results when the transfected cells were lysed and cytoplasmic HA-tagged CKR-5 was detected on immunoblots probed with anti-HA MAb. CKR-5 appears as an extremely heterogeneous band extending from 40 k-Da to the origin. The heterogeneous mobility of CKR-5 on SDS-PAGE appears to be a property of this family of proteins since similar results were found on immunoblots probed for CKR-1 (data not shown). FIG. 12C–12D show the results when EU cells fail to increase intracellular [$Ca^{2+}$] in response to MIP-1β. PBMC from EU2 or normal control donor were loaded with the calcium probe Fura-2 and exposed to MIP-1β and then RANTES (100 nM each) at the times indicated by arrows. Intracellular [$Ca^{2+}$] was measured by spectrofluorimetry as described in the Experimental Procedures. The chemokine binding assay showed that cells from EU2 FIG. 12D bound two to three-fold less MIP-1β than the control FIG. 12C. Both bound similar amounts of RANTES (data not shown).

FIGS. 13A–13B shows that the Deleted CKR-5 Allele is Frequent in Some Populations. FIG. 13A shows the results of the CKR-5 alleles amplified from 42 genomic DNAs from individuals of Western European heritage in the CEPH reference mapping resource [MacDonald et al., Am. J. Hum. Genet. 49: 723–734 (1991)] (excluding codes 102 and 104). DNAs were isolated from donors of western European background. CKR-5 sequences were amplified using primers SP4.760 and PM6.942 (shown in FIG. 9) flanking the 32 bp deletion, generating wild-type and deleted fragments of 182 bp and 150 bp, respectively. Positions of markers are indicated at right in base pairs. PCR products were separated on 4% Metaphor agarose. Reactions containing no genomic DNA showed no amplified product (NEG). PCR amplification of pcCKR5 plasmid DNA showed only the 182 bp band (POS). Weak amplification of sample 29 may have been due to low genomic DNA concentration. In heterozygous samples (6, 16, 17, 18, 20, 30, 34, 35, 37) the bands have decreased intensity as compared to homozygotes, as expected. The deleted allele is always less intense than the wild-type band, possibly as a result of its smaller size. Two samples that amplified weakly but were wild-type are not shown. Thus, the frequency of heterozygous individuals in this population is 20.4%. FIG. 13B depicts the Southern analysis of selected heterozygous samples. Genomic DNA from T-cell clone EU2.15 (lane 1), selected heterozygous samples 30 (lane 2), 34 (lane 3), 35 (lane 4) and 37 (lane 5) and a control donor were cleaved with BglII and EcoRI and hybridized to a full-length [$^{32}$P-α]dCTP-labeled CKR-5 probe. Wild-type and deleted CKR-5 fragments are indicated.

DETAILED DESCRIPTION OF THE INVENTION

Figure 1B:
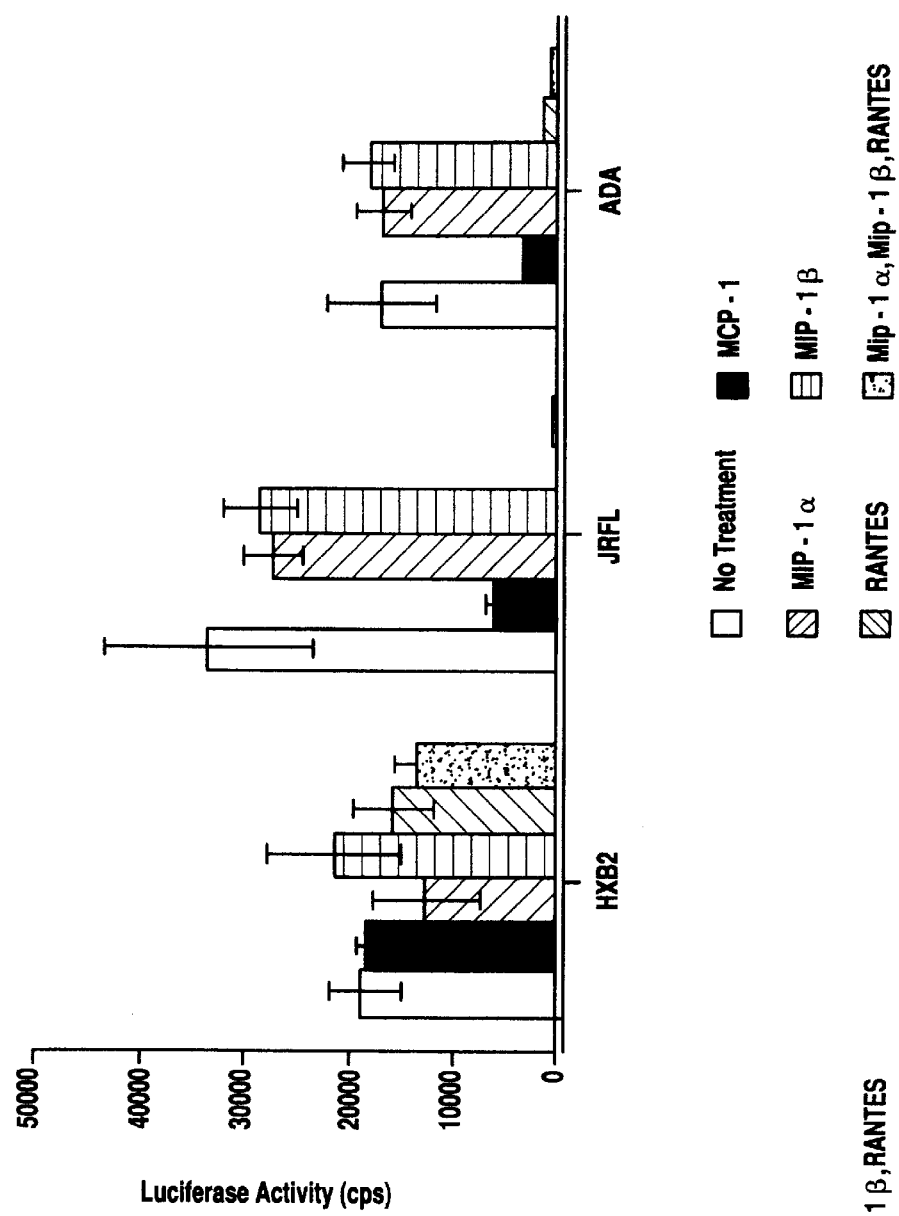

In its broadest aspect, the present invention relates to the identification and application of an agent capable of promoting the translocation of macrophage-tropic HIV through the membrane of a target CD4$^+$ cell, termed herein a coreceptor. A coreceptor of the invention is a chemokine receptor, which is present in, on, or proximal to the cell membrane of the target CD4$^+$ cell; acts in tandem with CD4, in connection with the translocation; and is capable of interacting with associated G-proteins to thereby transduce an intracellular signal. A further characteristic attendant to the activity of the translocation promoting agent of the present invention is an observed increase in the concentration of intracellular calcium. The present agent may also be described as a mediator of the entry of envelope glycoproteins of macrophage-tropic strains of HIV-1 into target cells. The present coreceptor (translocation promoting agent) appears to act as a co-factor that collaborates with CD4 in facilitating the penetration of the macrophage-tropic virus into the target cell to establish HW infection. A particular family of receptors known as C—C (or β) chemokine receptors (CKRs) has been identified as defining certain of the activities and characteristics set forth above, and a specific such receptor, CC-CKR5, is exemplified herein.

In a preferred aspect, the present invention is particularly directed to a method for identifying an individual who may be resistant to human immunodeficiency virus-1 (HIV-1) infection. The invention is based, in part, on identification of exposed but uninfected individuals who are homozygous for a mutation in the CKR-5 gene. Accordingly, the method comprises identifying whether an individual is homozygous, heterozygous, or normal for a mutation of a CKR-5 gene resulting in lack of expression of a functional CKR-5 chemokine receptor protein. Heterozygosity for a CKR-5 ± mutation indicates that the individual may be more resistant to HIV infection than normals, and homozygosity for a CKR-5 −/− mutation indicates that the individual may be more resistant than normals or than heterozygous individuals. In a specific embodiment, the individual is identified as heterozygous CKR-5 ±, and the resistance to HIV infection manifests as a reduced decline slope of CD4+ cells. In another specific embodiment, the individual is identified as homozygous CKR-5 −/−, and the resistance to HW infection manifests as remaining uninfected despite multiple high exposure to HIV.

The term "coreceptor" or "agent capable of promoting the translocation of macrophage-tropic virus" is used herein interchangeably with the terms "mediator of the entry of envelope glycoproteins of macrophage-trophic strains", "translocating promoter", "translocation promoting agent", "translocating promoting agent", and "translocating promoting protein" refer to a chemokine receptor found on membranes of CD4$^+$ cells that interact with CD4, transduce a signal via a G-protein and is involved in HIV translocation. Specific agents include members of the β-chemokine receptor family. One specific member of the β-chemokine receptor family capable of promoting the translocation of macrophage-tropic virus is CC-CKR-5 (also termed "CKR-5").

In one aspect, the present invention relates to the finding that β-chemokines inhibit HIV-1 replication by blocking entry of the virus into CD4$^+$ cells. In light of this finding, it was surmised that one or more of the β-chemokine receptors serve as a required accessory factor for entry by macrophage-tropic HIV-1. The major members of the CC-CKR family were tested for their ability to facilitate infection with macrophage-tropic HIV-1 strains and fusion with cells expressing envelope glycoproteins from these strains. The results indicate that the product of the recently identified gene encoding CC-CKR5 acts in concert with CD4 to allow entry of primary macrophage-tropic strains of HIV-1. Thus, C—C Chemokine Receptor 5 can be a necessary cofactor for entry of the HIV-1 virus into CD4$^+$ cells.

The invention further relates to the discovery that individuals who are homozygous for mutation in the CKR-5 are highly resistant to HIV infection despite significant exposure via sexual contact. Cells from these individuals require exposure to a 1000-fold greater level of HIV for infection in vitro. Furthermore, there is a significant reduction in the slope of CD4-cell decline in heterozygous CKR-5 ± individuals. These results clearly indicate that partial or complete suppression of CKR-5 protects against HIV. They also provide a useful prognostic indicator for susceptibility to HIV infection, particularly via sexual contact. An added benefit that CKR-5 −/− subjects do not appear to have any immunomodulatory deficit as a result of this mutation. Thus, therapeutic suppression of CKR-5 expression is expected to have few or no adverse effects, while providing protection from macrophage-tropic HIV.

An initial objective out of which the present invention grew is to understand the mechanism through which HIV gains entrance into target cells. It has been known that the virus binds to CD4, but that CD4 is not sufficient for infection. Identification of CKR-5 as an HIV coreceptor provides a target for blocking macrophage-tropic HIV infection, either with an antibody or small molecule that competitively inhibits HIV binding to the receptor, or by suppressing coreceptor, e.g., CKR-5, expression. With the new molecules available, it will be possible to study the biochemical events involved in initiation of fusion between the viral envelope and the cellular plasma membrane. The other, and, potentially, more important purpose is to develop a small animal model for HIV, which will allow a better understanding of the pathogenesis of AIDS and provide a system for testing potential therapies.

By means of the teachings of the present invention, it will be possible to screen for inhibitors of envelope-chemokine receptor interactions, possibly using analogs of known CC chemokines. In conjunction with soluble CD4, this should provide a powerful approach for blocking HIV infectious life cycle prior to viral entry.

It will be possible to develop animal model systems for studying HIV infection and pathogenesis. This will allow testing of drugs in an animal system prior to human trials. This discovery will potentially allow identification of additional related G-protein coupled receptors that have a role in broadening of the viral host range in vivo and in pathogenesis in organ systems such as the brain.

This discovery raises the possibility that chemokine receptors encoded by other viruses, particularly members of the Herpes virus family (CMV, HHV-6, HHV-8), serve to broaden the host range of HIV in individuals infected with both HIV and such viruses. This may therefore increase the range of tissues infected or provide a ligand for HIV envelope that may result in deleterious signal transduction in various tissues. This information would lead to novel approaches to block the synergy between HIV and viral cofactors.

Investigation of the genetic basis of resistance of the cells from exposed-uninfected individuals EU2 and EU3 to HIV-1 infection has led to the discovery that both individuals have an identical homozygous defect in the gene encoding CKR-5. This defect, a 32 bp deletion in the region corresponding to the second extracellular loop of CKR-5, encodes a severely truncated molecule that fails to reach the cell surface. As a result, the cells are resistant to infection by macrophage-tropic virus. It is likely that the defect in CKR-5 is primarily responsible for the ability of these individuals to remain uninfected following repeated exposure to HIV-1. Furthermore these findings suggest an essential role for CKR-5 in the sexual transmission of HIV-1.

Various additional terms are used in the specification, which are defined as follows:

A molecule is "antigenic" when it is capable of specifically interacting with an antigen recognition molecule of the immune system, such as an immunoglobulin (antibody) or T cell antigen receptor. An antigenic polypeptide contains at least about 5, and preferably at least about 10, amino acids. An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

A composition comprising "A" (where "A" is a single protein, DNA molecule, vector, recombinant host cell, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically" acceptable means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host.

In a specific embodiment, the term about means within about 20%, preferably within about 10%, and more preferably within about 5%.

Genes Encoding Coreceptor (Translocation Promoting Proteins)

The present invention contemplates isolation of a gene encoding a coreceptor (translocation promoting agent) of the invention, including a full length, or naturally occurring form of coreceptor and any antigenic fragments thereof from any animal, particularly mammalian or avian, and more particularly human, source. As used herein, the term "gene" refers to an assembly of nucleotides that encode a polypeptide, and includes cDNA and genomic DNA nucleic acids. Naturally, the present invention includes a gene encoding the mutated CKR-5 receptor having a 32 base pair deletion from nucleotides 794 to 825 in a region of the CKR-5 gene corresponding to the second extracellular loop. Such a gene is useful as a labeled probe, for preparing transfected cells to evaluate permissiveness of cells to HIV infection using different HIV isolates, and in preparing transgenic animals for the same purpose.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning*: A Practical Approach, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Therefore, if appearing herein, the following terms shall have the definitions set out below.

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell.

"Heterologous" DNA refers to DNA not naturally located in the cell, or in a chromosomal site of the cell. Preferably, the heterologous DNA includes a gene foreign to the cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–0.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

A "signal sequence" is included at the beginning of the coding sequence of a protein to be secreted or expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

As used herein, the term "sequence homology" in all its grammatical forms refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50: 667).

Accordingly, the term "sequence similarity" in all its grammatical forms refers to the degree of identity or correspondence between nucleic acid or amino acid sequences of proteins that do not share a common evolutionary origin (see Reeck et al., supra). However, in common usage and in the instant application, the term "homologous," when modified with an adverb such as "highly," may refer to sequence similarity and not a common evolutionary origin.

The term "corresponding to" is used herein to refer similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

A gene encoding translocation promoting, whether genomic DNA or cDNA, can be isolated from any source, particularly from a human cDNA or genomic library. Methods for obtaining translocation promoting gene are well known in the art, as described above (see, e.g., Sambrook et al., 1989, supra). The DNA may be obtained by standard procedures known in the art from cloned DNA (e.g., a DNA "library"), and preferably is obtained from a cDNA library prepared from tissues with high level expression of the protein (e.g., a macrophage/monocyte or T lymphocyte cDNA library, since these are the cells that evidence highest levels of expression of translocation promoting protein), by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will not contain intron sequences. Whatever the source, the gene should be molecularly cloned into a suitable vector for propagation of the gene.

Once the DNA fragments are generated, identification of the specific DNA fragment containing the desired coreceptor gene may be accomplished in a number of ways. For example, if an amount of a portion of a coreceptor gene or its specific RNA, or a fragment thereof, is available and can be purified and labeled, the generated DNA fragments may be screened by nucleic acid hybridization to the labeled probe (Benton and Davis, 1977, Science 196: 180; Grunstein and Hogness, 1975, Proc. Natl. Acad. Sci. U.S.A. 72: 3961). For example, a set of oligonucleotides corresponding to the partial amino acid sequence information obtained for the translocation promoting protein can be prepared and used as probes for DNA encoding translocation promoting, as was done in a specific example, infra, or as primers for cDNA or mRNA (e.g., in combination with a poly-T primer for RT-PCR). Preferably, a fragment is selected that is highly unique to translocation promoting of the invention. Those DNA fragments with substantial homology to the probe will hybridize. As noted above, the greater the degree of homology, the more stringent hybridization conditions can be used. In a specific embodiment, stringency hybridization conditions are used to identify a homologous coreceptor gene.

Further selection can be carried out on the basis of the properties of the gene, e.g., if the gene encodes a protein product having the isoelectric, electrophoretic, amino acid composition, or partial amino acid sequence of translocation promoting protein as disclosed herein. Thus, the presence of the gene may be detected by assays based on the physical, chemical, immunological, or functional properties of its expressed product. For example, cDNA clones, or DNA clones which hybrid-select the proper mRNAs, can be selected which produce a protein that, e.g., has similar or identical electrophoretic migration, isoelectric focusing or non-equilibrium pH gel electrophoresis is behavior, proteolytic digestion maps, or antigenic properties as known for β-chemokine receptors.

The present invention also relates to genes encoding analogs and derivatives of the coreceptor of the invention, that have the same or homologous functional activity as translocation promoting, and homologs thereof from other species. The production and use of derivatives and analogs related to translocation promoting are within the scope of the present invention. In a specific embodiment, the derivative or analog is functionally active, i.e., capable of exhibiting one or more functional activities associated with a full-length, wild-type translocation promoting of the invention. In another embodiment, translocation promoting containing a different cytoplasmic domain, e.g., which associates the protein with the cell membrane but does not mediate G protein activation, translocation, or both.

Coreceptor analogues can be made by altering encoding nucleic acid sequences by substitutions, additions or deletions that provide for functionally equivalent molecules. Preferably, derivatives are made that have decreased functional activity relative to native translocation promoting activity of the coreceptor. More preferably, the coreceptor analogue of the invention functions about as well as the native chemokine receptor for binding chemokines and inducing intracellular signalling, while functioning poorly or not at all in translocating HIV. Alternatively, coreceptor derivatives may encode soluble fragments of coreceptor extracellular domain that have the same or greater affinity for the natural ligand of translocation promoting of the invention. Such soluble derivatives may be potent inhibitors of HIV binding to the translocation promoting protein on cells, e.g., to CC-CKR5 on macrophages and T cells.

Due to the degeneracy of nucleotide coding sequences, other DNA sequences which encode substantially the same amino acid sequence as a coreceptor gene may be used in the practice of the present invention. These include but are not limited to allelic genes, homologous genes from other species, and nucleotide sequences comprising all or portions of coreceptor genes that are altered by the substitution of different codons that encode the same amino acid residue within the sequence, thus producing a silent change. Likewise, the coreceptor derivatives of the invention include, but are not limited to, those containing, as a primary amino acid sequence, all or part of the amino acid sequence of a coreceptor protein including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

The genes encoding coreceptor derivatives and analogs of the invention can be produced by various methods known in the art. The manipulations which result in their production can occur at the gene or protein level. For example, the cloned coreceptor gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of translocation promoting, care should be taken to ensure that the modified gene remains within the same translational reading frame as the translocation promoting gene, uninterrupted by translational stop signals, in the gene region where the desired activity is encoded.

Additionally, the coreceptor-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Preferably, such mutations inhibit the HIV translocating functional activity of the mutated coreceptor gene product. Such genes may be useful in gene therapy to express a chemokine receptor, CRK-5 that any technique for mutagenesis known in the art can be used, including but not limited to, in vitro site-directed mutagenesis (Hutchinson, C., et al., 1978, J. Biol. Chem. 253: 6551; Zoller and Smith, 1984, DNA 3: 479–488; Oliphant et al., 1986, Gene 44: 177; Hutchinson et al., 1986, Proc. Natl. Acad. Sci. U.S.A. 83: 710), use of TAB® linkers (Pharmacia), etc. PCR techniques are preferred for site directed mutagenesis (see Higuchi, 1989, "Using PCR to Engineer DNA", in PCR *Technology: Principles and Applications for DNA Amplification,* H. Erlich, ed., Stockton Press, Chapter 6, pp. 61–70).

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *E. coli,* bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., *E. coli,* and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences form the yeast 2, plasmid.

Expression of Coreceptor Polypeptides

The nucleotide sequence coding for coreceptor protein, or antigenic fragment, derivative or analog thereof, or a functionally active derivative, including a chimeric protein, thereof, can be inserted into an appropriate expression vector, i.e., a vector which contains the necessary elements for the transcription and translation of the inserted protein-coding sequence. Such elements are termed herein a "promoter." Thus, the nucleic acid encoding a coreceptor of the invention is operationally associated with a promoter in an expression vector of the invention. Both cDNA and genomic sequences can be cloned and expressed under control of such regulatory sequences. An expression vector also preferably includes a replication origin. Naturally, the invention contemplates expression of the mutant gene as well.

The necessary transcriptional and translational signals can be provided on a recombinant expression vector, or they may be supplied by the native gene encoding the coreceptor and/or its flanking regions.

As pointed out above, potential chimeric partners for coreceptors include other transmembrane domains, a domain for modification with a phospholipid anchor, or, as demonstrated in an example, infra, a marker (label) polypeptide.

A recombinant translocation promoting protein of the invention, or functional fragment, derivative, chimeric construct, or analog thereof, may be expressed chromosomally, after integration of the coding sequence by recombination. In this regard, any of a number of amplification systems may be used to achieve high levels of stable gene expression (See Sambrook et al., 1989, supra).

The cell into which the recombinant vector comprising the nucleic acid encoding translocation promoting is cultured in an appropriate cell culture medium under conditions that provide for expression of coreceptor by the cell.

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of coreceptor protein may be controlled by any promoter/enhancer element known in the art, but these regulatory elements must be functional in the host selected for expression. Promoters which may be used to control translocation promoting gene expression include, but are not limited to, the SV40 early promoter region (Benoist and Chambon, 1981, Nature 290: 304–310), the promoter contained in the 3' long terminal repeat of Rous sarcoma virus (Yamamoto, et al., 1980, Cell 22: 787–797), the herpes thymidine kinase promoter (Wagner et al., 1981, Proc. Natl. Acad. Sci. U.S.A. 78: 1441–1445), the regulatory sequences of the metallothionein gene (Brinster et al., 1982, Nature 296: 39–42); prokaryotic expression vectors such as the β-lactamase promoter (Villa-Kamaroff, et al., 1978, Proc. Natl. Acad. Sci. U.S.A. 75: 3727–3731), or the tac promoter (DeBoer, et al., 1983, Proc. Natl. Acad. Sci. U.S.A. 80: 21–25); see also "Useful proteins from recombinant bacteria" in Scientific American, 1980, 242: 74–94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells [Swift et al., 1984, Cell 38: 639–646; Ornitz et al., 1986, Cold Spring Harbor Symp. Quant. Biol. 50: 399–409; MacDonald, 1987, Hepatology 7: 425–515]; insulin gene control region which is active in pancreatic beta cells (Hanahan, 1985, Nature 315: 115–122), immunoglobulin gene control region which is active in lymphoid cells (Grosschedl et al., 1984, Cell 38: 647–658; Adames et al., 1985, Nature 318: 533–538; Alexander et al., 1987, Mol. Cell. Biol. 7: 1436–1444), mouse mammary tumor virus control region which is active in testicular, breast, lymphoid and mast cells (Leder et al., 1986, Cell 45: 485–495), albumin gene control region which is active in liver (Pinkert et al., 1987, Genes and Devel. 1: 268–276), alpha-fetoprotein gene control region which is active in liver (Krumlauf et al., 1985, Mol. Cell. Biol. 5: 1639–1648; Hammer et al., 1987, Science 235: 53–58), alpha 1-antitrypsin gene control region which is active in the liver (Kelsey et al., 1987, Genes and Devel. 1: 161–171), beta-globin gene control region which is active in myeloid cells (Mogram et al., 1985, Nature 315: 338–340; Kollias et al., 1986, Cell 46: 89–94), myelin basic protein gene control region which is active in oligodendrocyte cells in the brain (Readhead et al., 1987, Cell 48: 703–712), myosin light chain-2 gene control region which is active in skeletal muscle (Sani, 1985, Nature 314: 283–286), and gonadotropic releasing hormone gene control region which is active in the hypothalamus (Mason et al., 1986, Science 234: 1372–1378).

A wide variety of host/expression vector combinations may be employed in expressing the DNA sequences of this invention. Useful expression vectors, for example, may consist of segments of chromosomal, non-chromosomal, and synthetic DNA sequences. Suitable vectors include derivatives of SV40 and known bacterial plasmids, e.g., E. coli plasmids col El, pCR1, pBR322, pMal-C2, pET, pGEX (Smith et al., 1988, Gene 67: 3140), pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

In addition, a host cell strain may be chosen which modulates the expression of the inserted sequences, or modifies and processes the gene product in the specific fashion desired. Different host cells have characteristic and specific mechanisms for the translational and post-translational processing and modification (e.g., glycosylation, cleavage [e.g., of signal sequence]) of proteins. Appropriate cell lines or host systems can be chosen to ensure the desired modification and processing of the foreign protein expressed. For example, expression in a bacterial system can be used to produce an nonglycosylated core protein product. However, the transmembrane coreceptor protein expressed in bacteria may not be properly folded. Expression in yeast can produce a glycosylated product. Expression in eukaryotic cells can increase the likelihood of "native" glycosylation and folding of a heterologous protein. Moreover, expression in mammalian cells can provide a tool for reconstituting, or constituting, HIV translocation promoting activity, particularly in cells that express CD4. Furthermore, different vector/host expression systems may affect processing reactions, such as proteolytic cleavages, to a different extent.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267: 963–967; Wu and Wu, 1988, J. Biol. Chem. 263: 14621–14624; Hartmut et al., Canadian Patent Application No. 2,012,311, filed Mar. 15, 1990).

A recombinant coreceptor protein expressed as an integral membrane protein can be isolated and purified by standard methods. Generally, the integral membrane protein can be obtained by lysing the membrane with detergents, such as but not limited to, sodium dodecyl sulfate (SDS), Triton X-100, nonidet P-40 (NP-40), digoxin, sodium deoxycholate, and the like, including mixtures thereof. Solubilization can be enhanced by sonication of the suspension. Soluble forms of the protein can be obtained by collecting culture fluid, or solubilizing inclusion bodies, e.g., by treatment with detergent, and if desired sonication or other mechanical processes, as described above. The solubilized or soluble protein can be isolated using various techniques, such as polyacrylamide gel electrophoresis (PAGE), isoelectric focusing, 2-dimensional gel electrophoresis, chromatography (e.g., ion exchange, affinity, immunoaffinity, and sizing column chromatography), centrifugation, differential solubility, immunoprecipitation, or by any other standard technique for the purification of proteins.

For the assays of the invention that depend on evaluating the activity of the coreceptor protein, preferably the gene encoding the protein is transfected or used to transform host cells. More preferably, such host cells are transfected to co-express human CD4, and more preferably, such cells lack the ability to express an endogenous or native CD4. Co-expression of the translocation promoting protein and CD4 facilitates HIV translocation, which is the endpoint for an assay to identify antagonists of HIV translocation.

Antibodies to Translocation Promoting Protein

According to the invention, coreceptor protein produced recombinantly or by chemical synthesis, and fragments or other derivatives or analogs thereof, including fusion proteins, may be used as an immunogen to generate antibodies that recognize the coreceptor protein. Such antibodies include but are not limited to polyclonal, monoclonal, chimeric, single chain, Fab fragments, and an Fab expression library. The anti-coreceptor protein antibodies of the invention may be cross reactive, e.g., they may recognize coreceptor protein from different species. Polyclonal antibodies have greater likelihood of cross reactivity. Alternatively, an antibody of the invention may be specific for a single form of coreceptor protein. Preferably, such an antibody is specific for human translocation promoting protein.

In a specific embodiment, an antibody of the invention is specific for a masked epitope on the coreceptor protein that is exposed on binding to HIV. In another embodiment, an antibody of the invention is specific for an epitope created by the binding of the translocation promoting protein with HIV or CD4, or both. Such antibodies can be selected on the basis of binding under conditions of HIV binding to the translocation promoting protein, e.g., at 4° C. to inhibit translocation, and screened for non-binding to free translocation promoting protein.

Various procedures known in the art may be used for the production of polyclonal antibodies to coreceptor protein or derivative or analog thereof. For the production of antibody, various host animals can be immunized by injection with the coreceptor protein, or a derivative (e.g., fragment or fusion protein) thereof, including but not limited to rabbits, mice, rats, sheep, goats, etc. In one embodiment, the coreceptor protein or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the coreceptor protein, or fragment, analog, or derivative thereof, any technique that provides for the production of antibody molecules by continuous cell lines in culture may be used. These include but are not limited to the hybridoma technique originally developed by Kohler and Milstein [Nature 256: 495–497 (1975)], as well as the trioma technique, the human B-cell hybridoma technique [Kozbor et al., Immunology Today 4: 72 1983); Cote et al., Proc. Natl. Acad. Sci. U.S.A. 80: 2026–2030 (1983)], and the EBV-hybridoma technique to produce human monoclonal antibodies [Cole et al., in Monoclonal Antibodies and Cancer Therapy, Alan R. Liss, Inc., pp. 77–96 (1985)]. In an additional embodiment of the invention, monoclonal antibodies can be produced in germ-free animals utilizing recent technology [PCT/US89/02545; International Patent Publication WO 89/12690]. In fact, according to the invention, techniques developed for the production of "chimeric antibodies" [Morrison et al., J. Bacteriol. 159: 870 (1984); Neuberger et al., Nature 312: 604–608 (1984); Takeda et al., Nature 314: 452–454 (1985)] by splicing the genes from a mouse antibody molecule specific for an translocation promoting protein together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies [U.S. Pat. Nos. 5,476, 786 and 5,132,405 to Huston; U.S. Pat. No. 4,946,778] can be adapted to produce coreceptor protein-specific single chain antibodies. An additional embodiment of the invention utilizes the techniques described for the construction of Fab expression libraries [Huse et al., Science 246: 1275–1281 (1989)] to allow rapid and easy identification of monoclonal Fab fragments with the desired specificity for a coreceptor protein, or its derivatives, or analogs.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of an translocation promoting protein, one may assay generated hybridomas for a product which binds to an translocation promoting protein fragment containing such epitope. For selection of an antibody specific to an translocation promoting protein from a particular species of animal, one can select on the basis of positive binding with translocation promoting protein expressed by or isolated from cells of that species of animal.

The foregoing antibodies can be used in methods known in the art relating to the localization and activity of the coreceptor protein, e.g., for FACS analysis, Western blotting, imaging coreceptor protein in situ, measuring levels thereof in appropriate physiological samples, etc. using any of the detection techniques mentioned above or known in the art. The antibodies can be used to quantitate the level of expression of coreceptor, which correlates with permissiveness for HIV infection.

Suitable labels for antibodies include enzymes, fluorophores (e.g., fluorescene isothiocyanate (FITC), phycoerythrin (PE), Texas red (TR), rhodamine, free or chelated lanthanide series salts, especially $Eu^{3+}$, to name a few fluorophores), chromophores, radioisotopes, chelating agents, dyes, colloidal gold, latex particles, ligands (e.g., biotin), and chemiluminescent agents. When a control marker is employed, the same or different labels may be used for the receptor and control marker. In the instance where a radioactive label, such as the isotopes $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used currently available counting procedures may be utilized. In the instance where the label is an enzyme, detection may be accomplished by any of the presently utilized colorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g., U.V. light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labelling devices, indirect labels comprising enzymes can also be used according to the present invention.

Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in Methods in Enzymology, 70: 419–439, 1980 and in U.S. Pat. No. 4,857,453. Suitable enzymes include, but are not limited to, alkaline phosphatase and horseradish peroxidase.

Other labels for use in the invention include magnetic beads or magnetic resonance imaging labels.

In another embodiment, a phosphorylation site can be created on an antibody of the invention for labeling with $^{32}P$, e.g., as described in European Patent No. 0372707 (application No. 89311108.8) by Sidney Pestka, or U.S. Pat. No. 5,459,240, issued Oct. 17, 1995 to Foxwell et al.

As exemplified herein, proteins, including antibodies, can be labeled by metabolic labeling. Metabolic labeling occurs during in vitro incubation of the cells that express the protein in the presence of culture medium supplemented with a metabolic label, such as $[^{35}S]$-methionine or $[^{32}P]$-orthophosphate. In addition to metabolic (or biosynthetic) labeling with $[^{35}S]$-methionine, the invention farther contemplates labeling with $[^{14}C]$-amino acids and $[^{3}H]$-amino acids (with the tritium substituted at non-labile positions).

In a specific embodiment, antibodies that agonize or antagonize the activity of translocation promoting protein can be generated. Such antibodies can be tested using the assays described infra for identifying ligands.

Such antibodies, when conjugated with a toxin or radioactive element, can be used to target HIV-permissive cells for destruction. Thus, cells harboring HIV, particularly in its dormant phase, can be destroyed with antibodies, e.g., conjugated to a toxin such as ricin or a radioisotope such as $^{32}P$ or $^{125}I$, when such antibodies are specific for the translocation promoting protein.

Identification of Antagonists of HIV Translocation

Identification and isolation of a gene encoding a coreceptor protein of the invention provides for expression of coreceptor protein in quantities greater than can be isolated from natural sources, or in indicator cells that are specially engineered to indicate the activity of coreceptor protein expressed after transfection or transformation of the cells. Accordingly, the present invention contemplates an alternative method for identifying agonists and antagonists of HIV translocation directed to modulating the activity of the translocation promoting protein using various screening assays known in the art. In one embodiment, such agonists or antagonists competitively inhibit HIV binding to the translocation protein; in another embodiment, the agonist or antagonist indirectly affects HIV translocation, whether by non-competitive binding to the translocation promoting protein, or by affecting the level of expression of the translocation promoting protein.

Cell lines expressing CD4 and one or more members of the chemokine receptor family preferably CKR-5, are infected with an HIV-reporter virus that is pseudotyped with one or more selected envelope glycoproteins. Such cell lines are useful for assaying compound libraries for their ability to inhibit infection of the cells by the pseudotyoed virus. Candidate compounds are selected and then counter-screened for non-specific effects on infection with virus pseudotyped with non-HIV envelope proteins such as MLV, amphotropic env, or with VSV-G env. Suitable cell lines include, but are not limited to murine 3T3 cells, human HeLa, U87MG, HOS, and 293 cells. Additional human cell lines that do not normally express either fusin or CKR-5 (such as SCL) can also be used. Suitable HIV vectors include, but are not limited to HIV-luciferase, HIV-alkaline phosphatase, and HIV-CD24. In these vectors, the env gene is inactivated by frame shifting, and the reporter gene is inserted to replace the Nef open reading frame. Additional vectors can be made for easier screening in murine cells, in which expression of HIL-LTR-driven reporters is only about 1% of the level in human cells. Such vectors are based on the HIV-gpt prototype [Page et al. J. Virol. 64: 5270–5276 (1990)], such that the reporter, e.g., luciferase, is placed under control of the SV40 promoter within the env gene, ensuring high level expression following integration.

Envelope glycoproteins that are appropriate for screening CKR-5-transfected cells include, but are not be limited to, envs of JR-FL, ADA, and BaL primary isolates. Envelope glycoproteins that are appropriate for screening cells expressing fusin include HXB2, 5F2, and NL4-3 as well as HIV-2ROD. Envelope glycoproteins of SIVmac can also be used to assay inhibition of CKR-5 co-receptor function.

Any screening technique known in the art can be used to screen for translocation promoting protein agonists or antagonists. The present invention contemplates screens for small molecule ligands or ligand analogs and mimics, as well as screens for natural ligands that bind to and agonize or antagonize activities of translocation promoting protein in vivo. For example, natural products libraries can be screened using assays of the invention for molecules that agonize or antagonize translocation promoting protein activity.

Knowledge of the primary sequence of the, and the similarity of that sequence with proteins of known function, can provide an initial clue as the inhibitors or antagonists of the protein. Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" [Scott and Smith, 1990, Science 249: 386–390 (1990); Cwirla, et al., Proc. Natl. Acad. Sci., 87: 6378–6382 (1990); Devlin et al., Science, 249: 404–406 (1990)], very large libraries can be constructed ($10^6$–$10^8$ chemical entities). A second approach uses primarily chemical methods, of which the Geysen method [Geysen et al., Molecular Immunology 23: 709–715 (1986); Geysen et al. J. Immunologic Method 102: 259–274 (1987)] and the method of Fodor et al. [Science 251: 767–773 (1991)] are examples. Furka et al. [14th International Congress of Biochemistry, Volume 5, Abstract FR: 013 (1988); Furka, Int. J. Peptide Protein Res. 37: 487–493 (1991)], Houghton [U.S. Pat. No. 4,631,211, issued Dec. 1986] and Rutter et al. [U.S. Pat. No. 5,010,175, issued Apr. 23, 1991] describe methods to produce a mixture of peptides that can be tested as agonists or antagonists.

In another aspect, synthetic libraries [Needels et al., Proc. Natl. Acad. Sci. USA 90: 10700–4 (1993); Ohlmeyer et al., Proc. Natl. Acad. Sci. USA 90: 10922–10926 (1993); Lam et al., International Patent Publication No. WO 92/00252; Kocis et al., International Patent Publication No. WO 9428028, each of which is incorporated herein by reference in its entirety], and the like can be used to screen for translocation promoting protein ligands according to the present invention.

Alternatively, assays for binding of soluble ligand to cells that express recombinant forms of the translocation promoting protein ligand binding domain can be performed. The soluble ligands can be provided readily as recombinant or synthetic translocation promoting protein polypeptide.

The screening can be performed with recombinant cells that express the translocation promoting protein, or alternatively, using purified protein, e.g., produced recombinantly, as described above. For example, the ability of labeled, soluble or solubilized translocation promoting protein that includes the ligand-binding portion of the molecule, to bind ligand can be used to screen libraries, as described in the foregoing references.

*Administration of Antagonists of the CC-CKR-5 (CD4-gp120-gp41) complex* According to the invention, the component or components of a therapeutic composition of the invention may be introduced parenterally, transmucosally, e.g., orally, nasally, or rectally, or transdermally. Preferably, administration is parenteral, e.g., via intravenous injection, and also including, but is not limited to, intra-arteriole, intramuscular, intradermal, subcutaneous, intraperitoneal, intraventricular, and intracranial administration. More preferably, where administration of an antagonist to the CC-CKR-5 -(CD4-gp120-gp41) complex is administered to prevent or treat AIDs, it may be introduced by injection into the blood. The antagonist may be a specific antibody raised against the CC-CKR-5-(CD4-gp120-gp41)complex or a CC-CKR-5 mimic that competitively competes with CC-CKR-5 for the (CD4-gp120-gp41)complex.

In another embodiment, the therapeutic compound can be delivered in a vesicle, in particular a liposome [see Langer, Science 249: 1527–1533 (1990); Treat et al., in Liposomes in the Therapy of Infectious Disease and Cancer, Lopez-Berestein and Fidler (eds.), Liss: New York, pp. 353–365 (1989); Lopez-Berestein, ibid., pp. 317–327; see generally ibid.]. To reduce its systemic side effects, this may be a preferred method for introducing an antagonist to CC-CKR-5.

In yet another embodiment, the therapeutic compound can be delivered in a controlled release system. For example, an antibody may be administered using intravenous infusion, an implantable osmotic pump, a transdermal patch, liposomes, or other modes of administration. In one embodiment, a pump may be used [see Langer, supra; Sefton, CRC Crit. Ref. Biomed. Eng. 14: 201 (1987); Buchwald et al., Surgery 88: 507 (1980); Saudek et al., N. Engl. J. Med. 321: 574 (1989)]. In another embodiment, polymeric materials can be used [see Medical Applications of Controlled Release, Langer and Wise (eds.), CRC Press: Boca Raton, Fla. (1974); Controlled Drug Bioavailability, Drug Product Design and Performance, Smolen and Ball (eds.), Wiley: New York (1984); Ranger and Peppas, J. Macromol. Sci. Rev. Macromol. Chem. 23: 61 (1983); see also Levy et al., Science 228: 190 (1985); During et al., Ann. Neurol. 25: 351 (1989); Howard et al., J. Neurosurg. 71: 105 (1989)]. In yet another embodiment, a controlled release system can be placed in proximity of the therapeutic target, i.e., the brain, thus requiring only a fraction of the systemic dose [see, e.g., Goodson, in *Medical Applications of Controlled Release*, supra, vol. 2, pp. 115–138 (1984)].

Other controlled release systems are discussed in the review by Langer [Science 249: 1527–1533 (1990)].

Thus, the antagonist can be delivered by intravenous, intraarterial, intraperitoneal, intramuscular, or subcutaneous routes of administration. Alternatively, the antagonist, properly formulated, can be administered by nasal or oral administration. A constant supply of the antagonist can be ensured by providing a therapeutically effective dose (i.e., a dose effective to induce metabolic changes in a subject) at the necessary intervals, e.g., daily, every 12 hours, etc. These parameters will depend on the severity of the disease condition being treated, other actions, such as diet modification, that are implemented, the weight, age, and sex of the subject, and other criteria, which can be readily determined according to standard good medical practice by those of skill in the art.

A subject in whom administration of the antagonist is an effective therapeutic regiment for AIDS is preferably a human, but can be a primate with a related viral condition. Thus, as can be readily appreciated by one of ordinary skill in the art, the methods and pharmaceutical compositions of the present invention are particularly suited to administration to any primate.

Transgenic Vectors and Inhibition of Expression

In one embodiment, a gene encoding a translocation promoting protein, or antisense or ribozyme specific for translocation promoting protein mRNA (termed herein an "antigene") is introduced in vivo in a viral vector. Such vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, adipose tissue can be specifically targeted. Examples of particular vectors include, but are not limited to, a defective herpes virus 1 (HSV1) vector [Kaplitt et al., Molec. Cell. Neurosci. 2: 320–330 (1991)], an attenuated adenovirus vector, such as the vector described by Stratford-Perricaudet et al. [J. Clin. Invest. 90: 626–630 (1992)], and a defective adeno-associated virus vector [Samulski et al., J. Virol. 61: 3096–3101 (1987); Samulski et al., J. Virol. 63: 3822–3828 (1989)].

In another embodiment the gene or antigene can be introduced in a retroviral vector, e.g., as described in Anderson et al., U.S. Pat. No. 5,399,346; Mann et al., 1983, Cell 33: 153; Temin et al., U.S. Pat. No. 4,650,764; Temin et al., U.S. Pat. No. 4,980,289; Markowitz et al., 1988, J. Virol. 62: 1120; Temin et al., U.S. Pat. No. 5,124,263; International Patent Publication No. WO 95/07358, published Mar. 16, 1995, by Dougherty et al.; and Kuo et al., 1993, Blood 82: 845.

Targeted gene delivery is described in International Patent Publication WO 95/28494, published October 1995.

Alternatively, the vector can be introduced in vivo by lipofection [Felgner, et. al., Proc. Natl. Acad. Sci. U.S.A. 84: 7413–7417 (1987); see Mackey, et al., Proc. Natl. Acad. Sci. U.S.A. 85: 8027–8031 (1988); Felgner and Ringold, Science 337: 387–388 (1989)]. Lipids may be chemically coupled to other molecules for the purpose of targeting [see Mackey, et. al., supra]. Targeted peptides, e.g., hormones or neurotransmitters, and proteins such as antibodies, or non-peptide molecules could be coupled to liposomes chemically.

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter [see, e.g., Wu et al., J. Biol. Chem. 267: 963–967 (1992); Wu and Wu, J. Biol. Chem. 263: 14621–14624 (1988); Hartmut et al., Canadian Patent Application No. 2,012,311, filed Mar. 15, 1990].

As noted above, the present invention extends to the preparation of antisense nucleotides and ribozymes that may be used to interfere with the expression of translocation promoting protein at the translational level. This approach utilizes antisense nucleic acid and ribozymes to block translation of a specific mRNA, either by masking that mRNA with an antisense nucleic acid or cleaving it with a ribozyme. Such antisense or ribozyme nucleic acids may be produced chemically, or may be expressed from an "antigen."

Antisense nucleic acids are DNA or RNA molecules that are complementary to at least a portion of a specific mRNA molecule [see Marcus-Sekura, Anal. Biochem. 172: 298 (1988)]. In the cell, they hybridize to that mRNA, forming a double stranded molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into organ cells. Antisense methods have been used to inhibit the expression of many genes in vitro [Marcus-Sekura, 1988, supra; Hambor et al., J. Exp. Med. 168: 1237 (1988)]. Preferably synthetic antisense nucleotides contain phosphoester analogs, such as phosphorothiolates, or thioesters, rather than natural phosphoester bonds. Such phosphoester bond analogs are more resistant to degradation, increasing the stability, and therefore the efficacy, of the antisense nucleic acids.

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it [Cech, J. Am. Med. Assoc. 260: 3030 (1988)]. Because they are sequence-specific, only mRNAs with particular sequences are inactivated.

Investigators have identified two types of ribozymes, Tetrahymena-type and "hammerhead"-type. Tetrahymena-type ribozymes recognize four-base sequences, while "hammerhead"-type recognize eleven- to eighteen-base sequences. The longer the recognition sequence, the more likely it is to occur exclusively in the target MRNA species. Therefore, hammerhead-type ribozymes are preferable to Tetrahymena-type ribozymes for inactivating a specific mRNA species, and eighteen base recognition sequences are preferable to shorter recognition sequences.

The DNA sequences encoding translocation promoting protein described and enabled herein may thus be used to prepare antisense molecules against and ribozymes that cleave mRNAs for translocation promoting protein, thus inhibiting expression of the gene encoding translocation promoting protein, which may reduce the level of HIV translocation in macrophages and T cells.

Transgenic Mice

The transgenic mice of the present application are produced as detailed in Killeen et al. 1993, supra, which is hereby incorporated by reference. The construction of the human CD4$^+$ murine CD4$^-$ mice are described by Killeen et al. 1993, supra. A CC-CKR-5 transgene is constructed using a human CC-CKR-5 minigene that includes all of the coding region exons and ~3 kb of sequence (including the first intron) upstream of the coding sequence. B6/SIL F2 eggs or B6/SIL F1 x human CD4$^+$/murine CD4$^-$ eggs are microinjected with the human CC-CKR-5 transgene according to standard procedures described by Hogan et al. [Manipulating the Mouse Embryo. Cold Spring Harbor Laboratory Press, Cold Spring Harbor, N.Y. (1986)]. Founders are identified by Southern blotting using a human CC-CKR-5 cDNA probe.

Cells on solid support

Solid supports include glass beads, sugar beads (Sephadex, Sepharose, Agarose, Sephacel etc.) magnetic beads, and dowex-type materials. Biological materials may be passed through cells bound to solid supports by common methods know to any person skilled in the art including but not limited by batchwise, by centrifugation, pressure-membrane filtration (e.g. Amicon or Millipore filtration) and through various types of columns.

EXAMPLE 1

CC-CKR-5 AND CD4 Function Cooperatively to Mediate Entry of Macrophage-tropic Virus Materials and Methods NL4-3-Luc-R$^-$E$^-$ virus stocks pseudotyped by various Envs were generated by transfecting 293T cells with 10 μg each of pNL4-3-Luc-R$^-$E$^-$ and pcDNAI-based expression vectors (InVitrogen) encoding JRFL, ADA, BaL, HXB2 or amphotropic MLV Env. Virus-containing supernatants were harvested 48 hours post-transfection and frozen in aliquots at −80°. Viruses were quantitated by ELISA assay for p24. Cells (5×10$^4$) were seeded in 48-well dishes in DMEM containing 10% fetal bovine serum and infected with luciferase reporter virus (50 ng p24) in a total volume of 400 μl with or without 30 minutes pretreatment with each of the chemokines listed (500 ng/ml, Peprotech). After 16 hours, 0.5 ml medium was added to the wells. After 4 days of additional culture, 100 μl lysates were prepared and luciferase activity in 20 μl was assayed using commercially available reagents (Promega).

cDNAs encoding chemokine receptors 1, 2A, 2B, 3, 4 and 5 were amplified from activated PBMC RNA using primers hybridizing to the respective 5' and 3' untranslated regions. Amplified products were cloned into pcDNA-I (InVitrogen) and pBABE-puro expression vectors. Each of the cDNAs was sequenced and determined to correspond to that previously reported. (A), 293 cells were transfected with 5 μg CD4 expression vector pcCD4 and 15 μg pcDNA-I expression vectors for each of the CC-CKR genes. The next day the cells were plated in 24 well dishes ($2 \times 10^4$ per well) and one day later were infected with 20 ng p24 luciferase reporter viruses in a volume of 300 μl. Four days later, luciferase activity was measured as described above. (B), same conditions as in (A) with addition of 20 μg ml$^{-1}$ Leu3A 30 min before adding virus. (C), same conditions as (A), except that pcCD4 was omitted from the transfection and replaced by pcDNA-1 control vector DNA.

Cell lines stably expressing chemokine receptors or fusin-GFP were established as previously described. Briefly, cDNAs encoding the indicated receptors were subcloned into pBABE-puro and transfected into BING packaging cells. 48 hour later supernatants were collected and used to infect NIH3T3 (3T3), 3T3.CD4, HOS, HOS.CD4, Hela, and Hela.CD4. After 48 hours cells were selected for puromycin resistance. One week after start of selection, puro-resistant populations were collected and tested for infectability by pseudotyped luciferase reporter virus (100 ng p24 per infection). For antibody blocking experiments, cells were preincubated with anti-CD4 mAb (Leu3a, Becton Dickinson) at 10 μg/ml for 1 hour before infection with virus. Anti-CD4 was maintained during infection at 5 ug/ml. For chemokine blocking experiments, cells were preincubated with a mixture of MIP-1α, MIP-1β, and RANTES (each at 1 μg/ml). After 30 minutes, an equal volume of reporter virus was added without additional chemokines, and luciferase activity was measured 2 days later. For the calcium mobilization assays, cells were loaded with the calcium indicator indo-1/AM at 2 mM in complete growth medium at 20° C. for 45 minutes. Cells were then washed, resuspended in Na-HBSS (in mM: 2 CaCl$_2$, 145 NaCl, 5 KCl, 1 MgCl$_2$, 5 d-glucose, 20 HEPES; pH 7.3) containing 1% BSA and maintained at 20° C. for up to two hours. Fluorescence measurements to determine $[Ca^{2+}]_i$ were made from approximately $5 \times 10^5$ cells suspended in 2 ml Na-HBSS and maintained at 37° C. in a constantly stirred acrylic cuvette using a Photon Technologies Inc. spectrofluorimeter. The excitation wavelength was 350 nm (4 nm bandwidth) and dual simultaneous monitoring of emission at 405 and 485 nm (10 nm bandwidth) was employed. The ratio of emission at 405/485 nm was measured at a rate of 2 Hz.

293T cells were transfected with equal amounts of pcDNA1-based Env and pcRev expression vectors. Two days later the transfected cells ($1.5 \times 10^5$) were seeded with 3T3-T4-CKR5 or 3T3-T4-fusin ($3.0 \times 10^5$) cells. The next day the cells were stained with Giemsa stain. Syncytia were counted and plates were photographed.

Results and Discussion

Figure 1A:
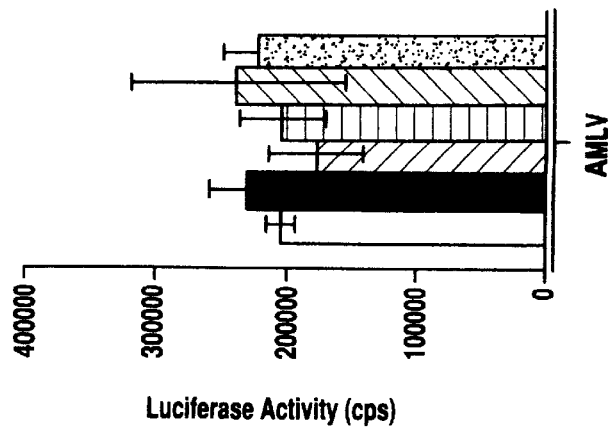

Chemokines block entry of primary HIV-1. To test whether β-chemokines block entry of macrophage-tropic HIV-1, the T cell line PM1 is infected with HIV-1-based luciferase reporter viruses. PM1 cells are highly susceptible to infection with both macrophage-tropic and T-tropic virus. The luciferase reporter viruses infect cells in a single round but are not competent for further replication because of a frameshift mutation inserted into env. Thus, measurement of luciferase activity in cells infected with pseudotypes of this virus permit comparison of the relative efficiency of entry mediated by different Envs. In these studies, HXB2 is used as a representative T-tropic Env, whereas JRFL, ADA, and BaL, are used as macrophage-tropic Envs. In addition, to control for possible post-entry or nonspecific effects of β-chemokines, virus pseudotyped with amphotropic murine leukemia virus (A-MLV) Env is prepared. The β-chemokines inhibited infection of PM1 cells with virus pseudotyped by macrophage-tropic Env (JRFL, ADA, BaL). However, the chemokines have no effect on infection with virus bearing T-tropic (HXB2) or A-MLV envelopes (FIG. 1). Strongest blocking is observed with RANTES, while MIP-1β and MIP-1α followed in order of effectiveness. MCP-3 and eotaxin have no inhibitory effect (FIG. 1 and data not shown). This same order is observed in inhibition of primary HIV-1 replication by β-chemokines. Taken together, these findings indicate that β chemokine inhibition of viral replication is due to prevention of entry of macrophage-tropic HIV-1, but not T-tropic HIV-1.

CC-CKR-5 is a potent co-receptor for macrophage-tropic virus. The known β-chemokine receptors, including fusin, are expressed in several human and murine cell lines and then their relative infectivity is tested using HIV-luciferase pseudotyped with the different envelope glycoproteins. Human embryonic kidney 293T cells transiently transfected with both CD4 and the different chemokine receptors are readily infected with virus pseudotyped with amphotropic and T-tropic envelope glycoprotein, but not with virus lacking envelope glycoprotein (FIG. 2a). Cells transiently transfected with expression vectors for CD4 plus CC-CKR-1, CC-CKR-2B, CC-CKR-3, or CC-CKR-4 are resistant to infection with virus pseudotyped with macrophage-tropic envelopes when compared to vector-transfected control cells (FIG. 2a). However, surprisingly cells co-expressing CD4 and CC-CKR-5 display an increase of three to four orders of magnitude in sensitivity to infection with viruses pseudotyped by ADA, BaL or JRFL envelope glycoproteins (FIG. 2a). Nearly identical findings were observed for CC-CKR-5 cDNAs amplified from three different individuals.

Figure 3B:
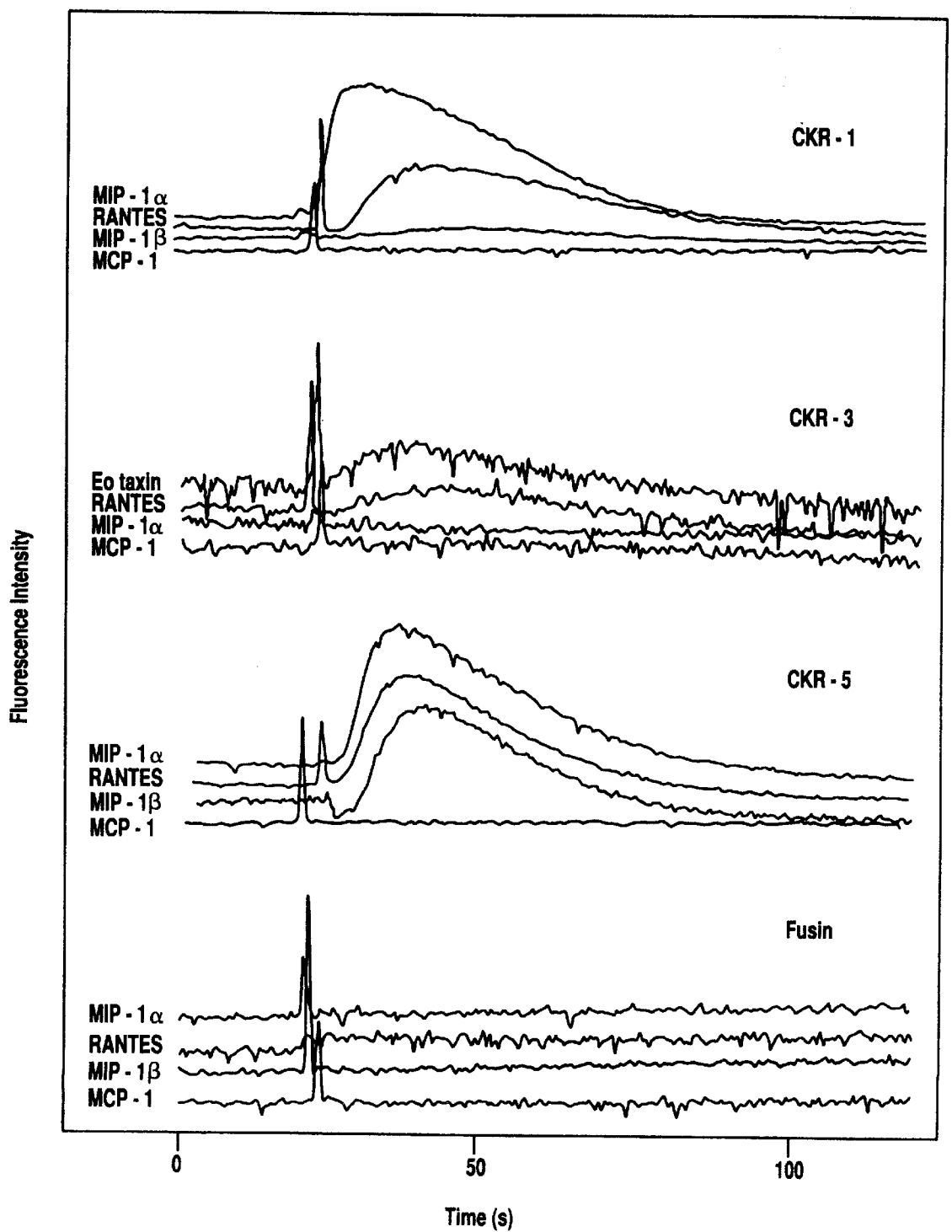

Infection of the 293T cells expressing both CD4 and CC-CKR-5 is completely blocked by the anti-CD4 monoclonal antibody Leu-3a (FIG. 2b). In addition, when pcCD4 is omitted from the transfection, CC-CKR-5 failed to support virus entry (FIG. 2c). Taken together, these findings indicate that CC-CKR-5 and CD4 must function cooperatively to mediate entry of macrophage-tropic virus. Murine cells transfected with human CD4 are resistant to infection with all tested strains of HIV. To determine whether chemokine receptors could confer susceptibility to infection, the different receptor genes are stably introduced into murine 3T3.CD4 cells. Cells expressing CC-CKR-1, CC-CKR-2B, CC-CKR-3, CC-CKR-4, Duffy, or fusin are all resistant to infection with HIV-luciferase pseudotyped with macrophage-tropic Envs, but are infected with virus bearing amphotropic Env (FIG. 3a and data not shown). Expression of CC-CKR-5 permitted infection with the macrophage-tropic pseudotypes, but these cells are resistant to infection mediated by HXB2 Env (FIG. 3a). Only fusin-expressing 3T3.CD4 cells are permissive for infection with this T-tropic virus (FIG. 3a). The chemokine receptors are expressed on the surface of the 3T3.CD4 cells, as assessed by mobilization of intracellular free Ca$^{++}$ in response to the appropriate chemokines (FIG. 3b and data not shown). Cells expressing CC-CKR-5 responded to RANTES, MIP-1α and MIP-1β, consistent with known β-chemokine reactivities. Infection of the 3T3.CD4 cells expressing CC-CKR-5 with macrophage-tropic virus is blocked by a mixture of the three chemokines that efficiently activate this receptor as well as by anti-CD4 antibody (FIG. 3a). Infection of the fusin-expressing cells with T-tropic virus is also blocked by anti-CD4, but is completely refractory to treatment with chemokines. Thus, these results suggest that only CC-CKR-5 mediates entry of macrophage-tropic Envs, that T-tropic envelope glycoproteins do not use this co-receptor for entry, and that β-chemokines block entry of the macrophage-tropic virus by specifically binding to this receptor.

Figure 3C:
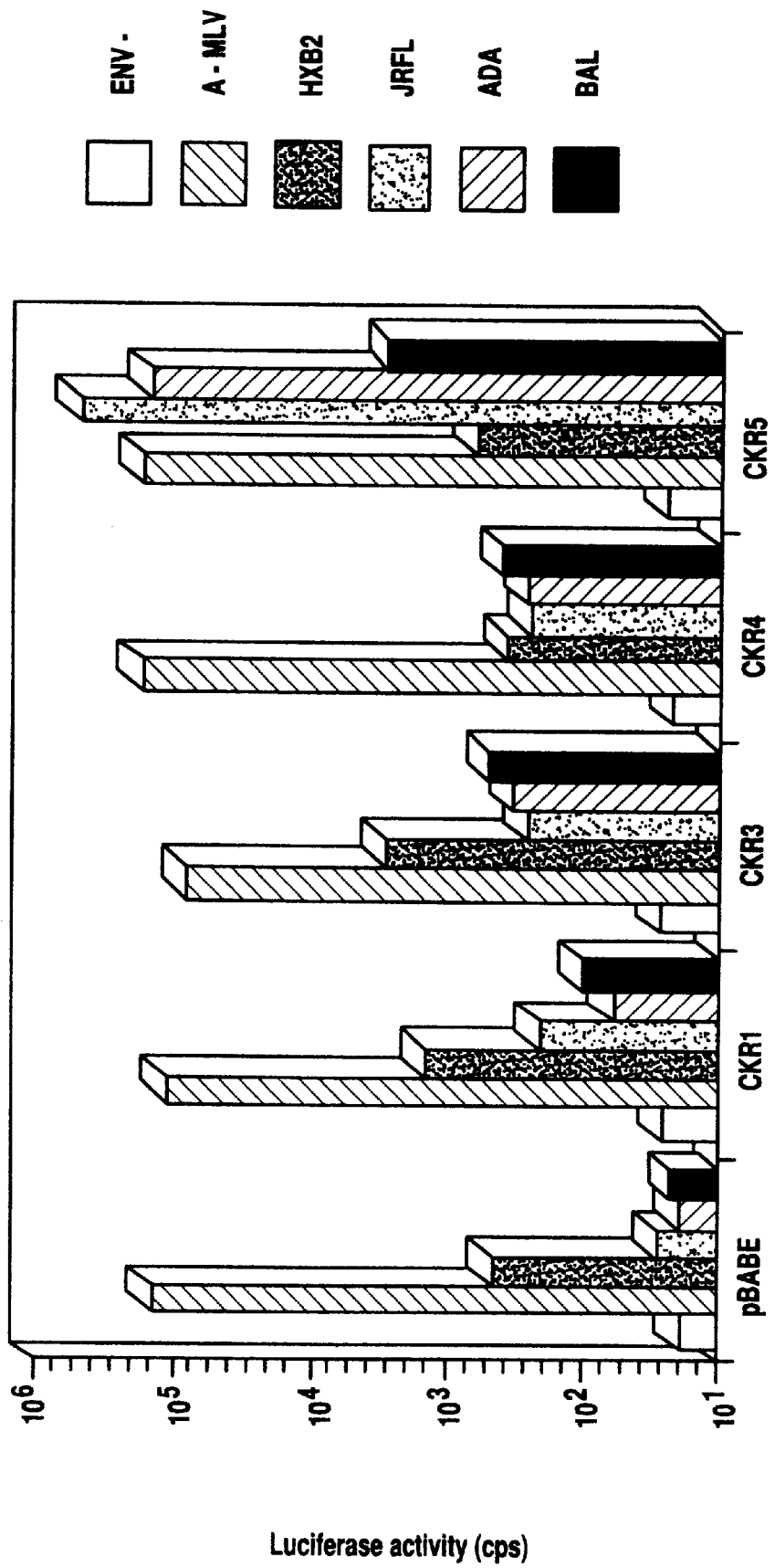
Figure 4A:
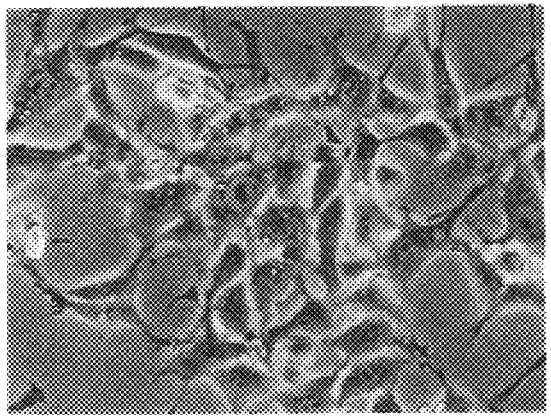
Figure 4B:
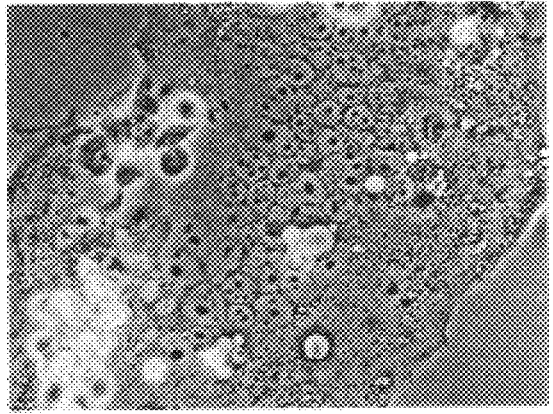
Figure 4C:
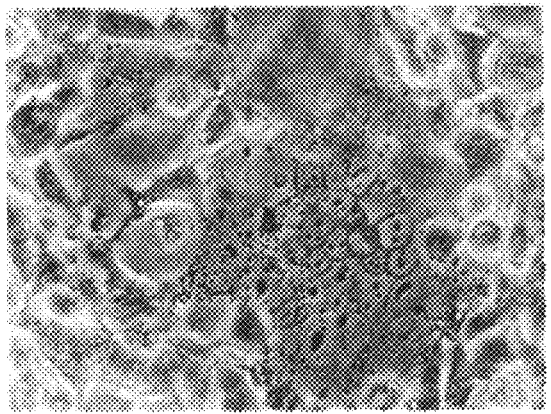
Figure 4D:
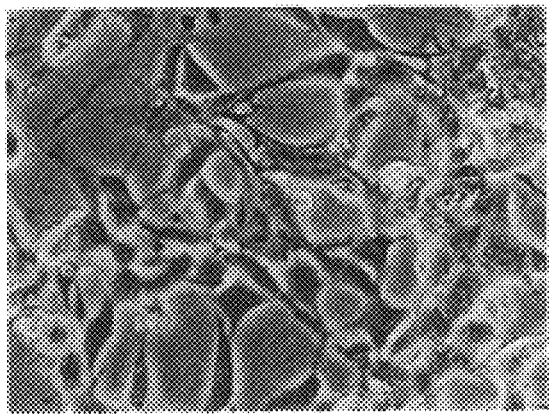

Stable expression of CC-CKR-5, but not of the other β-chemokine receptors, in human HOS.CD4, HeLa.CD4, and U87MG.CD4 cells also conferred upon these cells susceptibility to infection with macrophage-tropic HIV-1 (FIG. 3c, 3d and data not shown). As observed in the transient transfections, stable co-expression of both CC-CKR-5 and CD4 is required for viral entry into the HeLa cells (FIG. 3d). Infection of these cells with macrophage-tropic virus is reduced by 70–80% upon treatment with a mixture of chemokines (FIG. 3d). High levels of β-chemokines failed to inhibit infection of HOS.CD4 cells (data not shown). In general, inhibition with β-chemokines is consistently less efficient in the non-lymphoid cells expressing CD4 and CC-CKR-5 than in the PM1 cells.

CC-CKR-5 promotes Env-mediated fusion. Fusion of the HIV-1 envelope with the cellular plasma membrane can be simulated by co-cultivating cells expressing envelope glycoprotein with human cells that express CD4, thus resulting in formation of syncytia. Murine cells expressing human $CD4^+$ fail to support this fusion. Expression of fusin renders murine cells fusogenic for cells expressing T-tropic, but not macrophage-tropic Env. To test whether CC-CKR-5 would support fusion with cells expressing macrophage-tropic Env, 293T cells are transfected with different Env expression vectors and co-cultivated overnight with cell lines stably expressing transfected CD4 and CC-CKR-5 genes. As shown in FIG. 4, 293T cells expressing JRFL Env formed large syncytia with murine 3T3.CD4 cells expressing CC-CKR-5, but not with cells expressing fusin. Conversely, 293T cells expressing HXB2 Env fused to cells expressing fusin, but not to cells expressing CC-CKR-5. Similar results are obtained with U87MG.CD4 cells transfected with either fusin or CC-CKR-5 (not shown). Thus, macrophage-tropic Env-mediated fusion occurs in a manner that is highly specific for the entry cofactor.

EXAMPLE 2

Replication of Macrophage-tropic Virus in Cells Expressing CC-CKR-5

Materials and Methods

HIV-HSA is based on the T-cell line adapted virus pNL4-3, but contains, in place of nef, the gene encoding the small cell surface protein, heat stable antigen (HSA or CD24). HIV(BAL)-HSA virus is similar except that its env gene has been replaced by the Sal-I-Bam-HI restriction fragment containing the macrophage-tropic Env of BaL. HIV(BaL) HSA replicates in PM1 cells but not in CEM cells, while HIV(HSA) replicates in both cell types (data not shown). Both viruses show a characteristic bimodal distribution of HSA staining cells. This is likely reflect whether the cells are in the early or late phase of the replication cycle.

Results

Figure 5A:
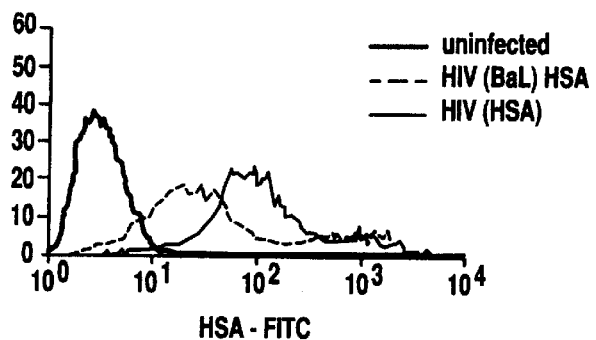
Figure 5B:
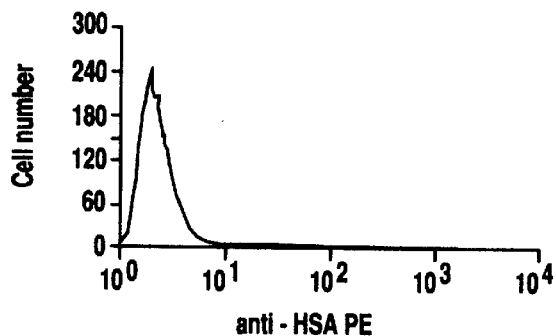
Figure 5C:
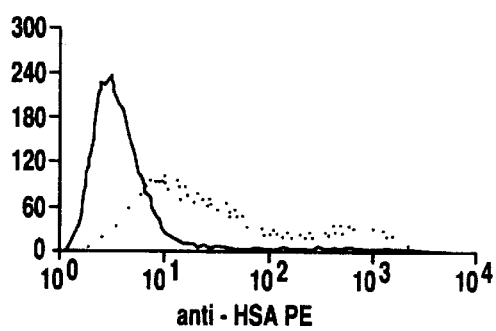
Figure 5D:
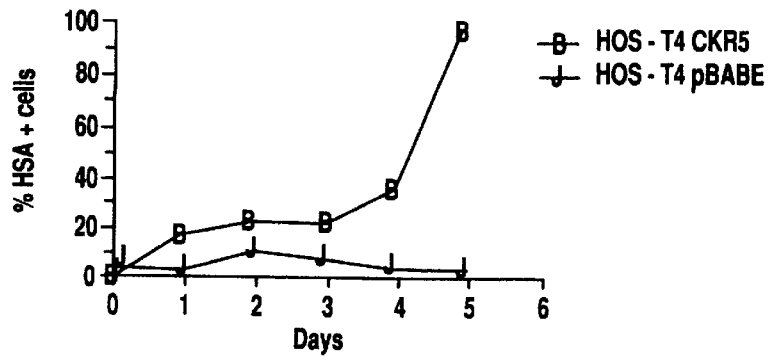

To test whether CC-CKR-5 expression allows for full replication and spread of macrophage-tropic virus, HOS.CD4 cells expressing CC-CKR-5 and control cells (HOS.CD4-BABE, transduced with the puromycin-resistance vector alone) were infected with the replication-competent reporter viruses HIV-HSA and HIV(BaL)-HSA. Both viruses are based on the T-cell line-adapted virus NM4-3, but the latter contains the BaL macrophage-tropic Env. Both viruses replicate in PM1 cells (FIG. 5a) but HIV(BaL)HSA fails to replicate in T-cell lines such as CEMX174 cells and in HOS.CD4 (data not shown). The viruses contain the gene for heat stable antigen (HSA; CD24) in place of nef, allowing for quantitation of the infected cells by fluorescence activated cell sorting (FACS) after staining with anti-HSA monoclonal antibody. The HOS.CD4-BABE cells remain uninfected with both viruses six days after infection (FIG. 5B), but nearly all of the HOS.CD4-CKR5 cells are infected with HIV(BaL)-HSA (FIG. 5C). Sampling of the HIV(BaL)-HSA infected cultures over a several day period indicate that an increasing percentage of the cells become infected over time, confirming, the ability of the virus to spread in the culture (FIG. 5D). HIV-HSA fail to replicate in the HOS.CD4-CKR5 cultures, consistent with the restriction of this T-tropic virus to utilizing fusin, which is likely to be limiting in these cells. Expression of CC-CKR-5 in 3T3.CD4 cells also permits HIV(BAL)HSA virus replication, but this is rather limited, presumably due to inefficient viral gene expression in murine cells (data not shown).

EXAMPLE 3

CC-CKR-5 is Expressed in Primary T-cells and Macrophages

Materials and Methods

Total RNA was prepared from the indicated cell-types using Triazol reagent (Gibco/BRL), treated with RNase-free DNase (Boehringer-Mannheim) and used in reverse-transcriptase-PCR reactions. First strand cDNA was primed with oligo-dT using Superscript reverse transcriptase as per manufacturer's direction (Gibco/BRL) and products were amplified with primers hybridizing to the 5' and 3' untranslated regions of CC-CKR-5 (upstream CTCGGATCCG-GTGGAACAAGATGGATTAT; downstream CTCGTCGACATGTGCACAACTCTGACTG) or to glyceraldehyde-3-phosphate dehydrogenase using a Taq/Pwo polymerase mixture (Boehringer Mannheim) To control for the presence of genomic DNA, control cDNA reactions in which reverse transcriptase was omitted were prepared in parallel. These were uniformly negative (data not shown).

Results

The initial description of the CC-CKR-5 gene suggested that its expression is limited to granulocyte precursors, and absent in peripheral blood cells (PBMC). To be a major co-receptor in vivo, however, this molecule would be expected to be expressed in T-cells and monocyte/macrophages, the predominant cell-types targeted by the virus. Northern blot analysis with CC-CKR-5 cDNA as probe does not readily distinguish between CC-CKR-5 and the closely related CC-CKR-2 transcripts. Reverse-transcriptase PCR is performed on isolated subsets from PBMC. CC-CKR-5 transcripts are detected in both the monocyte/macrophage and macrophage-depleted CD4+ fractions (FIG. 6). In addition, it is found that PM1 and HUT78 cells both express the gene. Significantly more CC-CKR-5 transcript is detected in PM1 cells, consistent with the higher infectivity of these cells by macrophage-tropic and primary HIV-1 isolates.

CC-CKR-5 thus acts as a potent co-receptor, in concert with CD4, to permit entry of macrophage-tropic HIV-1 into cells. Both CD4 and CC-CKR-5 are required for viral entry to proceed, just as CD4 and fusin are required for entry of T cell line-adapted virus. Co-receptor usage appears to be highly sequence specific since the other known members of the β-chemokine receptor family, including CC-CKR-1, 2B, 3, 4, and Duffy antigen show no detectable co-receptor activity for either macrophage- or T-tropic envelope glycoproteins in the viral strains tested. Since a variety of human and murine cells transfected with human CD4 and CC-CKR-5 are efficiently infected with macrophage-tropic virus, this combination of surface molecules is likely to promote infection with primary strains of HIV-1 in vivo. Although the precise expression pattern of CC-CKR-5 is not presently known, it is expressed in T lymphocytes, and the data suggest that it is also present in monocytes and macrophages. However, it remains possible that in these cells a yet unidentified co-receptor is active. Moreover, T-cells could express related proteins other than those tested that could in some cases be used as co-receptors.

The macrophage tropic envelope glycoproteins that are used are derived from virus after limited growth in PBMC and are therefore likely to reflect co-receptor use similar to that of primary virus. This suggests that CC-CKR-5 serves as a major co-receptor for primary macrophage-tropic strains of HIV-1 in vivo. This co-receptor may also be active during HIV-1 transmission, as suggested by the strict predominance of macrophage-tropic virus early in infection. In this regard, a role for chemokine receptors in HIV-1 transmission is suggested by Paxton et al. who showed that the CD4+ cells of individuals to whom HIV-1 cannot be sexually transmitted produce unusually high levels of β-chemokines.

The finding of the role of CC-CKR-5 in macrophage-tropic virus entry, together with the recent identification of fusin as the co-receptor for entry of T-tropic viruses, resolves a long-standing puzzle as to the basis of envelope glycoprotein-related differences in HIV-1 tropism. The adaptation of primary HIV-1 isolates for growth in transformed T cell lines is thus likely to result from a selection for envelope glycoprotein sequences that use fusin rather than CC-CKR-5 as co-receptor. Likewise, the well-documented in vivo phenotypic switch from macrophage-tropic (or NSI) to T-tropic (SI) viruses that occurs in many infected individuals prior to an increase in severity of the disease could be the result of a change in co-receptor usage from CC-CKR-5 to fusin. The appearance of fusin-specific virus could allow for continued virus replication in the presence of high levels of β-chemokine or could result in infection of a wider variety of cell types. With the new tools now available, it will now be possible to carefully evaluate the receptor usage of viruses sampled at different stages of HIV disease progression.

The basis for the change in receptor usage is likely to be determined, at least in part, by changes in specific sequences within the V3 loop of gp120, which has been shown to have a key role in HIV-1 tropism. Furthermore, CD4 binding appears to induce a conformational change in the envelope glycoprotein that increases exposure of the V3 loop. Based on these findings, it is determined that CD4 binding induces a conformational change in Env that exposes a co-receptor binding domain. This domain would then interact with specific amino acid residues on an adjacent co-receptor molecule. A successful interaction would trigger a conformational change in gp41, releasing its amino terminal hydrophobic peptide to initiate membrane fusion. Such a mechanism has precedent in the low pH-mediated activation of influenza hemagglutinin.

A required interaction between CD4 and the chemokine receptor could involve only the first two immunoglobulin-like domains of CD4, since the other domains are dispensable [Bedinger et al. Nature 334, 162–165 (1988)]. It can also involve the signaling through the chemokine receptor which can be a means of HIV-1 entry and/or a means for a subsequent event in viral replication. The mechanism of chemokine blocking can involve steric hindrance or desensitization of the receptor through down-regulation or conformational changes. The inefficient chemokine blocking that is observed with several cell lines indicates that competition for a binding site on the receptor is not sufficient. Finally, a there can be a role for the members of the chemokine receptor family that can interact with HIV envelope glycoprotein in aberrant signal transduction resulting in elimination of T helper cells late in the disease process.

EXAMPLE 4

Homozygous Defect in HIV-coreceptor Accounts for Resistance to HIV Infection

Rare individuals have been multiply exposed to HIV-1 but remain uninfected. The CD4+ T-cells of two of these individuals, designated EU2 and EU3, are highly resistant in vitro to the entry of primary macrophage-tropic virus, but are readily infectable with transformed T-cell line adapted viruses. The present invention is based, in part, on identification of the genetic basis of this resistance. CD4+ T-cells of some of these individuals resist high doses of virus in vitro. Of 25 exposed/uninfected (EU) individuals studied, the CD4+ T-cells [Paxton et al., Nat. Med. 2: 412–417 (1996)] and macrophages [Connor et al., J. Virol. Submitted (1996)] of EU2 and EU3 required about 1,000-fold more virus to establish infection than control cells from unexposed donors. While a small fraction of the cells did become infected with this high inoculum, the virus failed to replicate further. Analysis of the early events of the viral replication cycle showed that macrophage-tropic HIV-1 isolates failed to enter or fuse to the CD4+ cells of these two individuals. Thus, the resistance of these individuals to sexual transmission of HIV-1 was likely to have resulted from the inability of their cells to support entry of macrophage-tropic virus. EU2 and EU3 were found to have a homozygous defect in the gene encoding the recently described coreceptor for primary HIV-1 isolates, CKR-5. These individuals appear to have inherited a defective CKR-5 allele that contains an internal 32 base pair deletion in the region corresponding to the second extracellular loop of the protein. The encoded protein is severely truncated and cannot be detected at the cell surface. Surprisingly, this defect has no obvious phenotype in the affected individuals. However, the individuals are resistant to macrophage-tropic virus. Thus, a mutant CKR-5 allele present in the human population appears to protect rare homozygous individuals from sexual transmission of HIV-1. These findings indicate the importance of CKR-5 in HIV-1 transmission and suggest that targeting the HIV-1-CKR-5 interaction may provide a means of preventing or slowing disease progression.

Materials and Methods

RT-PCR and DNA sequencing. Total cellular RNA was prepared using Triazol (GibcoBRL) according to the manufacturer's instructions and treated with 10 units RNAase-free DNAase (Boehringer-Mannheim). Oligo-dT-primed cDNA was prepared from 5 µg RNA using Superscript reverse transcriptase (GibcoBRL) according to the manufacturer's instructions and resuspended in 80 µl TE (10 mM tris, pH 8.0, 1 mM EDTA). Aliquots of the cDNA (5.0 µl) were amplified with Taq polymerase (Boehringer-Mannheim) by 5 cycles of PCR (94°, 30 s; 55°, 45 s; 72°, 90 s) followed by an additional 35 cycles (94°, 30 s; 62°, 45 s; 72°, 90 s) in a volume of 50 µl using primers hybridizing to the 5' and 3' untranslated regions of CKR-5. The reaction products (10 µl) were separated on 4% MetaPhor agarose (FMC) in the presence of 0.5 µg/ml ethidium bromide and photographed. A control amplification containing no added DNA was included in each experiment reaction. No PCR product was detected in these reactions. For cloning of amplified cDNAs, PCR was carried out similarly except that instead of Taq polymerase a high fidelity Expand polymerase (Boehringer-Mannheim) was used for a total of 37 cycles. Amplified products were digested with BamHI and SalI restriction enzymes for CKR-5 or HindIII and XhoI for fusin. CKR-5 cDNAs were cloned into the cytomegalovirus promoter-driven expression vector pcDNA1/amp (Invitrogen Corporation). Fusin cDNAs were cloned into the retroviral expression vector pBABE-puro [Morgenstern and Land, Nucl. Acids Res. 18: 3587–3596 (1990)]. Nucleotide sequencing of the cloned cDNAs was determined by the dideoxy method on both strands using primers shown in FIG. 9B. Upstream and downstream oligonucleotide primers for amplifying and cloning were as follows: CKR-5: 5'-CTCGGATCCGGTGGAACAAGATGGATTAT (SEQ ID NO: 2), 5'-CTCGTCGACATGTGCACAACT CTGACTG (SEQ ID NO: 3; fusin, 5'-GGCTAAAGCTTGGCCTGAGTGCTCCAGTAGCC (SEQ ID NO: 4); 5'-CGTCCTCGAGCATCTGTGTTAGCTGGAGTG (SEQ ID NO: 5); CKR-1, 5'-GCGGATCCCAAAG TCCCTTG-GAACCAGAG (SEQ ID NO: 6), 5'-GGTCTAGACAGGCCACCATTACATTCCCT (SEQ ID NO: 7).

Coreceptor activity analysis. Transient assay for CKR-5 coreceptor activity has been previously described. Briefly, 293T cells were transfected by $CaPO_4$ coprecipitation with a mixture of pcCKR5 and pcCD4 (10 µg each) as described. The next day the cells were transferred to 24 well tissue culture dishes ($1\times10^4$/well) and the following day the cells were infected with luciferase reporter viruses (10 ng $p24^{gag}$). Reporter viruses pseudotyped by macrophage-tropic, T-tropic, or amphotropic Envs were prepared by transfecting 293T cells with NL-Luc-Env⁻ and the appropriate Env expression vector (10 µg each) and quantitated as previously described and frozen in aliquots at −80° C. Lysates (100 µl) were prepared two days later and luciferase activity in 20 µl was measured with commercial reagents (Promega) with a Packard Topcount scintillation counter. Fusin coreceptor activity was measured in a stable assay as described previously. Briefly, retrovirus stocks were prepared from the pBABE-puro fusin plasmids using the method of Landau and Littman [Landau and Littman, J. Virol. 66: 5110–5113 (1992)]. HOS-T4 (human osteosarcoma cells expressing human CD4) were infected with the pBABE-puro viruses (2 mls supernatant). Two days later the cells were selected in 1.0 µg/ml puromycin. When the cells became confluent (about 5–7 days later) the cells were infected with luciferase reporter viruses and luciferase activity was measured as described above for the transient assay.

Southern and PCR analysis of genomic DNA. Genomic DNA was purified from cell lines and PBMC by standard methods. DNA (10 µg) was cleaved with restriction enzyme and separated by electrophoresis on 2% agarose gels. The DNA was transferred to nitrocellulose filters and hybridized to a BamHI-SalI cleaved CKR-5 cDNA insert labeled with [$\alpha$-$^{32}$P]dCTP by the random primer method using commercial reagents (Boehringer-Mannheim). PCR of genomic DNA was as described above for cDNA except that 0.5–1 µg of genomic DNA was used instead of reverse transcriptase product. The PCR primers SP4.760 (5') CTTCATTACAC-CTGCAGCTCT (SEQ ID NO: 8) and PM6.942 (3') CACAGCCCTGTGCCTCTTCTTC (SEQ ID NO: 9) were used to amplify a 182 base pair fragment of the DNA flanking the deletion site from wild type genes, and a corresponding 150 base pair fragment (iwth the 32 bases deleted) from mutant genes. Amplified products were separated on 4% MetaPhor agarose (FMC) and visualized by ethidium bromide staining.

FACS and immunoblot analysis. A CKR-5 expression vector containing an HA epitope-tag [Field et al., Molec. Cell. Biol. 8: 2159–2165 (1988)] near the amino-terminus was constructed using wild-type or EU cell-derived CKR-5. These plasmids were mixed with an equal amount (10 µg each) of pcCD4 [Lenburg and Landau, J. Virol. 67, 7238–7245 (1993)] and then used to transfect 293T cells. After two days, the $0.5\times10^6$ cells were stained with 0.5 µg monoclonal antibody (Mab) 12CA5 (BabCo), 0.2 µg phycoerythrin-conjugated rabbit anti-mouse immunoglobulin (Boehringer-Mannheim) and 0.5 µg FITC-conjugated anti-CD4 MAb Leu3a. Construction and characterization of the epitope-tagged wild-type CKR-5 will be reported elsewhere. The cells (10,000) were analyzed on a Becton-Dickenson FACScaliber. Neither antibody showed fluorescence levels above background on untransfected control 293T cells (not shown). Tagged CKR-5 was detected on imunoblots as described previously [Paxton et al., J. Virol. 67: 7229–7237 (1993)].

Chemokine-induced signal transduction measurement. PBMC were washed for 4 min in PBS, pH 3.0 to remove endogenously bound chemokines. In pilot experiments this removed 94% of the bound chemokine. The cells were centrifuged at 500×G for 5 min and resuspended in Hanks buffer for intracellular [$Ca^{2+}$] measurements. Intracellular [$Ca^{2+}$] was measured by spectrofluorimetry with Fura-2, as described [Neote et al., Cell 72: 415–25 (1993)] with the following modifications. Fura-2 was used at a 5 µM and $3\times10^6$ cells were used per assay.

HIV-1 growth curves. Replication of HIV-1 was measured as described previously [Paxton et al., 1996, supra]. Briefly, PBMC ($2\times10^5$) were from Ficoll purified leukocytes. The CD4⁺ cells were purified and stimulated with phytohemagglutinin for three days. HIV-1 SF162 (600 TCID) was added for at least 4 hrs and the cells were washed three times to remove input virus. Samples were removed for $p_{24}^{gag}$ quantitation by commercial ELISA (Abbot) at indicated days postinfection.

Results

Expression of coreceptors in EU-derived cells. At least two mechanisms could account for the resistance of EU cells to infection by macrophage-tropic viruses. Overproduction of β-chemokines in these cells could lead to receptor desensitization and down regulation of CKR-5, inhibiting its coreceptor function. Alternatively, a failure to synthesize functional cell surface coreceptor caused, for example, by inadequate transcriptional activity of the CKR-5 gene or alteration of the CKR-5 coding sequence could account for the resistance of these cells to infection. To assess the relative amounts of CKR-5 and other coreceptor transcripts in EU cells, we used reverse transcription-polymerase chain reaction (RT-PCR) to amplify CKR-5, fusin, and CKR-1 cDNAs from equivalent amounts of RNA isolated from four previously characterized EU or normal donor T-cell clones. EU2-derived cloned T-cell lines (EU2.11, EU2.15, EU2.16, EU2.17), and an EU3-derived T-cell clone (EU3.1) are resistant to macrophage-tropic virus, while two clones from unexposed control donors (LW4.39 and LW5.49) are sensitive to both macrophage-tropic and T-tropic virus (referred to as LW4.13 and LW5.8 in [Dragic et al., 1996, supra]. Clones EU2.11, EU2.15, and EU2.16, and EU3.1 were also found to be somewhat resistant to T-tropic virus, while clone EU2.17 was readily infectable [Dragic et al., 1996, supra]. Results of RT-PCR analysis showed that CKR-5, CKR-1, and fusin transcripts were at least as abundant in the EU2 and EU3 cells as in those of normal donors (FIG. 7). CKR-5 and CKR-1 transcripts appeared to be present at slightly elevated levels in EU cells as compared to controls, perhaps due to decreased negative feedback control of transcription of these genes. Thus, the resistance of EU2 cells to macrophage-tropic HIV-1 was unlikely to be due to the absence or insufficient expression of the coreceptor gene.

CKR-5 transcripts from EU cells do not encode active coreceptor. CKR-5 and fusin coreceptor function were shown to be sensitively detected in a transient transfection assay [Deng et al., 1996, supra]. In this assay, 293T human embryonic kidney cells are transfected with CD4 and CKR-5 expression vectors. The cells are then infected with single-cycle luciferase reporter virus derived from the HIV-1 provirus pNL-Luc-Env$^-$ [Connor et al., Virology, 206: 936–944 (1995)]. This vector is a modified form of the HIV-1 provirus NL4-3 in which a firefly luciferase gene replaces nef and a frameshift mutation has been inserted in env. As a result of the frameshift in env, the virus is restricted to a single-cycle of replication. Following infection and integration of this virus, the luciferase reporter gene is expressed, reflecting the efficiency with which the virus entered. Pseudotyping this reporter virus with different HIV-1 Envs allows measurement of the relative activity of different coreceptors. Reporter viruses pseudotyped by macrophage-tropic Envs JRFL, BaL or ADA are specific for CKR-5 while those pseudotyped by the T-tropic Env HXB2 use fusin for entry. Reporter virus pseudotyped by amphotropic murine leukemia virus (A-MLV) Env [Landau et al., J. Virol. 65: 162–169 (1991); Page et al., 1990, supra], which enters through a non-coreceptor pathway, was used in these experiments to rule-out post-entry effects on luciferase expression.

Figure 8A:
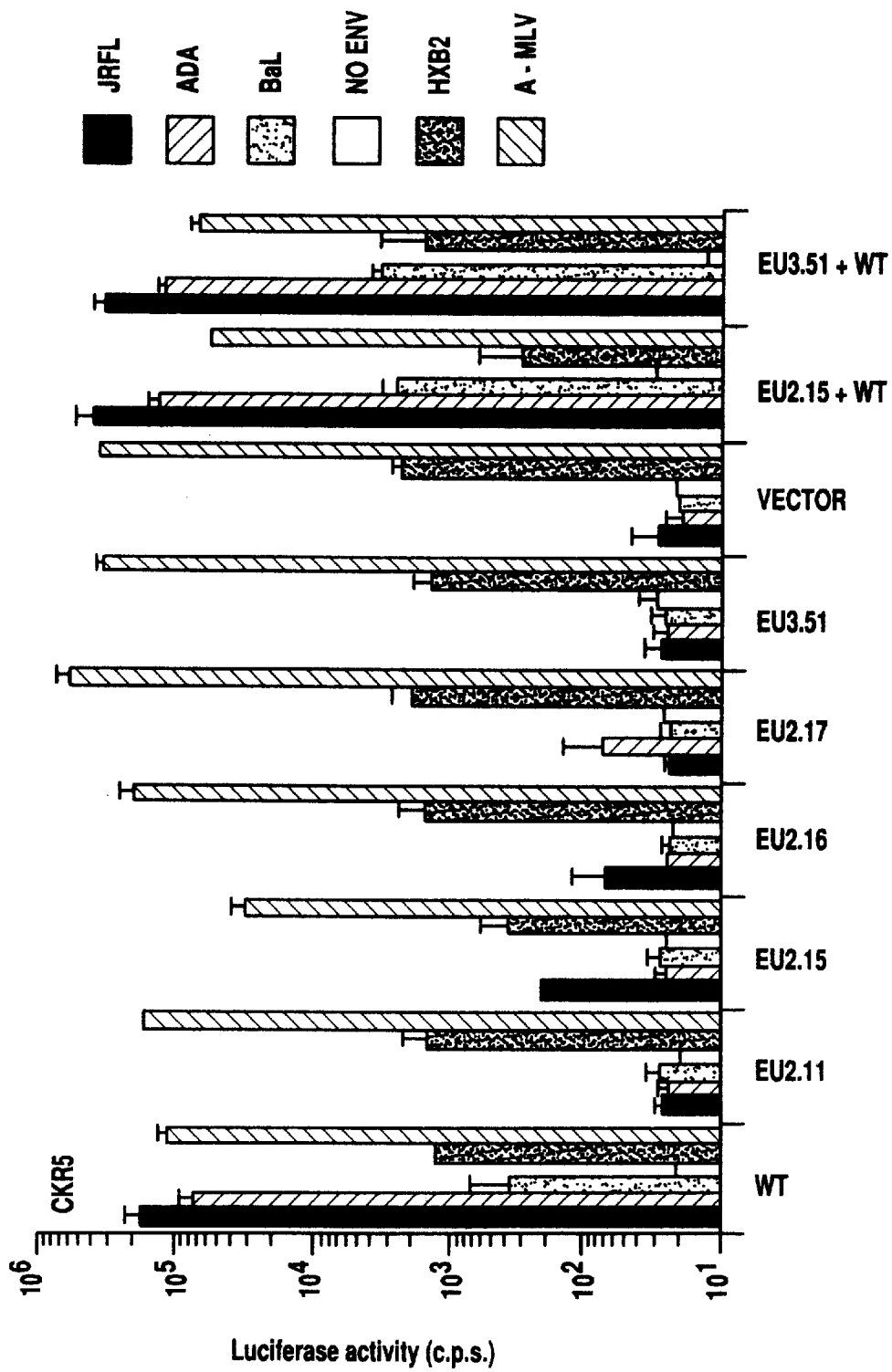

We used the transient transfection assay to test the coreceptor function of EU2 and EU3 CKR-5. CKR-5 cDNAs were amplified from EU2, EU3, or normal donor RNA by RT-PCR and cloned into the expression vector pcDNAI/amp. Each CKR-5 expression vector was then mixed with an equal amount of CD4 expression vector and used to transfect 293T cells. Coreceptor function encoded by each CKR-5 expression vector was measured by infecting the transfected cells with the panel of single-cycle luciferase reporter viruses. The results showed that the normal donor-derived CKR-5 expression vector encoded coreceptors that mediated efficient entry of macrophage-tropic virus (FIG. 8A, WT). In contrast, the CKR-5 expression vectors derived from each of the five EU2 and EU3 cell lines were inactive. The failure of these expression vectors to encode functional CKR-5 is not likely to have been the result of misincorporation during RT-PCR. RT-PCR amplified CKR-5 from control cells has in every case to date (at least four independent repetitions) resulted in functional CKR-5 cDNA. In addition, RT-PCR amplification of CKR-5 from EU2 or EU3 has not yielded a single functional cDNA in at least seven independent repetitions. Furthermore, fusin cDNA amplified from these same RNA preparations (described below) was uniformly active, arguing against a global defect in EU RNA. To determine whether the inactive CKR-5 cDNAs encoded a product with dominant negative activity, equal amounts of active and inactive CKR-5 expression vector were mixed with CD4 expression vector and used to transfect 293T cells. The addition of inactive CKR-5 vector did not reduce the coreceptor activity of the wild-type CKR-5 (FIG. 8A), arguing against a dominant negative role for the nonfunctional gene.

Figure 8B:
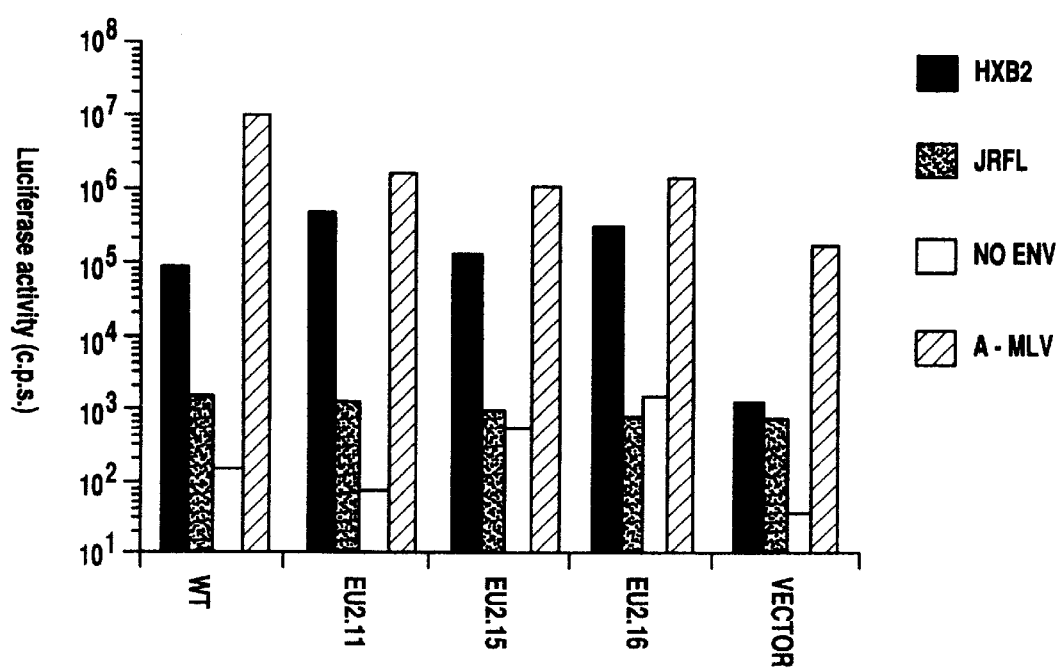

We used a similar approach to determine whether fusin derived from EU cells was active as a coreceptor. Fusin cDNAs were amplified by RT-PCR and cloned into the murine leukemia virus-based retroviral vector, pBABE-puro [Morgenstern and Land, 1990, supra]. These vectors were then used to establish HOS.CD4 [He and Landau, J. Virol. 69: 4587–4592 (1995)] (human osteosarcoma cells expressing CD4) stably expressing EU2-derived fusin. Coreceptor function of the expressed fusins was then determined by infecting the cells with luciferase reporter viruses. The results showed that EU-derived fusin cDNAs encoded coreceptors that mediated entry of T-tropic HIV-1 at levels comparable to that of the wild-type (FIG. 8B). Similar results were obtained with wain cDNA derived from EU3 (data not shown). Thus, the cells of these individuals are likely to contain fully functional fusin. The reason that some T-cell clones from EU2 support T-tropic virus replication at levels somewhat reduced to that of control cells [Dragic et al., 1996, supra] is not clear, but could be due to a slight decrease in the amount of coreceptor on the cell surface or to increased synthesis of the yet uncharacterized fusin ligand. In addition, CKR-1 cDNA amplified from EU2 RNA was fully active in mobilizing intracellular calcium upon binding to RANTES or MIP-1α (data not shown). These findings strongly suggest that EU2 and EU3 express CKR-5 mRNA that does not encode a functional HIV-1 coreceptor. Thus, the resistance of EU2 and EU3 to infection by macrophage-tropic HIV-1 strains is likely to be due to genetic alteration of CKR-5. Furthermore, the EU phenotype is not the result of a generalized defect in several coreceptors, but is likely to be restricted to a defect in CKR-5.

EU CKR-5 RNA contains a 32 base coding sequence deletion. To define the predicted genetic alteration, the nucleotide sequence of the complete 1,055 bp coding region of CKR-5 cDNA clones derived from EU2, EU3 and a normal donor was determined. Nucleotide sequences were determined on both strands using the set of primers shown in FIG. 9B. This analysis revealed an identical 32 bp deletion in each of the EU2 and EU3 cDNA. The deletion spans nucleotides 794 to 825 in a region corresponding to the second extracellular loop of the receptor (FIG. 9A). The deleted allele encodes a 215 amino acid protein (the wild-type receptor is 352 amino acids) in which the C-terminal 31 amino acids are translated out of frame. This deletion was present in all four independently amplified EU2 CKR-5 cDNAs and in the two EU3 cDNAs sequenced. Each of six cDNAs amplified from normal control T cell clones LW4.39 and LW5.49 was identical to wild-type CKR-5, as was a single CKR-5 amplified from PBMC of another control unexposed individual. In each EU-derived cDNA, no nucleotide changes were noted outside the 32 bp deletion, with a single exception. In one EU2-derived CKR-5 cDNA, a single G to A change at nt 559 that encodes an Arg to Lys change was found. This alteration was not present in any of the three other EU2 CKR-5 cDNAs sequenced and may have arisen by misincorporation during RT-PCR.

Figure 10:
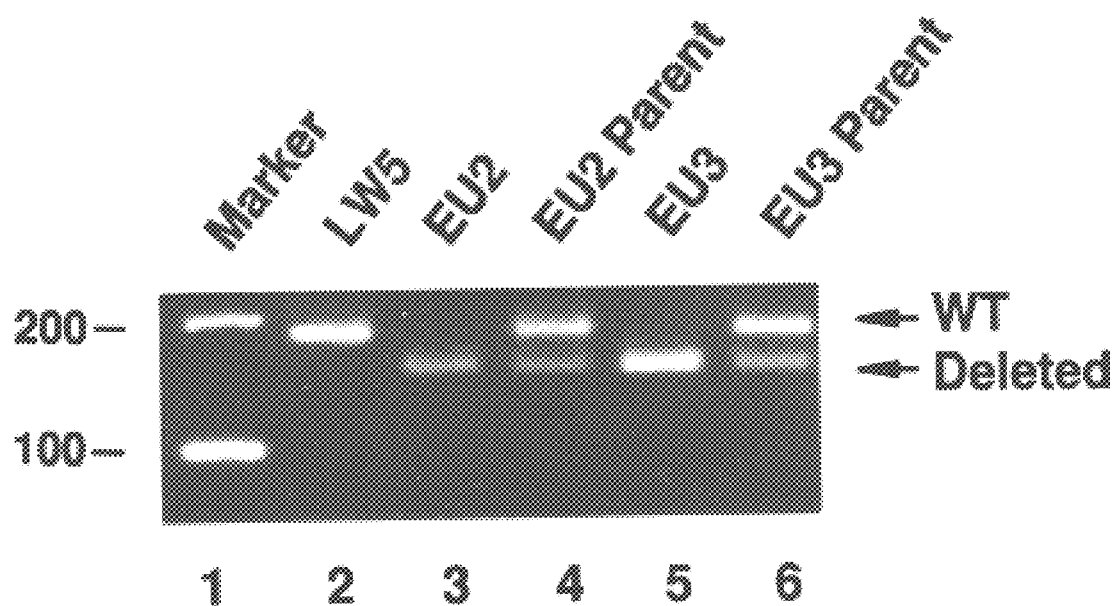

Defective CKR-5 is encoded in the genomic DNA and inherited. The 32 bp deletion found in EU CKR-5 RNA could have resulted from an aberrant splice to cryptic splice sites or could have been due to the presence of the deletion in the CKR-5 gene itself. To distinguish between these possibilities, we amplified a portion of CKYR-5 containing the deleted region from EU2, EU3 and control donor genomic PBMC DNA. PCR amplification using the flanking primers SP4.760 and PM6.942 (FIG. 9, bottom panel) yields predicted fragments of 182 bp and 150 bp for the wild-type and deleted alleles, respectively. PCR amplification from EU2 and EU3 genomic DNA with these primers showed only the 150 bp band (FIG. 10, lanes 3 and 5). In contrast, only the 182 bp band was amplified from LW5 control donor DNA. These findings confirmed the presence of the CKR-5 deletion in the genomic DNA of both EU individuals. In addition, we examined the CKR-5 alleles of 13 of the remaining 23 EU individuals in the cohort. Only one other individual's CD4$^+$ cells were highly resistant to infection and the genomic DNA of this individual had only deleted CKR-5. The other 22 samples were either fully or partially infectable [Paxton et al., 1996, supra] and of those tested, only wild-type CKR-5 allele was present (data not shown).

The absence of the wild-type 182 bp fragment in the EU DNA suggests that these individuals are either homozygous for the deletion or are hemizygous, containing a large deletion of one chromosome. To distinguish these possibilities, we tested the CKR-5 allele status of the genomic DNAs that were available in sufficient quantity. High molecular weight DNA isolated from PBMC of EU2, EU3 and EU3's parent and a normal donor was cleaved with EcoRI and BglII restriction endonucleases. This releases a 283 bp wild-type or 251 bp deleted fragment. Southern analysis confirmed that EU2 and EU3 DNA contains only the deleted allele, while the parent of EU3 has wild-type and deleted alleles (FIG. 10B).

The finding that two unrelated EU individuals have identically deleted CKR-5 alleles suggests that this mutation originated in a common ancestor and was inherited through the germline. Mendelian inheritance of these alleles would require that the parents of a homozygous EU individual are themselves either homozygous or heterozygous for the deletion. Alternatively, the deletion could have arisen de novo as the result of a recombination hot-spot. To distinguish between these possibilities, we determined the CKR-5 status of the available parental genomic DNA of these individuals. For both EU2 and EU3, the tested parent appeared to be heterozygous (FIG. 10, lanes 4 and 6), with one chromosome having the deleted and the other having the wild-type allele (DNA from the other parent of each individual was unavailable). Thus, it is likely that for both individuals each parent transmitted a deleted allele to their offspring. However, because of the unavailability of DNA from the other parent, we could not demonstrate this definitively.

To determine whether inheritance of the deleted CKR-5 allele could have been sex-linked in EU2 and EU3, both of whom are males, we determined the chromosomal localization of the gene. CKR-5 was amplified from genomic DNAs of two somatic cell hybrid mapping panels (data not shown). The first panel localized the CKR-5 gene to chromosome 3. The second, a panel of radiation hybrids [Naylor et al., Cell. Genet., 72: 90–94 (1996)], further localized the gene to the short arm of chromosome 3 in cytogenetic band 3p21. Thus, the CKR-5 is linked to other members of the chemokine receptor family including CKR-1, CKR-2, V28 and CMK-BRL1 that are also on 3p21 [Baggiolini et al., Int. J. Immunopharmacol. 17: 103–8 (1995); Combadiere et al., DNA Cell. Biol. 14: 673–680 (1995); Raport et al., Gene 163: 295–9 (1995)]. The autosomal localization of CKR-5 predicts that its inheritance is not sex-linked.

Figure 11:
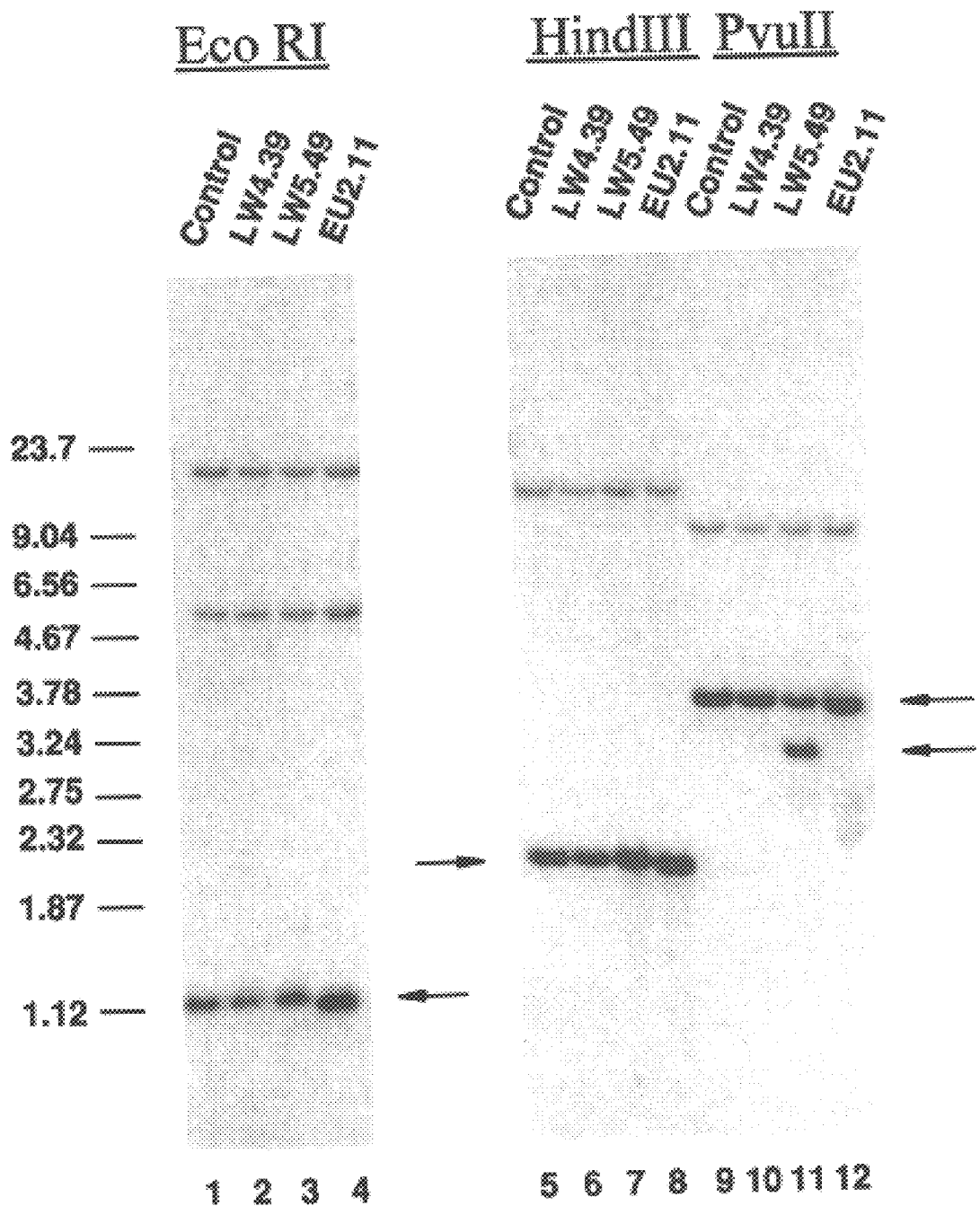

EU2 and EU3 are homozgous for the CKR-5 deletion. The analysis described above is consistent with a homozygous CKR-5 deletion in EU2 and EU3. However, it is equally consistent with a hemizygous status in which loss of a portion of one parental chromosome 3 resulted in complete loss of CKR-5. To distinguish between these possibilities, we analyzed the CKR-5 locus in normal donor and EU2 genomic DNA. Genomic DNAs from the PBMC of a normal donor, from two normal donor T-cell clones (LW4.39 and LW5.49) and from an EU2 T-cell clone was cleaved with EcoRI, PvuII, HindIII and hybridized to a full-length [$^{32}$P]-labeled CKR-5 probe. For all four genomic DNAs, the probe hybridized to bands of similar lengths with the following exceptions. First, EcoRI and HindIII digests of EU2 DNA showed CKR-5 fragments of 1.2 kb and 2.0 kb, respectively, that were slightly smaller than those of the control DNAs (FIG. 11, lanes 4 and 8, arrows). This decrease is consistent with the presence of the 32 bp deletion, further supporting the predicted presence of the deletion in the genomic DNA of EU2. Second, the CKR-5 of LW5.49 contains a PvuII restriction fragment length polymorphism (RFLP) (FIG. 11, lane 11). An additional PvuII site in this DNA results in the appearance of a 2.9 kb band in addition to the common 3.4 kb band. Both CKR-5 bands are decreased in intensity as compared to that of the other three samples (FIG. 11, compare lane 11 with lanes 9, 10 and 12). This decrease reflects the two-fold decrease in copy-number of each fragment in the heterozygote. Thus, the difference between a haploid or diploid CKR-5 content is detectable in this analysis. Similarly, in the EcoRI and HindIII digests the CKR-5 fragment of EU2 DNA is similar in intensity to that of the three control samples. In addition, Southern analysis of EU3 genomic DNA showed only the deleted CKR-5 fragment (data not shown). Taken together, these findings suggested that EU2 and EU3 were homozygous for the deleted allele and that no gross rearrangement of chromosome 3 was associated with the deletion.

Figure 12A:
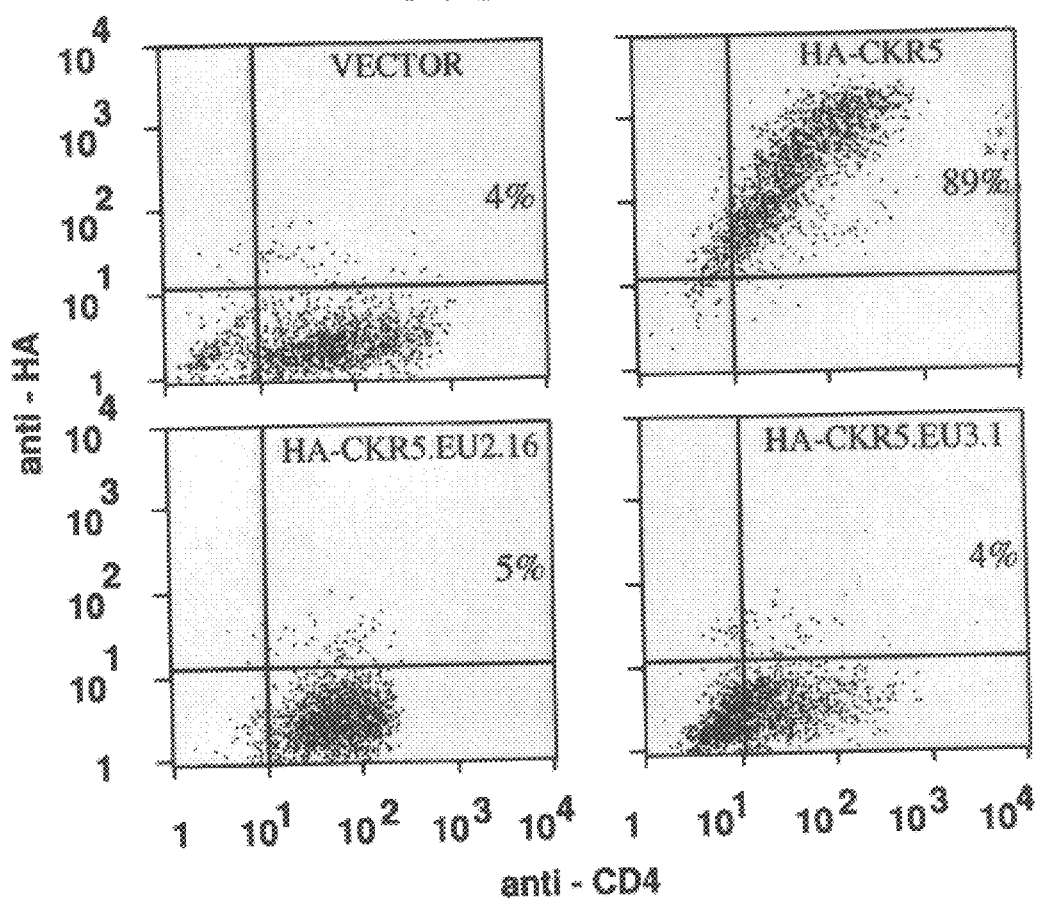
Figure 12B:
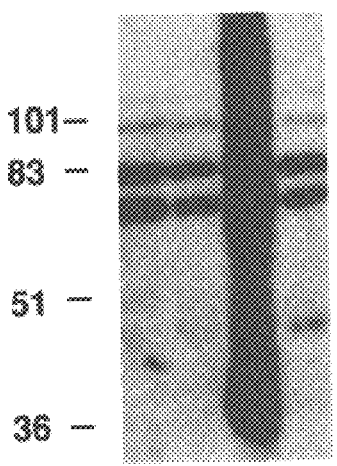

EU cells do not express functional CKR-5. We used two methods to investigate whether the EU cells expressed functional CKR-5. In the first, we tested whether epitope-tagged EU CKR-5 could be expressed on the cell surface. To do this, vectors expressing EU2, EU3, or wild-type influenza hemagglutinin (HA)-tagged CKR-5 were constructed. These were mixed with an equal amount of CD4 expression vector to control for transfection efficiency, and used to cotransfect 293T cells. FACS analysis of the cells stained with anti-HA Mab revealed that HA-tagged wild-type CKR-5 was expressed at the cell surface (FIG. 12A, upper right). Infection studies showed that this protein retained its coreceptor activity (data not shown). In contrast, HA-tagged CKR-5 derived from EU2 or EU3 was not detected (FIG. 12A, lower panels). Immunoblot analysis of the transfected cells suggested that the mutant protein was not stably expressed in the cytoplasm (FIG. 12B).

Figure 12C:
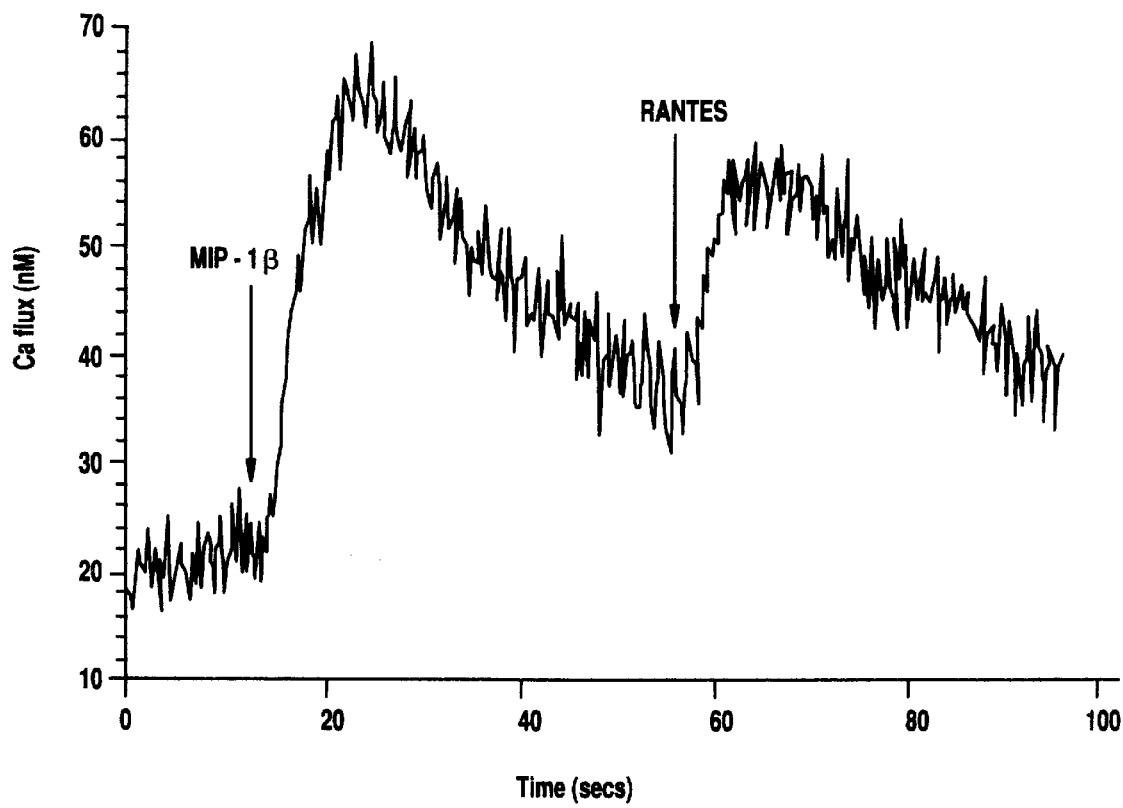
Figure 12D:
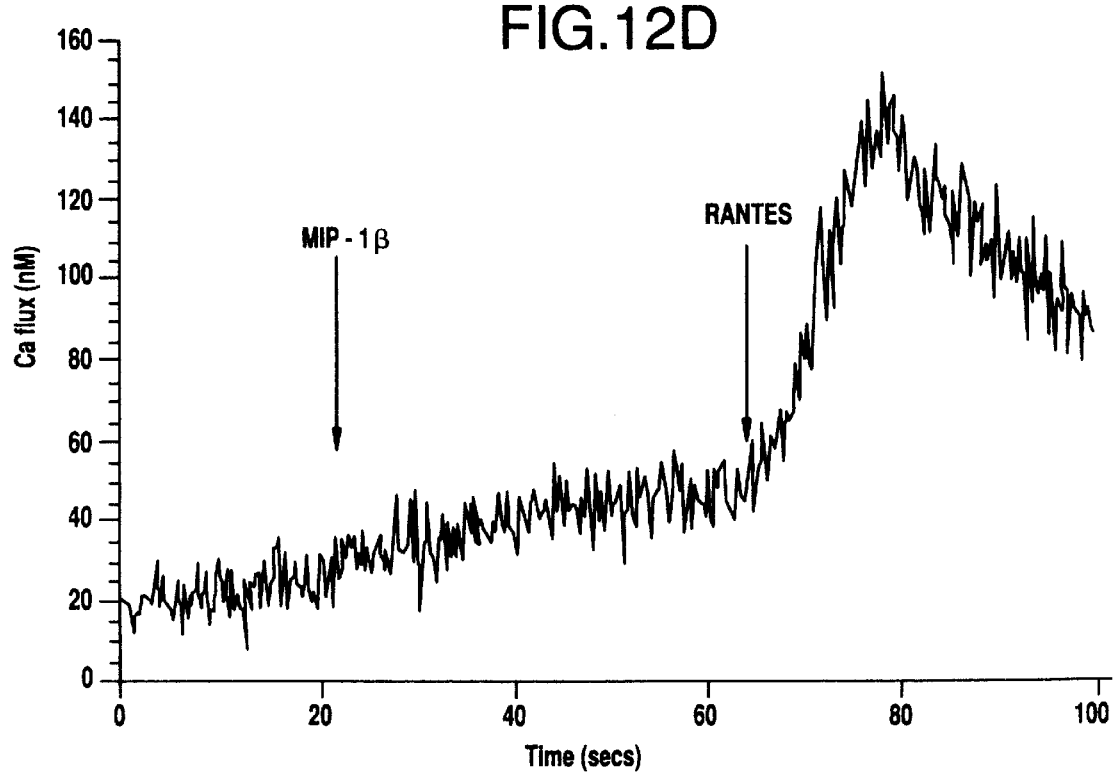

EU2 cells do not transduce CKR-5 mediated signals. To determine whether PBMC from EU individuals express functional chemokine receptors, we measured intracellular [$Ca^{2+}$] levels in response to challenge with the β-chemokines MIP-1β and RANTES. When control cells were loaded with the calcium probe Fura 2 and challenged with physiological concentrations of MIP-1β followed by RANTES, a rapid increase in intracellular [Ca$^{2+}$] was observed (FIG. 12C). In contrast, PBMC from EU2 were refractory to MIP-1β but responded to RANTES (FIG. 12d). Thus, EU2 cells do not transduce CKR-5-mediated signals yet are fully competent to transduce signals through other chemokine receptors. EU2 cells therefore do not have a generalized deficiency in their ability to transduce signals from other chemokine receptors.

Figure 13A:
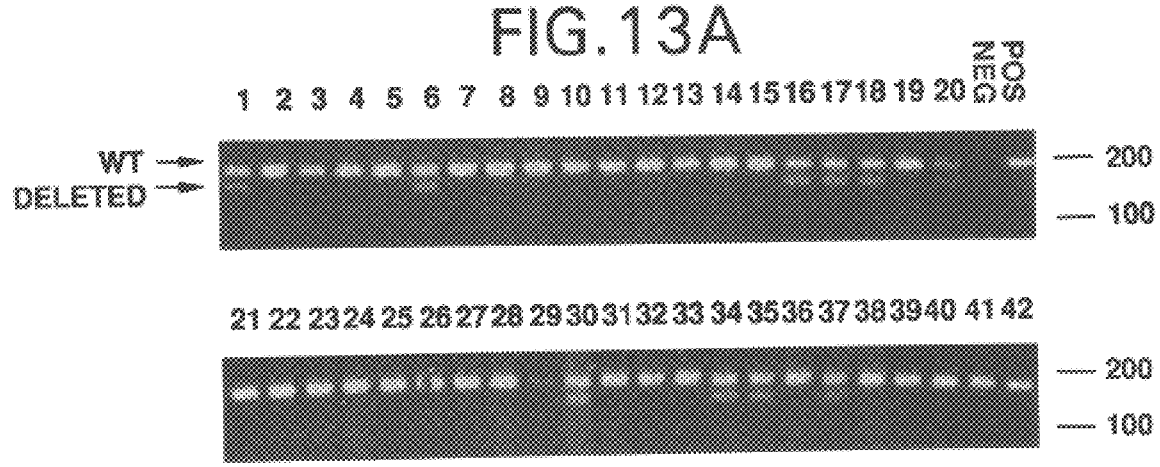
Figure 13B:
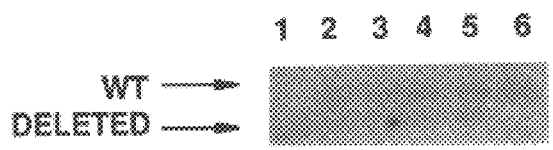

Deleted CKR-5 heterozygotes are common and can be infected. Resistance to HIV-1 infection is rare. Of a large number of PBMCs from random blood donors, all were readily infected by T-tropic and macrophage-tropic HIV-1 [Spira and Ho, J. Virol. 69: 422–429 (1995)]. Because the pool size from which EU2 and EU3 were selected is unknown, we were not able to estimate the frequency of resistant individuals. To estimate the allele frequency in a population with a genetic background similar to that of EU2 and EU3 (both are of European descent), we tested a panel of genomic DNAs [MacDonald et al., 1991, supra; Mac-Donald et al., Nature Genet. 1: 99–103 (1992)] isolated from unrelated individuals of Western European origin. Of the 44 samples tested, 10 (22.7%) were heterozygous for the deletion; and the rest showed only the wild-type allele (FIG. 13A). The heterozygous status of these samples was confirmed by genomic southern analysis (FIG. 13B and data not shown). Two other panels of genomic DNAs [MacDonald et al., 1991, supra; MacDonald et al., 1992, supra] isolated from individuals of western European origin showed a 15.6% (5 out of 32) and 19.6% (9 out of 46) frequency of heterozygotes (data not shown). Thus, among the 122 samples tested, 24 were heterozygous yielding a calculated allele frequency of 0.098. Assuming Hardy-Weinberg equilibrium, this predicts frequencies of 81% wild-type homozygotes, 18% heterozygotes and 1% homozygotes for deleted CKR-5 in populations of western European heritage. In a preliminary analysis of individuals from other backgrounds, genomic DNAs from members of the Venezuela reference mapping resource [Locke et al., Somat. Cell. Mol. Genet. 19: 95–101 (1988); Tanzi et al., Genomics 3: 129–136 (1988)] were tested. No deleted alleles were present in the 46 genomic DNAs tested. Thus, the allele is common in some human populations but much rarer in others. These findings suggest a rather recent evolutionary origin of this mutation.

Individuals that are heterozygous for the CKR-5 deletion could express less coreceptor and as a result replicate virus less efficiently. In a preliminary analysis of the infectability of heterozygous cells, we measured the replication efficiency of a macrophage-tropic HIV-1 strain, SF162, on the CD4$^+$ T-cells of EU2, EU3 and one parent of each. The cells of LW5 were used as a source of wild-type cells. In this analysis, virus replicated efficiently on the wild-type cells, failed to replicate on the EU cells and replicated to an intermediate level on both parental T-cells (data not shown). Preliminary analysis, based on cases analyzed to date, shows that CD4 decline in slope in heterozygotes is about −10 per year, whereas wild-type individuals have an average decline slope of −90 to −100 per year. This finding suggested that heterozygous cells are somewhat reduced in their ability to replicate macrophage-tropic HIV-1, and that CKR5 ± (heterozygosity) is protective from HIV compared to wild type.

Discussion

The data reported here show that two individuals who are resistant to HIV-1 infection in spite of repeated exposures are homozygous for a defect in the gene encoding CKR-5, a major coreceptor for macrophage-tropic HIV-1 isolates. Both individuals have identical CKR-5 alleles containing a 32 bp deletion in a region of the gene corresponding to the second extracellular loop. The deletion results in a frameshift in the DNA sequence that encodes a severely truncated protein. The truncated protein is not detected at the cell surface or in the cytoplasm. The absence of CKR-5 from these cells explains their inability to transduce signals in response to MIP-1β. The mechanism for their enhanced secretion of β-chemokines has not been determined but could have to do with decreased up-take of chemokines as a result of the missing chemokine receptor or to increased chemokine expression due to a lack of negative regulatory signals that normally reduce chemokine synthesis.

These findings suggest that the homozygous deletion in CKR-5 accounts for the resistance of these two individuals to transmission of HIV-1. While it is conceivable that a second, yet undetected defect contributed to their resistance, the finding that the EU cells were fully injectable by A-MLV pseudotypes and by T-tropic HIV-1 argues against the presence of a secondary defect. The CKR-5 deletion is not, however, likely to account for the resistance to infection of all EU individuals. Individuals whose cells are only partially resistant to primary HIV-1 infection could express CKR-5 alleles with reduced coreceptor activity. EU individuals whose cells were fully infectable may resist infection by a yet undefined mechanism.

Both EU individuals in the study reported herein are healthy, without any obvious clinical conditions. The absence of a phenotype associated with the CKR-5 defect may result from the redundant nature of the chemokine system. Several members of the chemokine receptor family have overlapping ligand reactivities and tissue distribution. Thus, in individuals homozygous for the defective allele, the loss of CKR-5 might be compensated by a chemokine receptor such as CKR-1, that has a similar ligand profile. By analogy, rare individuals have been reported that do not express the erythrocyte chemokine receptor, DARC (Duffy antigen), as a result of a 14 bp deletion in the coding sequence [Mallinson et al., Br. J. Haematol 90: 823–829 (1995)]. As in the case of CKR-5, no phenotype was associated with that deletion.

Frequency and evolution of the deleted CKR-5 allele. The deleted allele was present in a surprisingly high percentage of unrelated individuals of western European heritage (about 20% heterozygotes). In contrast, it was present at much lower frequency in a panel of individuals from Venezuela. Assuming Hardy-Weinberg equilibrium, the frequency of CKR-5-deleted homozygotes is about 1% in the general population of persons with western European heritage. The CKR-5 allele status of HIV-1 infected individuals remains to be determined. Presumably, infected individuals who are homozygous for deleted CKR-5 are extremely rare. If transmission through a CKR-5-independent route occurs infrequently, homozygous individuals would not be completely protected. A large-scale analysis to determine the frequency of the deleted CKR-5 allele among HIV-1 infected individuals would permit the calculation of the extent to which homozygosity protects against infection.

It is likely that the deleted CKR-5 allele in the majority of heterozygous and homozygous individuals is inherited. This was suggested by the finding that the lone parents identified for both EU2 and EU3 were each heterozygous. Furthermore, the finding that the deletion was identical in every individual makes it unlikely that a recombination hot-spot continually generates these alleles in the population. It is difficult to estimate when this deletion first occurred; however, its restricted distribution and the absence of secondary mutations in the gene suggest a rather recent evolutionary origin.

There is no reason to believe that the high frequency of heterozygotes among individuals of western European ancestry was due to selection pressure from the virus since HIV-1 has only recently become endemic to this population. However, it is possible that in areas where HIV-1 has been endemic for considerably longer periods of time, a selective advantage would be provided to individuals heterozygous or homozygous for this or similar CKR-5 alleles that may be present in these populations. Precedence for selective pressure to lose expression of a chemokine receptor is provided by the example of the erythrocyte chemokine receptor, DARC. A mutant DARC allele that cannot be expressed in erythrocytes provides resistance to Plasmodium vivax [Horuk et al., Science 261: 1182–1184 (1993)]. Individuals carrying this allele may have a selective advantage in areas where the parasite is endemic.

Whether there is an advantage to heterozygosity for deleted CKR-5 is not clear. While heterozygous cells had a somewhat reduced ability to replicate HIV-1 (4-10-fold less virus production), it is not clear whether this magnitude of decrease would offer significant protection against sexual transmission. Whether there is any protection offered to heterozygotes could be determined by comparing the frequency of deleted allele in HIV-1-infected, HIV-1-exposed but uninfected, and nonexposed individuals. Such an advantage has been described in the case of β-globin mutations. The erythrocytes of individuals heterozygous for a mutation in β-globin are resistant to Plasmodium falciparum. As a result, the frequency of the mutant allele is high in sub-Saharan Africa [Wiesenfeld, Science 160: 437 (1968)]. Selection for the deleted CKR-5 allele, or for other yet unknown CKR-5 polymorphisms, might be most evident in areas of Africa that have a high incidence of HIV-1 infection.

Implications for pathogenesis and transmission of HIV-1. In vitro, seven transmembrane domain proteins in addition to CKR-5, such as fusin, CKR-2B and CKR-3, have been shown to act as coreceptors for various HIV-1 isolates. The relative frequency with which each of these coreceptors is used in vivo is not known. Our findings on the resistance of multiply exposed individuals to HIV-1 infection demonstrates the critical role of CKR-5 in vivo. It is highly likely that HIV-1 transmission proceeds through a CKR-5 dependent event. Fusin and at least some of the other CKR genes appeared to be unaltered in the EU individuals. Thus, these receptors are insufficient for sexual transmission of common strains of the virus.

Given their high numbers of exposures, it is likely that the EU individuals have been exposed to NSI, as well as SI viruses. These individuals have functional fusin and other HIV-1 coreceptors yet do not become infected. It may be that $CD4^+$ cells expressing the other coreceptors are not prevalent among the cells that line the mucosal surfaces at which transmission occurs. Alternatively, transmission followed by systemic spread of virus may be supported only by specific cell-types that express CKR-5 but not fusin or other potential HIV-1 coreceptors. Infection by SI virus of $CD4^+$ T-cells could occur transiently following sexual contact but may not result in systemic spread of the virus. Further replication of the virus might require infection of specialized cells such as macrophages that cannot be infected by SI viruses which use fusin as coreceptor. The properties of $CKR-5^+$ cells such as macrophages that allow them to support systemic spread of HIV-1 are not yet defined, but may be related to their ability to activate T-cells. Transmission of SI virus could result in an abortive infection that is sufficient to establish anti-viral cytolytic T-cells, but which is soon cleared. Rowland-Jones have recently described a cohort of Gambian prostitutes that have been heavily exposed to HIV-1 but remain uninfected [Rowland-Jones et al., 1995, supra]. This phenomenon was associated with a cellular immune response against the virus. The presence of CTL responses against HIV-1 in these individuals is consistent with a transient infection. It will be important to determine the CKR-5 status of such individuals.

This study highlights the critical importance of CKR-5 for HIV-1 transmission. CKR-5 is likely, in addition, to play an important role during the early phases of infection and possibly throughout the course of the disease. CKR-5 could also play a role in determining the rate of disease progression. Some HIV-1-infected individuals remain asymptomatic, with very low viral burdens for unusually long periods of time [Cao et al., N. Engl. J. Med., 332: 201–208 (1995); Pantaleo et al., N. Engl. J. Med. 332: 209–216 (1995)]. It will be important to determine whether such individuals tend to be heterozygous for deleted CKR-5. Decreased levels of functional CKR-5 could be responsible for the low viral burdens that have been reported in these individuals. Alternatively, these individuals could have CKR-5 alleles that encode receptors with reduced ability to mediate HIV-1 entry. Such alleles have not yet been detected but their existence is suggested by previous findings that the PBMC of some EU individuals have a moderate decrease in their ability to support macrophage-tropic HIV-1 replication [Paxton et al., 1996, supra].

The presence of a nonfunctional CKR-5 allele in individuals who are resistant to HIV-1 infection provides insight into the mechanisms governing virus transmission and may in the future provide a more complete understanding of the factors controlling disease progression. The lack of any obvious clinical conditions associated with the absence of functional CKR-5 suggests that this receptor is dispensable. These findings highlight the importance of developing therapeutic agents directed against the HIV-1-CKR-5 interaction. In addition, following the changing frequencies of CKR-5 alleles in heavily infected populations may provide a unique insight into the complex genetic interplay between this pathogen and its host.

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

Various references are cited throughout the specification, the disclosures of which are incorporated herein by reference in their entirety.

What is claimed is:

1. A method for identifying an individual who is resistant to human immunodeficiency virus-1 (HIV-1) infection comprising identifying whether an individual is homozygous, heterozygous, or normal for mutation in the CKR-5 gene that contain a 32 base-pair deletion;

wherein said 32 base-pair deletion has the nucleotide sequence of SEQ ID NO:1; and wherein heterozygosity for a CKR-5 (±) mutation indicates that the individual is more resistant to HIV infection than normal, and homozygosity for a CKR-5 (−/−) mutation indicates that the individual is more resistant than normals or than heterozygous individuals.

2. The method according to claim 1 wherein the individual is identified as being heterozygous for the CKR-5 mutation (±); and wherein the heterozygosity for the CKR-5 mutation indicates that the individual is more resistant than normals to macrophage-tropic HIV-1 viral strains.

3. The method according to claim 1 wherein the individual is identified as being homozygous for the CKR-5 mutation (−/−); and wherein the homozygosity for a CKR-5 mutation indicates that the individual is more resistant than normals and heterozygous individuals to macrophage-tropic HIV-1 viral strains.

4. The method according to claim 1, wherein the mutation is detected by polymerase chain amplification (PCR) analysis.

5. The method according to claim 4, wherein the PCR product of the mutant and normal extracellular loop can be differentiated by specific restriction endonucleases.

6. The method according to claim 5, wherein the PCR analysis is performed by:

(a) amplifying CKR-5 mRNA, cDNA, or genomic DNA using a 5′ primer GCGGATCCCAAAGTCCCTTG-GAACCAGAG (SEQ ID NO:2) and a 3′ primer GGTCTAGACAGGCCACCATTACATTCCCT (SEQ ID NO:3); and (b) detecting the presence of the 32-base pair deletion by a method selected from the group consisting of (i) sequencing the amplified region; wherein the sequence of the PCR product amplified from the mutant has a 32-base pair deletion; and (ii) determining the size of the PCR products by electrophoresis, and comparing the size of the PCR product to the size of the PCR product from a wild-type CKR-5 gene, wherein the size of the PCR product from the mutant is 32 base pairs smaller than the wild-type PCR product.

7. The method according to claim 5, wherein the PCR analysis is performed by:

(a) amplifying CKR-5 mRNA, cDNA, or genomic DNA using a SP4.760 5′ primer CTTCATTACACCTG-CAGCTCT (SEQ ID NO:8) and a PM6.942 3′ primer CACAGCCCTGTGCCTCTTCTTC (SEQ ID NO:9); and (b) detecting the presence of the 32-base pair deletion by a method selected from the group consisting of (i) sequencing the amplified region, wherein the sequence of the PCR product amplified from the mutant has a 32-base pair deletion; and (ii) determining the size of the PCR products by electrophoresis, wherein the PCR product from a wild-type CKR-5 gene is about 182 base pairs, and the PCR product from a mutant CKR-5 gene is about 150 base pairs.

8. The method according to claim 1, wherein the mutation is detected by Southern analysis.

9. The method according to claim 8, wherein the Southern analysis is performed by (a) cleaving genomic DNA with restriction enzyme and separating it by electrophoresis on an agarose gel;

(b) transferring the separated DNA to a nitrocellulose filter and hybridizing with a labeled CKR-5 specific probe; and (c) detecting a difference in the size of restriction fragments hybridized by the probe compared to the size from a wild-type individual; wherein detection of a restriction fragment that is 32 base pairs smaller than wild-type is indicative of the mutation.

10. The method according to claim 8, wherein the restriction enzymes are EcoRI and BglII, the probe is a BamHI-SalI cleaved CKR-5 cDNA insert labeled with ($\alpha$-$^{32}$P)dCTP, and the wild-type fragment is 283 base pairs and the mutant is 251 base pairs.

11. The method according to claim 1 for identifying a homozygous CKR-5 (−/−) individual, wherein the mutation is detected by detecting hybridization of an oligonucleotide probe corresponding to the 32 base pair deletion with a sample from the individual selected from the group consisting of mRNA (Northern analysis), cDNA, and genomic DNA (Southern analysis), wherein hybridization of the probe to the sample indicates that the individual is not homozygous CKR-5 (−/−).

12. The method according to claim 1 for identifying a homozygous CKR-5 (−/−) or heterozygous CKR-5 (±) individual, wherein the mutation is detected by detecting hybridization of a first oligonucleotide probe corresponding to the CKR-5 sequence with the 32 base pair deletion with a sample from the individual selected from the group consisting of mRNA (Northern analysis), cDNA, and genomic DNA (Southern analysis), wherein the hybridization of the probe to the sample indicates that the individual is homozygous CKR-5 (−/−)or heterozygous CKR-5 (±).

13. The method according to claim 12, further comprising detecting hybridization of a second oligonucleotide probe corresponding to the 32 base pair deletion, wherein the hybridization of the first probe but not the second probe indicates that the individual is homozygous CKR-5 (−/−); wherein the hybridization of both the first and second probes indicates that the individual is heterozygous CKR-5 (±); and wherein hybridization of the second probe but not the first probe indicates that the individual is wild type.

* * * * *